(12) United States Patent
Dubrovskaya et al.

(10) Patent No.: US 10,174,292 B2
(45) Date of Patent: Jan. 8, 2019

(54) SOLUBLE HIV-1 ENVELOPE GLYCOPROTEIN TRIMERS

(71) Applicants: International AIDS Vaccine Initiative, New York, NY (US); The Scripps Research Institute, La Jolla, CA (US)

(72) Inventors: Viktoriya Dubrovskaya, La Jolla, CA (US); Francisco Javier Guenaga, New York, NY (US); Richard Wyatt, La Jolla, CA (US)

(73) Assignees: International AIDS Vaccine Initiative, New York, NY (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/075,329

(22) Filed: Mar. 21, 2016

(65) Prior Publication Data

US 2016/0272948 A1 Sep. 22, 2016

Related U.S. Application Data

(60) Provisional application No. 62/136,365, filed on Mar. 20, 2015, provisional application No. 62/145,855,
(Continued)

(51) Int. Cl.
*A61K 39/21* (2006.01)
*C12N 7/00* (2006.01)
(Continued)

(52) U.S. Cl.
CPC ........... *C12N 7/00* (2013.01); *A61K 39/12* (2013.01); *A61K 39/21* (2013.01); *A61K 39/39* (2013.01);
(Continued)

(58) Field of Classification Search
None
See application file for complete search history.

(56) References Cited

U.S. PATENT DOCUMENTS

| 2013/0139274 A1 | 5/2013 | Sanders |
| 2014/0212458 A1* | 7/2014 | Caulfield ............... A61K 39/21 424/400 |
| 2015/0183835 A1 | 7/2015 | Carfi et al. |

FOREIGN PATENT DOCUMENTS

| EP | 2873423 A2 | 5/2015 |
| WO | 2013/189901 | 12/2013 |
| WO | 2015/004158 A1 | 1/2015 |

OTHER PUBLICATIONS

Yasmeen et al., "Differential binding of neutralizing and non-neutralizing antibodies to native-like soluble HIV-1 Env trimers, uncleaved Env proteins, and monomeric subunits," Retrovirology 11:41 (2014).*

(Continued)

*Primary Examiner* — Janet L Andres
*Assistant Examiner* — M Franco G Salvoza
(74) *Attorney, Agent, or Firm* — Duane Morris LLP; Thomas J. Kowalski; Deborah L. Lu

(57) ABSTRACT

The present application relates to novel HIV-1 envelope glycoproteins which may be utilized as an HIV-1 vaccine immunogens, antigens for crystallization and for the identification of broad neutralizing antibodies. The present invention encompasses the preparation and purification of immunogenic compositions which are formulated into the vaccines of the present invention.

15 Claims, 82 Drawing Sheets

Specification includes a Sequence Listing.

Related U.S. Application Data filed on Apr. 10, 2015, provisional application No. 62/164,459, filed on May 20, 2015, provisional application No. 62/234,782, filed on Sep. 30, 2015, provisional application No. 62/251,872, filed on Nov. 6, 2015.

(51) Int. Cl.

| | | |
|---|---|---|
| *A61K 39/12* | (2006.01) | |
| *A61K 39/39* | (2006.01) | |
| *C07K 14/005* | (2006.01) | |
| *A61K 39/00* | (2006.01) | |

(52) U.S. Cl.
CPC ............... *A61K 2039/55505* (2013.01); *A61K 2039/55511* (2013.01); *A61K 2039/55555* (2013.01); *A61K 2039/55577* (2013.01); *C07K 14/005* (2013.01); *C12N 2740/16122* (2013.01); *C12N 2740/16134* (2013.01)

(56) References Cited

OTHER PUBLICATIONS

European Search Report dated Feb. 9, 2017, which issued during prosecution of European Application No. 16020091.1.

Sharma, et al. "Cleavage-Independent HIV-1 Env Trimers Engineered as Soluble Native Spike Mimetics for Vaccine Design" Cell Reports, Apr. 2015, 11(4):539-550.

Partial European Search Report dated Jul. 29, 2016, which issued during prosecution of European Application No. 16020091.

Dey, et al. "Specific amino acids in the N-terminus of the gp41 ectodomain contribute to the stabilization of a soluble, cleaved gp140 envelope glycoprotein from human immunodeficiency virus type 1" Virology 2007, 360:199-208.

Melchers, et al. "A stabilized HIV-1 envelope glycoprotein trimer fused to CD40 ligand targets and activates dendritic cells" Retrovirology 2011, 8:48.

James M. Kovacs, et al., Stable, Uncleaved HIV-1 Envelope Glycoprotein gp140 Forms a Tightly Folded Trimer with a Native-like Structure, PNAS (Dec. 15, 2014) vol. 111, No. 52, p. 18542-18547.

Sanders, et al., Stabilization of the Soluble, Cleaved, Trimeric Form of the Envelope Glycoprotein Complex of Human Immunotherapy Virus Type 1, Journal of Virology, The American Society for Microbiology, US (Sep. 1, 2002) vol. 76, No. 17, p. 8875-8889.

S. Kesavardhana, et al. Stabilizing the Native Trimer of HIV-1 Env by Destabilizing the Heterodimeric Interface of the gp41 Postfusion Six-Helix Bundle, Journal of Virology (Sep. 1, 2014) vol. 88. No. 17, p. 9590-9604.

Office Action issued in co-pendtng EP Application No. EP 18020092.9 dated Apr. 18, 2018.

\* cited by examiner 1. 16055 NFL TD GL L568G

JRFL NFL2 TD plus three stabilizing mutations in gp41
(L543N, Q567K and G588R)
MPMGSLQPLATLYLLGMLVASVLAVEKLWVTVYYGVPVWKDAETTLFCASDAKAYDTEKHNVWA
THACVPTDPNPQEVVLENVTEHFNMWKNNMVEQMQTDIISLWDQSLKPCVKLTPLCVTLNCKDV
NATNTTNDSEGTMERGEIKNCSFNITTSLRDKVQKEYALFYKLDVVPIDNNNTSYRLISCDTSV
ITQACPKISFEPIPIHYCAPAGFAILKCNDKTFNGKGPCKNVSTVQCTHGIRPVVSTQLLLNGS
LAEEEVVIRSDNFTNNAKTIIVQLKESVEINCTRPNNNTRKSIHIGPGRAFYTTGEIIGDIRQA
HCNISRAKWNDTLKQIVIKLREQFENKTIVFNHSSGGDPEIVMHSFNCGGEFFYCNSTQLFNST
WNNNTEGSNNTEGNTITLPCRIKQIINMWQRVGQAMYAPPIRGQIRCSSNITGLLLTRDGGINE
NGTEIFRPGGGDMRDNWRSELYKYKVVKIEPLGVAPTRAKRRVVQGGGGSGGGGSAVGIGAVFL
GFLGAAGSTMGAASMTLTVQARNLLSGIVQQQNNLLRAPEAQQRMLKLTVWGIKQLQARVLAVE
RYLRDQQLLGIWGCSGKLICTTAVPWNASWSNKSLDRIWNNMTWMEWEREIDNYTSEIYTLIEE
SQNQQEKNEQELLELDGGGGSHHHHHHHH

FIG. 16

| Trimer | t1/2, °C | Tm, °C |
|---|---|---|
| JRFL NFL2 TD | 5.84 | 55.2 |
| JRFL NFL2 TD gp 1-3 | 5.62 | 57.8 |

JRFL NFL2 TD12 (L543N, N553S, G588R, E662A)
MPMGSLQPLATLYLLGMLVASVLAVEKLWVTVYYGVPVWKDAETTLFCASDAKAYDTEKHNVWA
THACVPTDPNPQEVVLENVTEHFNMWKNNMVEQMQTDIISLWDQSLKPCVKLTPLCVTLNCKDV
NATNTTNDSEGTMERGEIKNCSFNITTSLRDKVQKEYALFYKLDVVPIDNNNTSYRLISCDTSV
ITQACPKISFEPIPIHYCAPAGFAILKCNDKTFNGKGPCKNVSTVQCTHGIRPVVSTQLLLNGS
LAEEEVVIRSDNFTNNAKTIIVQLKESVEINCTRPNNNTRKSIHIGPGRAFYTTGEIIGDIRQA
HCNISRAKWNDTLKQIVIKLREQFENKTIVFNHSSGGDPEIVMHSFNCGGEFFYCNSTQLFNST
WNNNTEGSNNTEGNTITLPCRIKQIINMWQRVGQAMYAPPIRGQIRCSSNITGLLLTRDGGINE
NGTEIFRPGGGDMRDNWRSELYKYKVVKIEPLGVAPTRAKRRVVQGGGGSGGGGSAVGIGAVFL
GFLGAAGSTMGAASMTLTVQARNLLSGIVQQQSNLLRAPEAQQRMLQLTVWGIKQLQARVLAVE
RYLADQQLLGIWGCSGKLICTTAVPWNASWSNKSLDRIWNNMTWMEWEREIDNYTSEIYTLIEE
SQNQQEKNEQELLALDGGGGSHHHHHHHH

FIG. 18

FIG. 26A
FIG. 26B
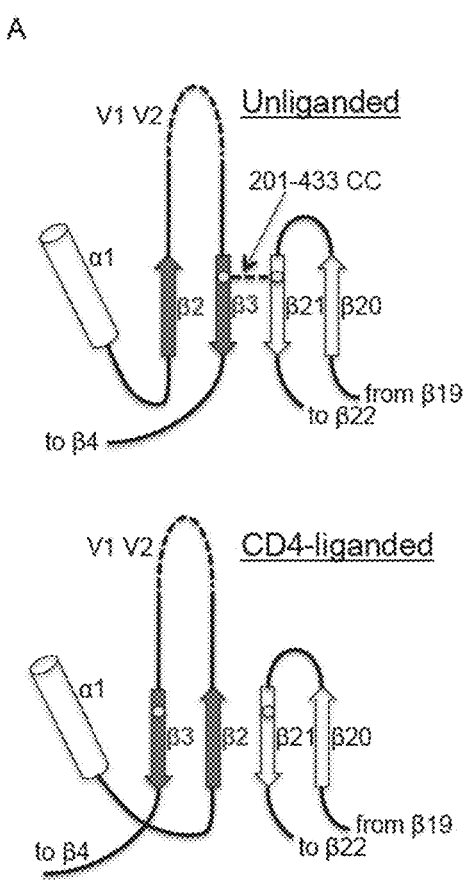
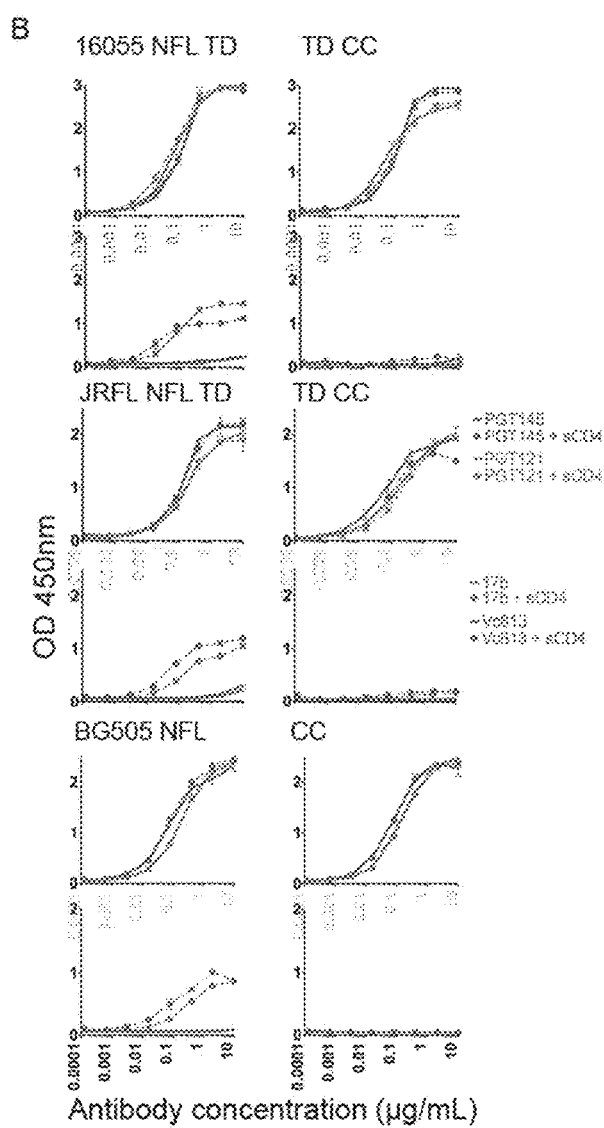

| JRFL NFL wt | TD₈ | TD₁₂ | TD₁₄ | TD₁₅ |
|---|---|---|---|---|
| $T_m$ = 54.3 °C | 55.4 °C | 60.2 °C | 62.4 °C | 63.3 °C |
| $T_{on}$ = 46.7 °C | 48.2 °C | 50.1 °C | 51.7 °C | 52.1 °C |
| $T_{1/2}$ = 5.6 °C | 5.2 °C | 4.9 °C | 4.9 °C | 4.8 °C |

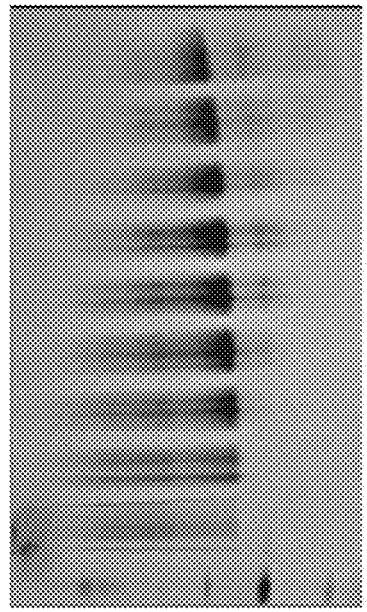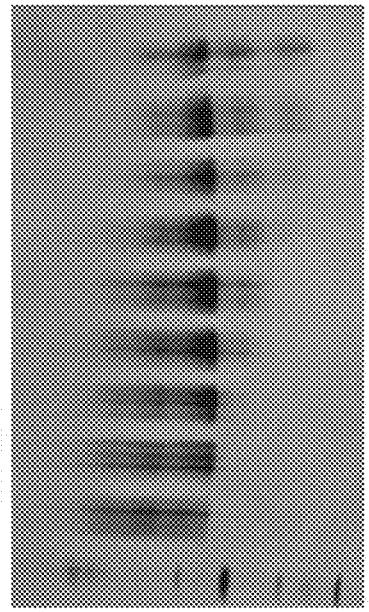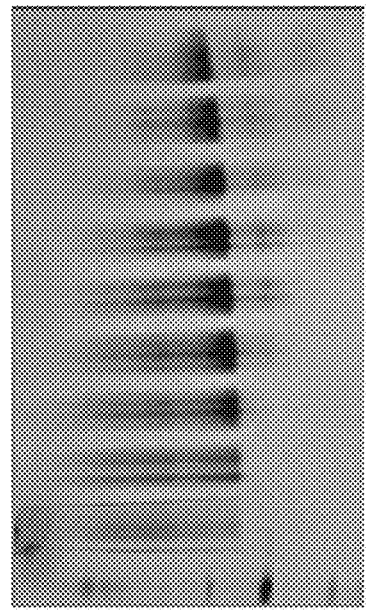
Single Mutant SEC Fractions
FIG. 43

| Mutation(s) | Increase in Tm Predicted | Actual |
|---|---|---|
| 302Y | N/A | 1.06 |
| 513Y | N/A | 0.96 |
| 519R | N/A | 2.64 |
| 520R | N/A | 1.85 |
| 519R520R | 4.49 | 3.66 |
| 302Y519R | 3.7 | 4.3 |
| 302Y520R | 2.91 | 3.66 |
| 302Y519R520R | 5.55 | 6.28 |

FIG. 53

FIG. 56A
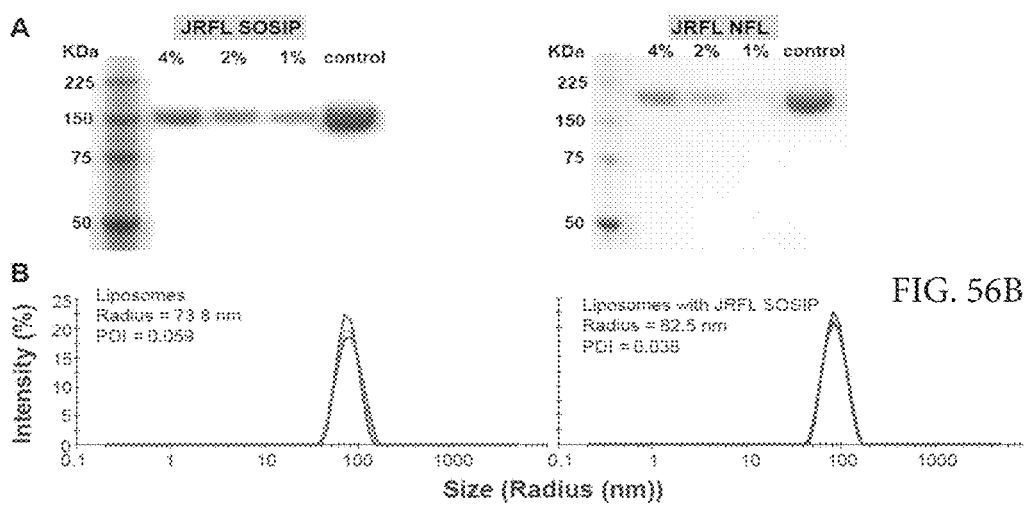
FIG. 56B
FIG. 56C
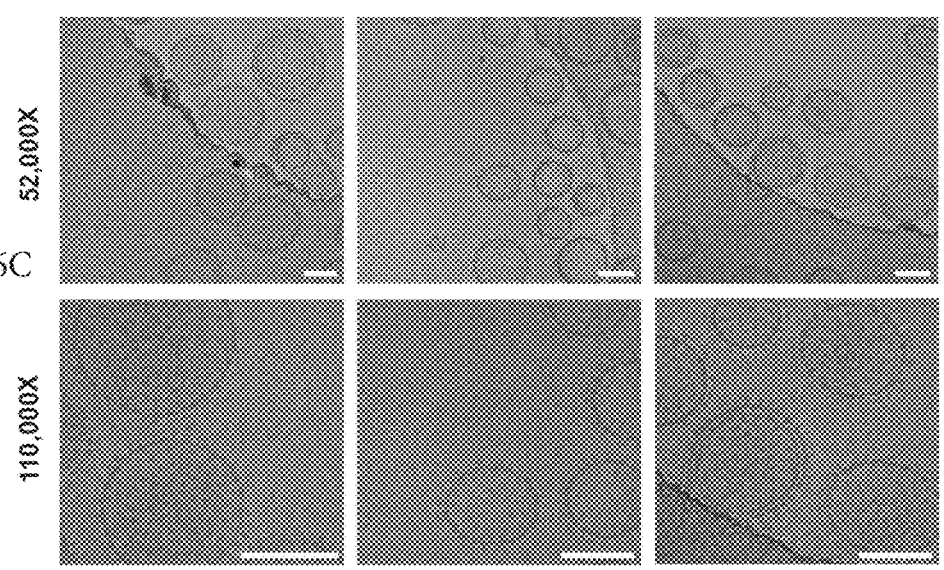

FIG. 57A
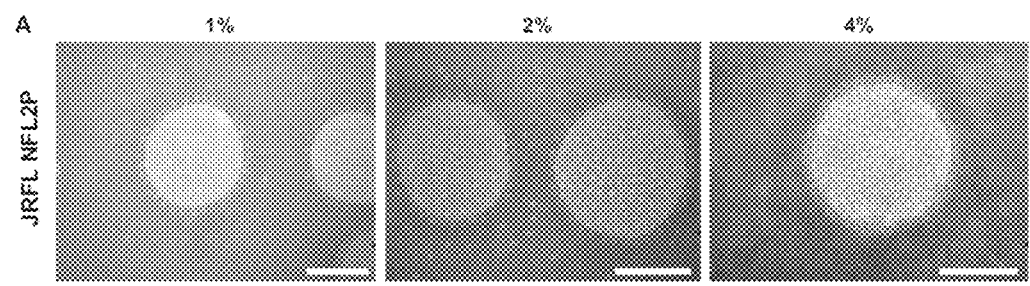
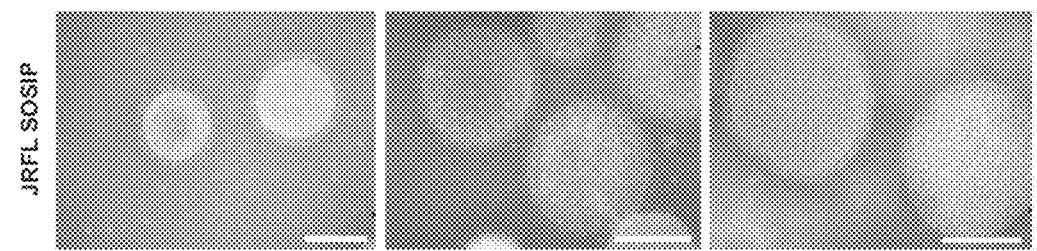
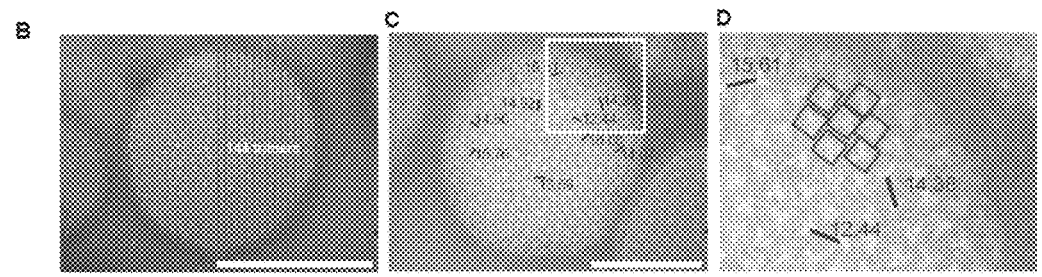
FIG. 57B FIG. 57C FIG. 57D

FIG. 58A
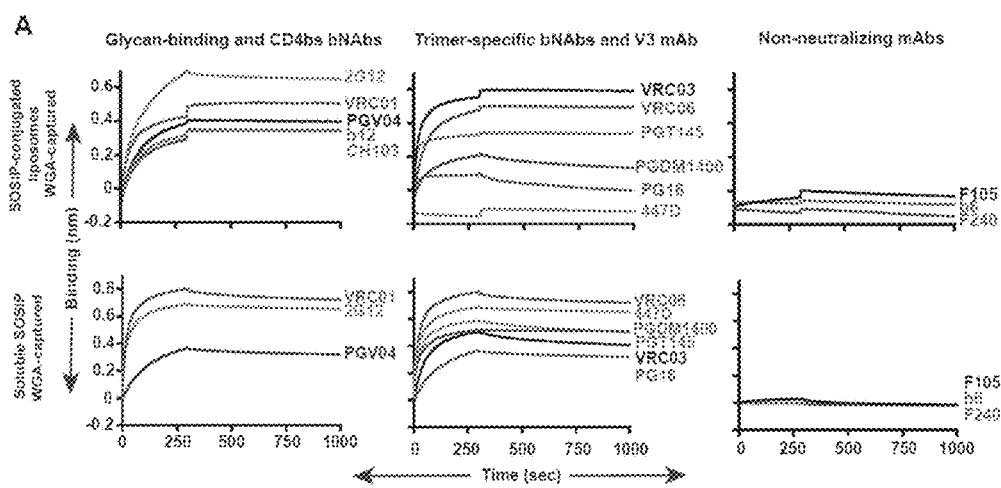
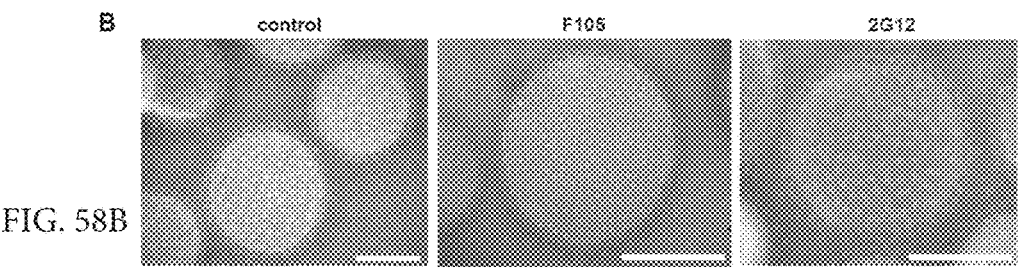
FIG. 58B

FIG. 61A
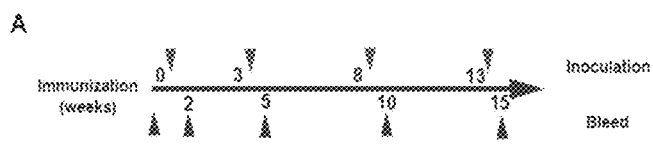
FIG. 61B
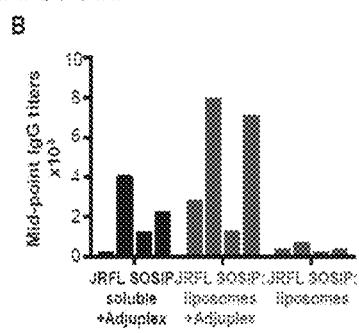
FIG. 61C
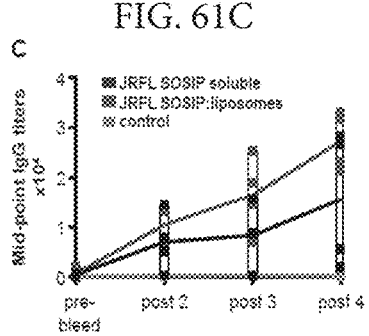
FIG. 61D
FIG. 61E
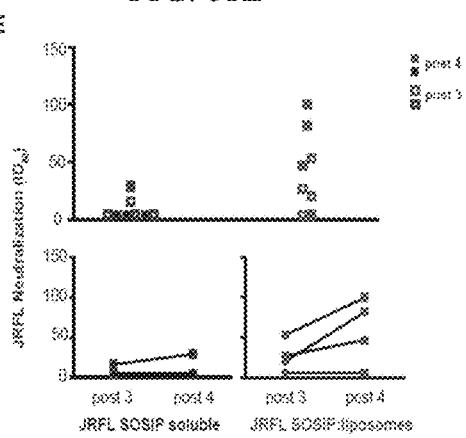

FIG. 62A
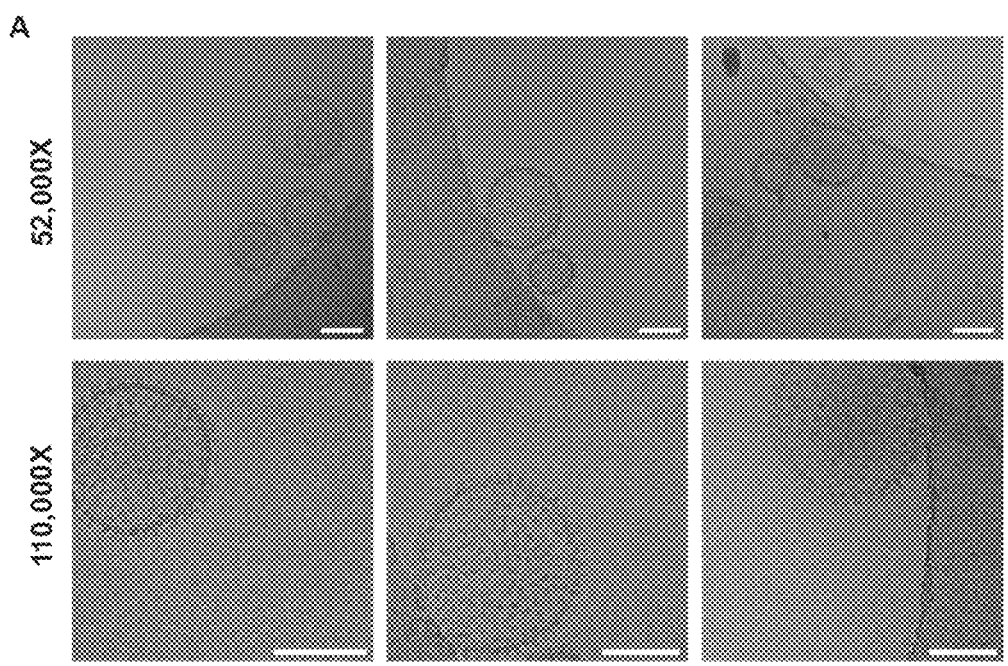
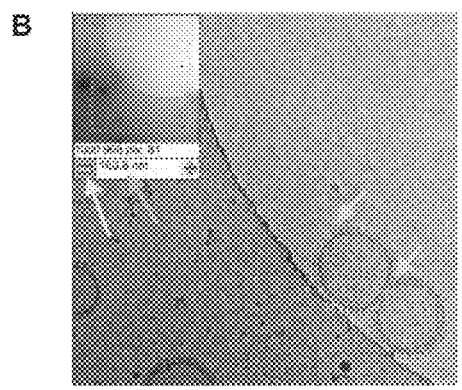
FIG. 62B

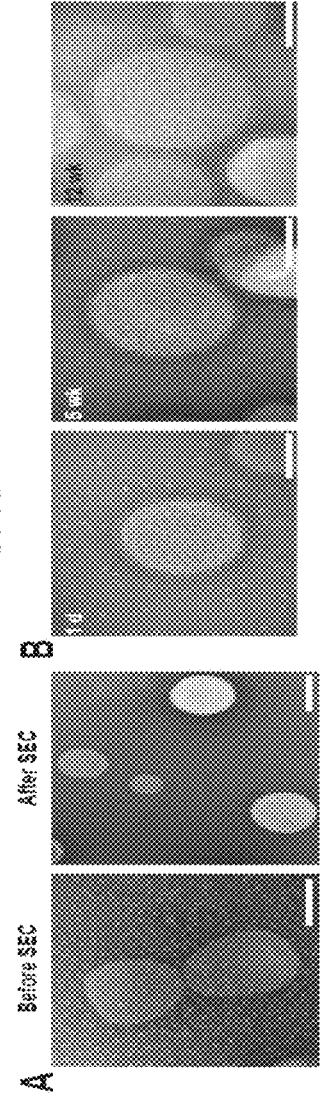
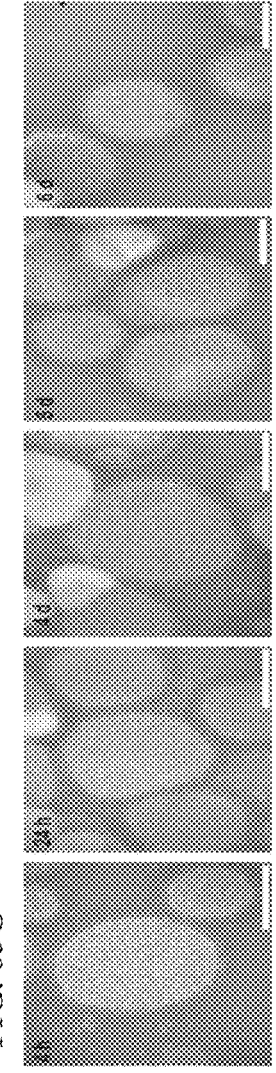
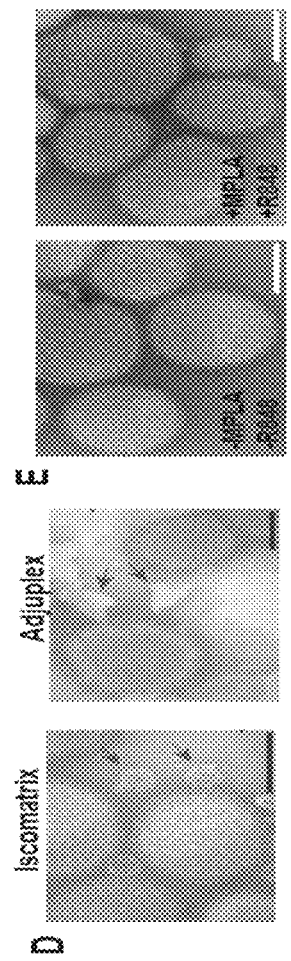
FIG. 63A  FIG. 63B  FIG. 63C  FIG. 63D  FIG. 63E FIG. 64A
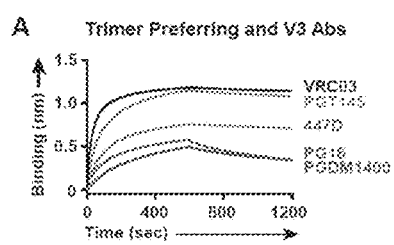
FIG. 64B
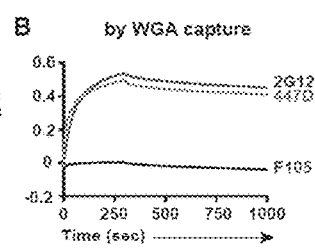
FIG. 64C
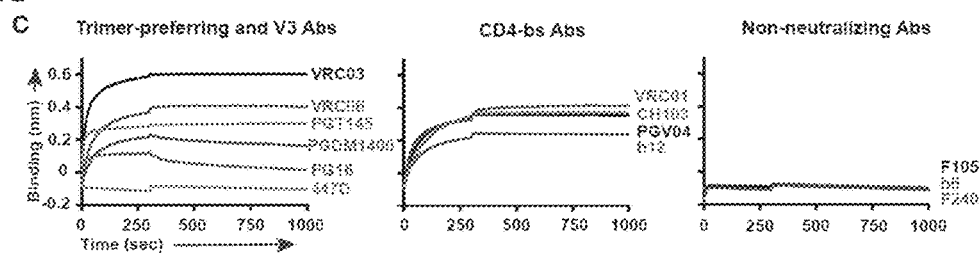
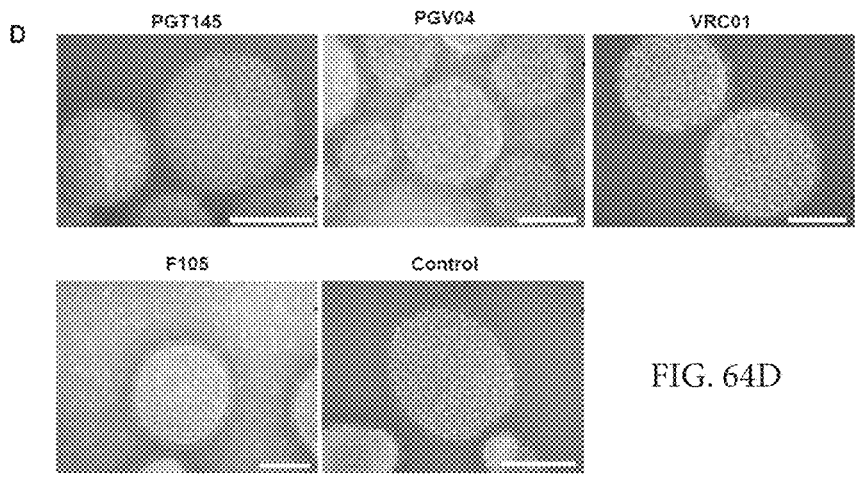
FIG. 64D

|  | Group I 16CC332GL2 | | | Group II 16CC332GL2 Δ276Δ463 | | |
|---|---|---|---|---|---|---|
|  | w0 | w6 | w18 | w0 | w6 | w18 |
| 16055wt | <10 | <10 | 17.29 | <10 | 12.75 | 58.15 |
|  | <10 | <10 | <10 | <10 | <10 | 19.61 |
|  | <10 | <10 | <10 | <10 | 13.59 | <10 |
| 16055 Δ276 | <10 | <10 | 16.6 | <10 | 12.56 | 170.2 |
|  | <10 | <10 | <10 | <10 | <10 | 76.55 |
|  | <10 | <10 | <10 | <10 | <10 | 158.3 |
| 16055 Δ276Δ360 Δ463 | <10 | <10 | 23.13 | <10 | 178.4 | 12.06 |
|  | <10 | <10 | <10 | <10 | <10 | 22.56 |
|  | <10 | <10 | <10 | <10 | 319.9 | 613.6 |

FIG. 81

SOLUBLE HIV-1 ENVELOPE GLYCOPROTEIN TRIMERS

RELATED APPLICATIONS AND/OR INCORPORATION BY REFERENCE

This application claims benefit of and priority to U.S. provisional patent application Ser. No. 62/136,365 filed Mar. 20, 2015, U.S. provisional patent application Ser. No. 62/145,855 filed Apr. 10, 2015, U.S. provisional patent application Ser. No. 62/164,459 filed May 20, 2015, U.S. provisional patent application Ser. No. 62/234,782 filed Sep. 30, 2015 and U.S. provisional patent application Ser. No. 62/251,872 filed Nov. 6, 2015.

Reference is made to U.S. patent application Ser. No. 14/508,369 filed Oct. 7, 2014 which claims priority to U.S. provisional patent application Ser. Nos. 62/054,727 filed Sep. 24, 2014, 62/032,507 filed Aug. 1, 2014, 61/941,101 filed Feb. 18, 2014 and 61/887,618 filed Oct. 7, 2013.

Reference is also made to international patent application Serial No. PCT/US11/26862 filed Mar. 2, 2011 which published as international patent publication WO 2011/109511 on Sep. 9, 2011 and claims priority to U.S. provisional patent application Ser. No. 61/309,685 filed Mar. 2, 2010. Reference is also made to U.S. provisional patent application Ser. Nos. 61/664,990 and 61/722,739 filed Jun. 27, 2012 and Nov. 5, 2012, respectively.

The foregoing applications, and all documents cited therein or during their prosecution ("appln cited documents") and all documents cited or referenced in the appln cited documents, and all documents cited or referenced herein ("herein cited documents), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Apr. 26, 2016, is named 43094_05_2035_SL.txt and is 12,972 bytes in size.

FIELD OF THE INVENTION

This application relates to a novel HIV-1 envelope glycoprotein which may be utilized as an HIV-1 vaccine immunogen, as a native Env trimer mimic, for identification of small molecules for use as immunogen that bind specific HIV-1 broad neutralizing antibodies, for identification of small molecules for use as anti-viral compound that bind specific HIV-1 envelope glycoprotein monomer and/or trimer, as antigens for crystallization and electron microscopy (EM) structural analysis and for the identification of broad neutralizing antibodies from HIV-1 infected individuals or vaccinated subjects or antibody or ligand libraries.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells.

In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system.

Recently using a sensitive high-throughput micro-neutralization screening of supernatants from approximately 30,000 IgG+memory B cells from a HIV-1 clade A-infected African donor, Applicants identified two new bNabs PG9 and PG16 that are broad and exceptionally potent neutralizing antibodies (Walker L, Phogat S, et al. Science. 2009; 326:285-9. Epub 2009 Sep. 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-1 trimer.). When tested for binding, these antibodies did not show binding to many empirically designed soluble (Env gp140) HIV Env trimer thought to be mimics of the native HIV-1 Env spike, suggesting that either these Env designs are either incorrect or they are fixed in a form not recognized by PG9 and PG16.

Citation or identification of any document in this application is not an admission that such document is available as prior art to the present invention.

SUMMARY OF THE INVENTION

A first embodiment of the present invention relates to an engineered or non-naturally occurring trimeric Env trimer, advantageously a disulfide stabilized SOSIP trimer and/or a flexibly linked NFL2P trimer derived from the subtype A BG505 Env, having one or more BG505 Trimer-Derived mutations ("TD mutations"), wherein said TD mutations may comprise one or more mutations at residue 47, 49, 65, 106, 165, 429, 432, 500, 543, 553, 567, 588 and/or 662. In particular, the mutations may include D at residue 47, E at residue 49, K at residue 65, T at residue 106, L at residue 165, R at residue 429, Q at residue 432, R at residue 500, N at residue 543, S at residue 553, K at residue 567, R at residue 588 and/or A at residue 662. In another embodiment, there may be additional mutations at residues 568 and/or 569. In this embodiment, the mutations may include G at residues 568 and/or 569.

A second embodiment of the present invention relates to an engineered or non-naturally occurring trimeric Env trimer, advantageously a disulfide stabilized SOSIP trimer and/or a flexibly linked NFL2P trimer derived from the subtype A BG505 Env, having a disulfide linkage to prevent CD4-induced conformational changes to lock gp120 in the native-trimer state, wherein the disulfide linkage may be at residues 201 and 433 that covalently links the β-sheet 3 to β-sheet 21.

A third embodiment of the present invention relates to an engineered or non-naturally occurring trimer, wherein the trimer is a disulfide stabilized SOSIP trimer and/or a flexibly linked NFL2P trimer derived from the subtype A BG505 Env, wherein the trimer may comprise one or more BG505 or JRFL trimer-derived mutations ("TD mutations"), wherein said TD mutations may comprise one or more deletions at N276, N301, N322, N360 and/or N463, wherein the trimer better elicits antibodies against a CD4 binding site as compared to a trimer without the one or more deletions at N276, N301, N360 and/or N463. The trimer may be a 16055 NFL TD GL trimer.

The engineered or non-naturally occurring trimeric Env trimer may comprise both a disulfide stabilized SOSIP trimer and/or a flexibly linked NFL2P trimer derived from the subtype A BG505 Env as illustrated in FIG. 2.

A fourth embodiment of the present invention encompasses methods of eliciting an immune response which may comprise administering to a mammal the any of the trimers disclosed herein. The method may further comprise adding an adjuvant. The adjuvant may be a lecithin and may optionally be combined with an acrylic polymer, a lecithin coated oil droplet in an oil-in-water emulsion or a lecithin and an acrylic polymer in an oil-in-water emulsion. The adjuvant may be ISCOMATRIX or Adjuplex. In another embodiment, the adjuvant may comprise alum.

In another embodiment, the trimer may be administered in a liposome or a nanoparticle. In another embodiment, the trimer may be fixed, for example, in glutaraldehyde. Advantageously, the trimers may be fixed in about 5 mM glutaraldehyde, which may be for about five minutes. In another embodiment, the chemically fixed trimers are quenched with glycine.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 16 depicts JRFL NFL2 TD plus three stabilizing mutations in gp41 (L543N, Q567K and G588R) (SEQ ID NO: 5).

FIG. 18 depicts JRFL NFL2 TD12 plus four mutations: L543N, N553S, G588R, E662A (SEQ ID NO: 6).

FIGS. 26A-B depicts an effect of the stabilizing disulfide (201-433CC) on CD4-induced trimer antigenicity (A) Cartoon model of the pre-bridging sheet region of the HIV trimer depicting the location of the residues implicated in the formation of the stabilizing intra-protomer disulfide (201-433CC) marked here as yellow circles. The residues 201 and 433 are located within a disulfide linkage reach in adjacent β-strands (201 on β3 and 433 on β21) in the unliganded HIV trimer while they are separated by a third β-strand β2 when the trimer is CD4-liganded as suggested by CD4-liganded crystal structures. (B) ELISA experiment depicting antigenic changes observed on NFL trimers following CD4 induction. Solid lines represent trimer binding of antibodies in the absence of sCD4-induced conformational changes whereas dotted lines represent binding of antibodies following sCD4-induced conformational changes.

FIG. 43 depicts single mutant SEC fractions which loaded too much protein so they look aggregated, but actually had solid purification profiles.

FIG. 53 depicts an analysis that shows there is not a direct translation of additive effects as Applicants assumed but Applicants assume synergistic effects are causing the enhanced melting temps.

FIGS. 56A-C depict characterization of JRFL SOSIP-conjugated liposomes. (A) Reducing SDS PAGE of 4%, 2% and 1% Ni DGS-NTA(Ni) JRFL SOSIP and JRFL NFL trimer-conjugated liposomes. JRFL SOSIP and JRFL NFL2P soluble trimeric glycoproteins are included as controls. (B) Dynamic light scattering (DLS) of the 4% DGS-NTA(Ni) liposomes and JRFL SOSIP-conjugated liposomes was performed using a using Zetasizer Nano instrument to measure particle size and the polydispersity index. (C) Cryo-EM images of 4% Ni JRFL SOSIP liposomes at 52,000 and 110,000× magnification. Scale bar=100 nm. See also FIG. S1.

FIGS. 57A-D depict incorporation of different amounts of DGS-NTA(Ni) into the liposomes to increase JRFL trimer density on the liposomal surface. Negative stain EM images of DGS-NTA(Ni) liposomes made with 1%, 2% and 4% DGS-NTA(Ni) and conjugated with either JRFL NFL or JRFL SOSIP trimers. All images are at 18,000× magnification. Scale bar=100 nm. (B) Representative negative stain image of 4% JRFL SOSIP-conjugated liposomes with a counting grid (red lines) to manually determine the approximate number of trimers visible in half the area of the trimer-liposome image. (C) Measurement of distances (nm) between selected trimers as demarked by blue bars, center to center. Numbers indicate the distance between the two adjacent trimers. (D) Zoomed image of the white square area from panel C. See also FIG. S2.

FIGS. 58A-B depict binding of HIV-1 antibodies to JRFL SOSIP trimer-conjugated liposomes and soluble JRFL SOSIP trimer assessed by Bio-Layer Interferometry using Octet and negative stain EM. (A) JRFL SOSIP trimer conjugated to 4% DGS-NTA(Ni) liposomes (equivalent to 75 nmoles of phospholipids) or JRFL SOSIP trimers (10 mg/ml) were immobilized on WGA-captured streptavidin sensors and 20 mg/ml monoclonal antibodies (IgGs) were used as analyte. (B) 2% DGS-NTA(Ni) liposomes conjugated to JRFL SOSIP were incubated with 10 molar excess of respective IgG mAbs at 37° C. for 30 min, stained with phospho-tungstate, viewed by EM and images were obtained with a CCD camera. All images are at 180,000× magnification. Scale bar=100 nm. See also FIG. S3.

FIGS. 59A-D depict activation of primary B cells by soluble JRFL SOSIP trimers and JRFL SOSIP trimer-conjugated liposomes. B cells from b12 mature knock-in mice were negatively selected from splenocytes and induced by overnight incubation with either soluble JRFL SOSIP trimers or 4% liposomes conjugated with JRFL SOSIP trimers. The cell-surface activation markers and the cytokines secreted by the activated cells were analyzed by cell-surface staining or ELISA. (A) FACS staining of cell-surface activation markers plotted as MFI values. Soluble JRFL SOSIP (black); JRFL SOSIP conjugated to liposomes (grey bars). (B) Frequency of CD69+ cells upon activation by 50 μg/ml of soluble trimers or JRFL SOSIP trimer-conjugated liposomes. (C) TNF-α and IL-6 levels present in the supernatants of the B-cells upon overnight activation by soluble JRFL SOSIP trimers (black bars) or JRFL trimer-conjugated liposomes (grey bars) B cells were assessed. (D) MFI values of cell surface activation markers and levels of cytokines produced by B cells upon activation by 50 μg/ml of JRFL SOSIP liposomes or similar dilution of blank liposomes without any trimers on the surface. Statistical comparisons between groups are performed by paired t-test. See also FIG. S4.

FIGS. 60A-C depict immunization with JRFL SOSIP trimer-conjugated liposomes induced enhanced germinal center (GC) formation. (A) Three groups of five C57Bl/6 mice were subcutaneously administered PBS, soluble JRFL SOSIP trimers or JRFL SOSIP trimer-conjugated liposomes. After 14 days, lymph node B cells were analysed for the activation marker, GL7. The percentage of CD19+ GL7+ cells are enumerated. (B) Representative flow cytometry scatter plots from each group of mice shown in (A) were gated over CD19+ cells from lymph nodes. (C) Two groups of five C57Bl/6 mice were subcutaneously administered either blank liposomes or JRFL SOSIP trimer-conjugated liposomes. After 14 days, the lymph nodes are processed and the percentages of CD19+ GL7+ cells are enumerated. P values were calculated with a two-tailed unpaired t test.

FIGS. 61A-E depict immunogenicity of the JRFL SOSIP trimer-conjugated liposomes. (A) Timeline of inoculations and bleeds. Bleeds were collected 2 weeks after each injection. (B) Mid-point IgG titers of individual rabbits immunized 3 times with 25 ug JRFL SOSIP protein as soluble trimers or conjugated to liposomes in the presence or absence of exogenous adjuvant Adjuplex were determined. Sera were collected 2 weeks after the 3rd injection and were analyzed by ELISA with JRFL SOSIP trimers captured on ELISA plate via the C-terminal His6tag (SEQ ID NO: 3). (C) Mid-point IgG titers of rabbits immunized 4 times with JRFL SOSIP soluble protein or JRFL SOSIP conjugated to liposomes. ELISA plates were coated with anti-His monoclonal antibody to capture JRFL SOSIP trimers via the C-terminal His6-tag (SEQ ID NO: 3). (D) Neutralization ID50 values of SF162, HxBc2, and JRFL viruses by antisera following the third and fourth inoculations. Control animals were inoculated with blank liposomes in Adjuplex. (E) Combined JRFL neutralization ID50 values elicited by the soluble trimers compared to the trimer-conjugated liposomes are plotted after third and fourth inoculations. Lower panel shows boosts in ID50 values after the fourth inoculation for both group of rabbits. See also FIG. S5.

FIGS. 62A-B depict characterization of JRFL NFL-conjugated liposomes. (A) Cryo-electron microscope images of 4% Ni JRFL NFL-conjugated liposomes at 52,000 and 110,000× magnification. Scale bar=100 nm. (B) Cryo-electron microscope image measuring the diameter of the JRFL NFL-conjugated liposomes.

FIGS. 63A-E depict conjugation specificity and stability of liposomes. (A) Representative negative stain EM images of DGPC liposomes with no DGS-NTA(Ni) mixed with JRFL SOSIP trimer before and after size exclusion chromatography. (B) 2% DGS-NTA(Ni) liposomes with JRFL NFL trimeric protein were incubated at 4° C. or (C) 37° C. for varying times as indicated on the images and stained by phospho-tungstate for EM analysis. (D) 4% Ni DGPC liposomes with JRFL SOSIP trimeric protein were mixed and incubated at 37° C. for 1 hour with Iscomatrix or Adjuplex and stained by phospho tungstate for EM analysis. Red arrows indicate the adjuvant in both cases. (E) 4% Ni DGPC liposomes without and with MPLA and R848 conjugated with JRFL SOSIP trimers. Scale bar=100 nm.

FIGS. 64A-D depict binding of HIV-1 antibodies to soluble JRFL SOSIP and liposome bound JRFL NFL. Binding of anti-HIV-1 monoclonal antibodies assessed by Bio-Layer Interferometry (BLI) using Octet. (A) Monoclonal antibodies were immobilized on human anti-Fc sensors and soluble JRFL SOSIP protein was used as an analyte. (B) JRFL NFL (10 µg/ml) was immobilized on WGA-captured streptavidin sensors and 20 µg/ml monoclonal antibodies (IgGs) were used as analyte. (C) 4% NTA-Ni liposomes (equivalent to 75 nmoles of phospholipids) conjugated to JRFL NFL were immobilized on WGA-captured streptavidin sensors and 20 µg/ml monoclonal antibodies (IgGs) were used as analyte. (D) 2% NTA-Ni liposomes with JRFL NFL were incubated with 10 molar excess of respective antibodies (IgG) at 37° C. for 30 min and stained with phospho tungstate and viewed by EM. All images are at 180,000 magnification. Scale bar=100 nm.

FIG. 81 depicts eutralizing $ID_{50}$ titers (sera fold dilution) of serum from Group I and Group II rabbits after 1st, 3rd and 4th immunizations (0, 6, 18 weeks).

DETAILED DESCRIPTION

Figure 1:
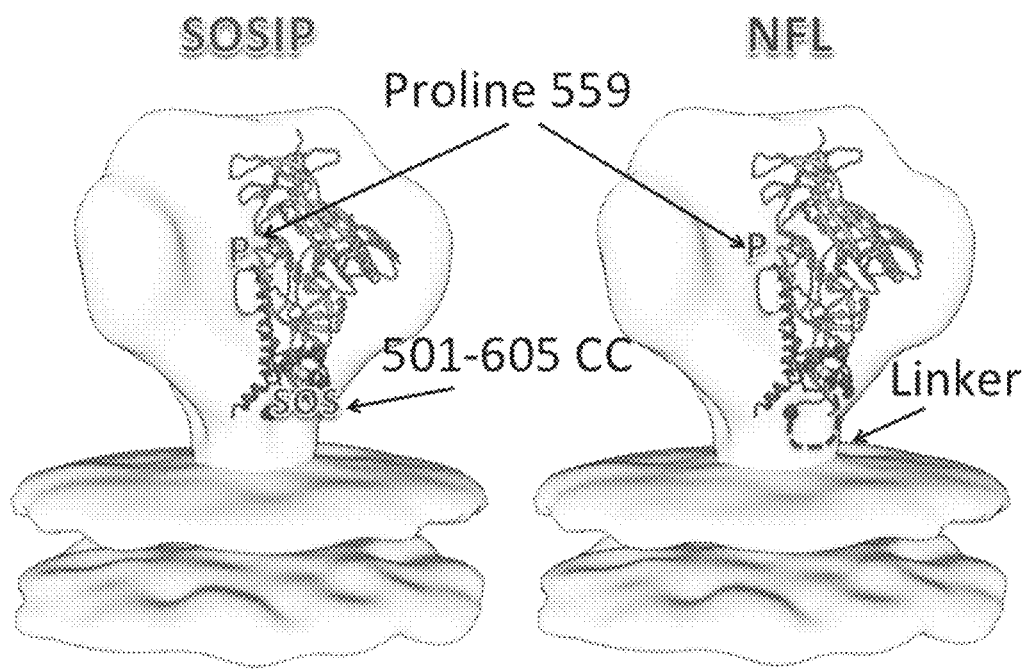
FIG. 1 depicts SOSIP and NFL trimers.

Soluble, stabilized, proteolytically cleaved, trimeric gp41 proteins can be generated by engineering an intermolecular disulphide bond between gp120 and gp41 (SOS), combined with a single residue change, I559P, within gp41 (SOSIP). Applicants previously developed a purification method of homogenous trimers from a mixture of trimers derived from the JRFL clade B virus strain Env. These trimers, known as JRFL SOSIPs may comprise a cysteine pair covalently linking gp120 to gp41, a poly R cleavage site, MPER deletion, a 168 E/K change or a combination thereof. The purification method is scalable, avoids the published 2G12 monoclonal antibody column purification and employs antibody-mediated negative selection to rescue JRFL SOSIP trimers from a heterogenous mixture of trimers in different and 'random' conformation to a high degree of conformational and structural homogeneity, which is expandable to other strains and clades of HIV.

The present invention also encompasses SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP.663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377):336-343), and is also observed for BG505 gp120 (Julien J P, et al. (2013) Proc Natl Acad Sci USA 110(11):4351-4356; Hoffenberg S, et al. (2013) J Virol 87(10):5372-5383).

The SOSIP envelope glycoproteins show significantly better binding to new identified broad neutralizing antibodies PG9 and/or PG16 and are well recognized by all known broadly neutralizing antibodies (bNAbs). The JRFL HPTMs and gp120 MIFs may be recognized by trimer-specific bNabs and likely recognized by bNAbs of other specificities. The envelope glycoproteins Envs have value (a) as reagents for screening of broad neutralizing antibodies (bNAbs), such as but not limited to, PG9 and PG16, the PGT145 family, the PGT128 family and for the SOSIPs the VRC01-like mabs including VRC06, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus, the BG505 virus or the Zm109F virus.

In a particularly advantageous embodiment, the trimer protein, is prepared, purified and formulated for immunization in a human.

In another particularly advantageous embodiment, the trimer protein, is formulated for immunization in a human to contain an adjuvant. A number of adjuvants are well known to those investigating vaccines but could include but are not limited to those containing alum.

In another particularly advantageous embodiment, the trimer protein is further attached to a particle such that multiple copies of the trimer are attached and this material is prepared and formulated for immunization in a human.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or the specification.

Another advantageous embodiment encompasses a stable soluble HIV-1 envelope glycoprotein trimer mimic.

Immunogens in different forms to use as HIV-1 vaccine components to elicit bNabs. The different forms of the HIV-1 envelope are used in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus.

HIV type 1 (HIV-1) envelope is a noncovalent trimer of gp120-gp41 heterodimers, and its lability has hindered structural studies. SOSIP gp140 is a soluble, proteolytically mature form of the HIV-1 envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140. Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-1 envelope trimers. These proteins may be useful as vaccine immunogens and for studying structure-function relationships within the HIV-1 envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-1 strain KNH1144 form particularly homogenous trimers compared to a prototypic strain (JR-FL, subtype B). Described in U.S. Pat. No. 7,939,083 are the determinants of this enhanced stability which are located in the N-terminal region of KNH11144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The HIV-1 envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371): 1884-1888). HIV-1 gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbiol 6(2):143-155). The surface-exposed HIV-1 Env trimer is the sole target for antibodies capable of neutralizing the virus (Burton D R, et al. (2004) Nat Immunol 5(3):233-236). Recently, a myriad of Env-directed broadly neutralizing antibodies (bNAbs) were isolated from numerous HIV-1-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-1 envelope spike. Cell reports 7(3):785-795; Klein F, et al. (2012) J Exp Med 209(8):1469-1479). Infection of macaques by a chimeric model virus, SHIV, can be prevented by prior passive immunization of all bNAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci USA 109(46):18921-18925; Barouch D H, et al. (2013) Therapeutic efficacy of potent neutralizing HIV-1-specific monoclonal antibodies in SHIV-infected rhesus monkeys. Nature 503 (7475):224-228).

Along with virus-specific T cells, an efficacious HIV-1 vaccine therefore would likely need to generate bNAbs targeting Env. Although the premise is simple, in actuality, it is a tremendous challenge without precedent in the history of vaccinology. The difficulty to vaccinate against HIV arises from the extensive variability of Env present on the large number of HIV-1 isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci USA 108(27):11181-11186; Sundling C, et al. (2012) Science translational medicine 4(142):142ra196; Tran K, et al. (2014) Vaccine-elicited primate antibodies use a distinct approach to the HIV-1 primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to V1V2 regions of multiple HIV-1 subtypes correlate with decreased risk of HIV-1 infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-1 infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci USA 111(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-1 primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci USA 109(30):12111-12116; Nkolola J P, et al. (2014) Comparison of multiple adjuvants on the stability and immunogenicity of a clade C HIV-1 gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bNAbs, (GE148 and GE136) generated following immunization of uncleaved gp140 trimers (YU2 gp140-foldon) in non-human primates (NHP). Non-bNAbs, represented by GE136 and 148, can only neutralize the sensitive so-called "tier 1 viruses" that are not representative of the more neutralization resistant tier 2-like primary isolates circulating in the human population. Using crystallography, EM reconstructions, paratope scanning and molecular modeling Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-1 spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNH1144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNH1144 strains. These soluble trimers possess an engineered disulfide linkage between the gp120 and gp41 (at residues 501C and 605C, respectively) and an additional mutation in the heptad repeat 1 (HR1) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-1 primary strains were attempted over the past decade, the BG505- and KNH1144-derived SOSIP trimers are the two limited examples of SOSIPs that yield homogeneous trimers suitable for high resolution biophysical and structural analysis. The structural explanation for the difficulty to readily transfer the SOSIP design to other HIV-1 strain-derived sequences is not yet fully understood and would be valuable information to broaden the trimer design horizon.

An HIV-1 vaccine will likely require multiple native Envs to generate antibodies capable of addressing the diversity of circulating HIV-1. Trimeric Env soluble proteins, typified by the disulfide stabilized SOSIP and the flexibly linked NFL2P molecules derived from the subtype A BG505 Env form highly homogeneous, well-ordered native-like trimers. However, other HIV-1 Env sequences, such as those from subtypes B and C, do so to a lesser degree, requiring negative selection to generate a homogenous sample. Here, Applicants identified trimer-axis proximal gp120 residues that converted the suboptimal trimer formation phenotype displayed by the JRFL and 16055 Envs into a trimer phenotype similar to that displayed by BG505. See, e.g., FIG. 1.

Figure 2:
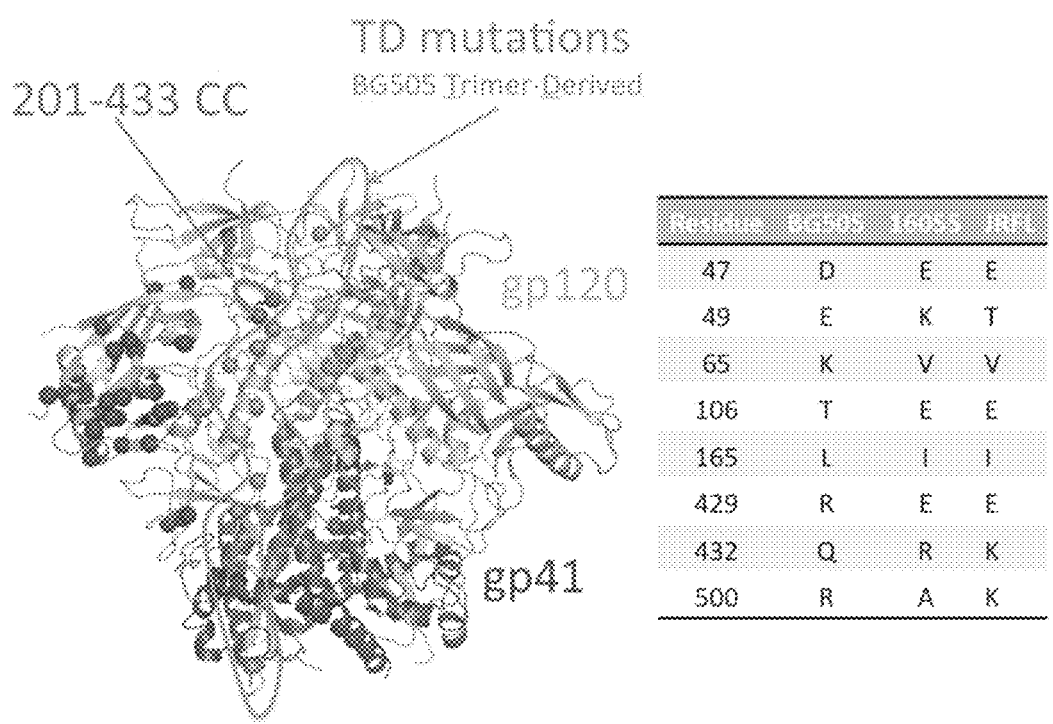
FIG. 2 depicts TD mutations.

Two distinct approaches were taken to improve trimer formation in JRFL SOSIP and 16055 NFL. Firstly, Applicants compared the reference BG505 gp120 sequence with those of JRFL and 16055 gp120s and Applicants annotated all dissimilar residues in the context of the high-resolution BG505 SOSIP structure. A few trimer-axis proximal gp120 residues were selected and reverted in JRFL SOSIP and 16055 NFL. Secondly, Applicants introduced a disulfide linkage at residues 201 and 433 that covalently links the β-sheet 3 to β-sheet 21 to prevent CD4-induced conformational changes to lock gp120 in the native-trimer state. See, e.g., FIG. 2.

Figure 3:
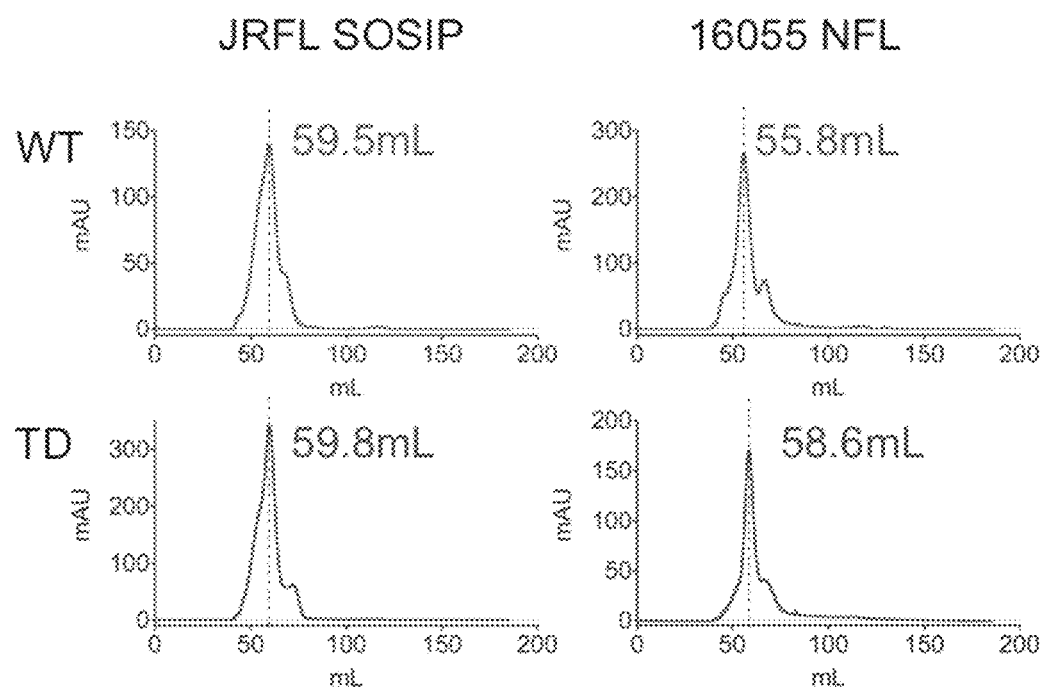
FIGS. 3 and 4 show TD mutations promote well-ordered trimer formation and increased well-ordered trimer yields. Fractions collected after Lectin+SEC purification corresponding to the trimer elution volumes were examined by BN gel electrophoresis. The TD modified trimers displayed more favorable SEC profiles and deeper intensity trimer bands producing higher trimer yields.
Figure 4:
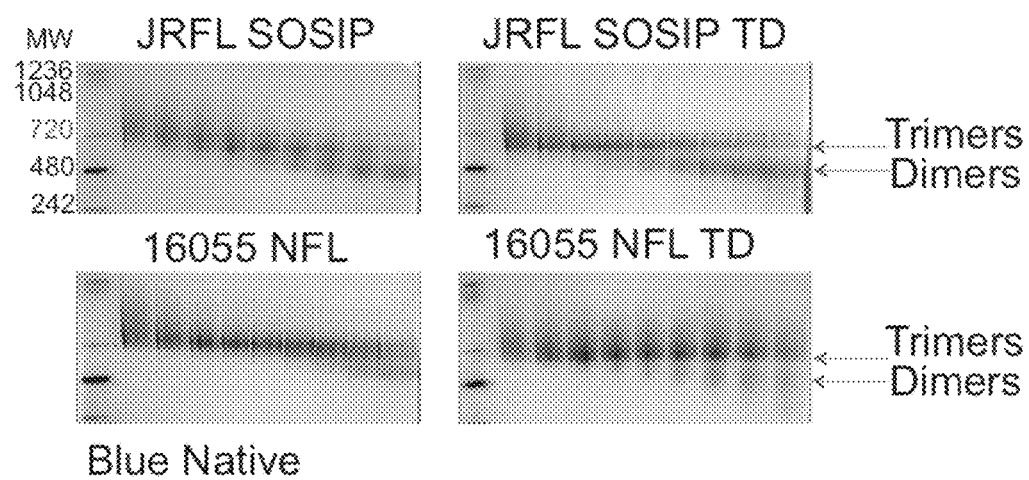

FIGS. 3 and 4 show TD mutations promote well-ordered trimer formation and increased well-ordered trimer yields. Fractions collected after Lectin+SEC purification corresponding to the trimer elution volumes were examined by BN gel electrophoresis. The TD modified trimers displayed more favorable SEC profiles and deeper intensity trimer bands producing higher trimer yields.

Figure 5A:
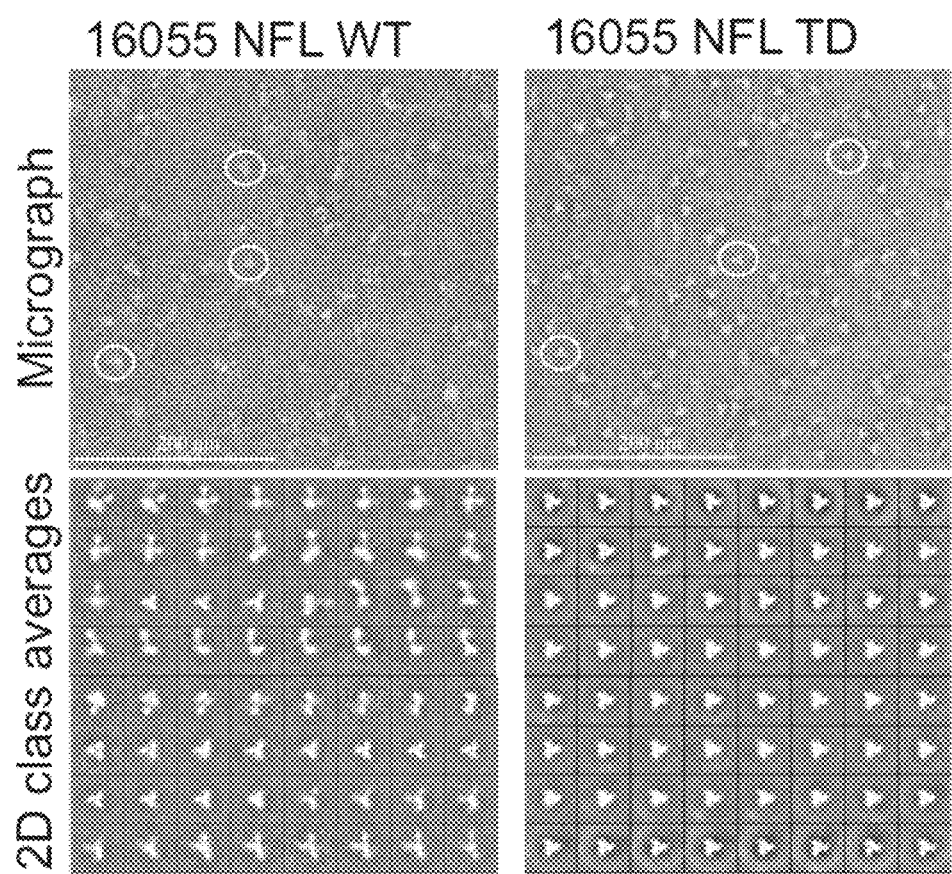
FIGS. 5A and 5B show TD mutations drastically reduce or eliminate the need for negative selection. JRFL SOSIP and 16055 NFL require a purification protocol consisting of three steps: lectin affinity, size-exclusion chromatography, followed by a final negative selection step where aggregates and/or dimers are eliminated. EM analysis of trimer samples after SEC suggests that the TD versions do not need to be negatively selected.
Figure 5B:
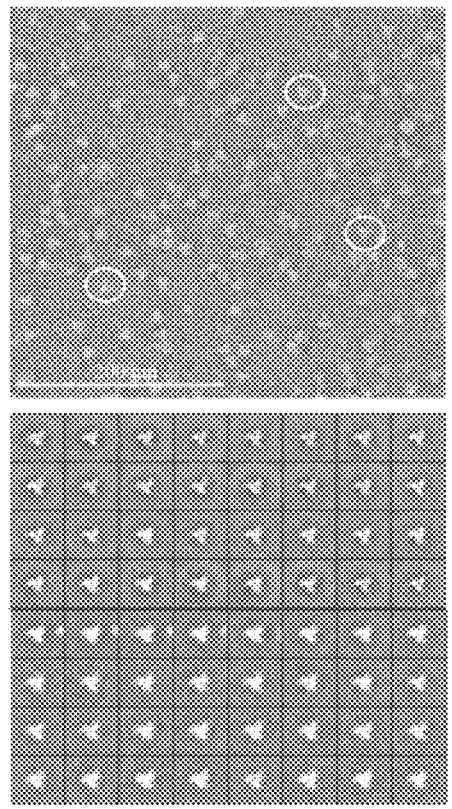

FIGS. 5A and 5B show TD mutations drastically reduce or eliminate the need for negative selection. JRFL SOSIP and 16055 NFL require a purification protocol consisting of three steps: lectin affinity, size-exclusion chromatography, followed by a final negative selection step where aggregates and/or dimers are eliminated. EM analysis of trimer samples after SEC suggests that the TD versions do not need to be negatively selected.

Figure 6:
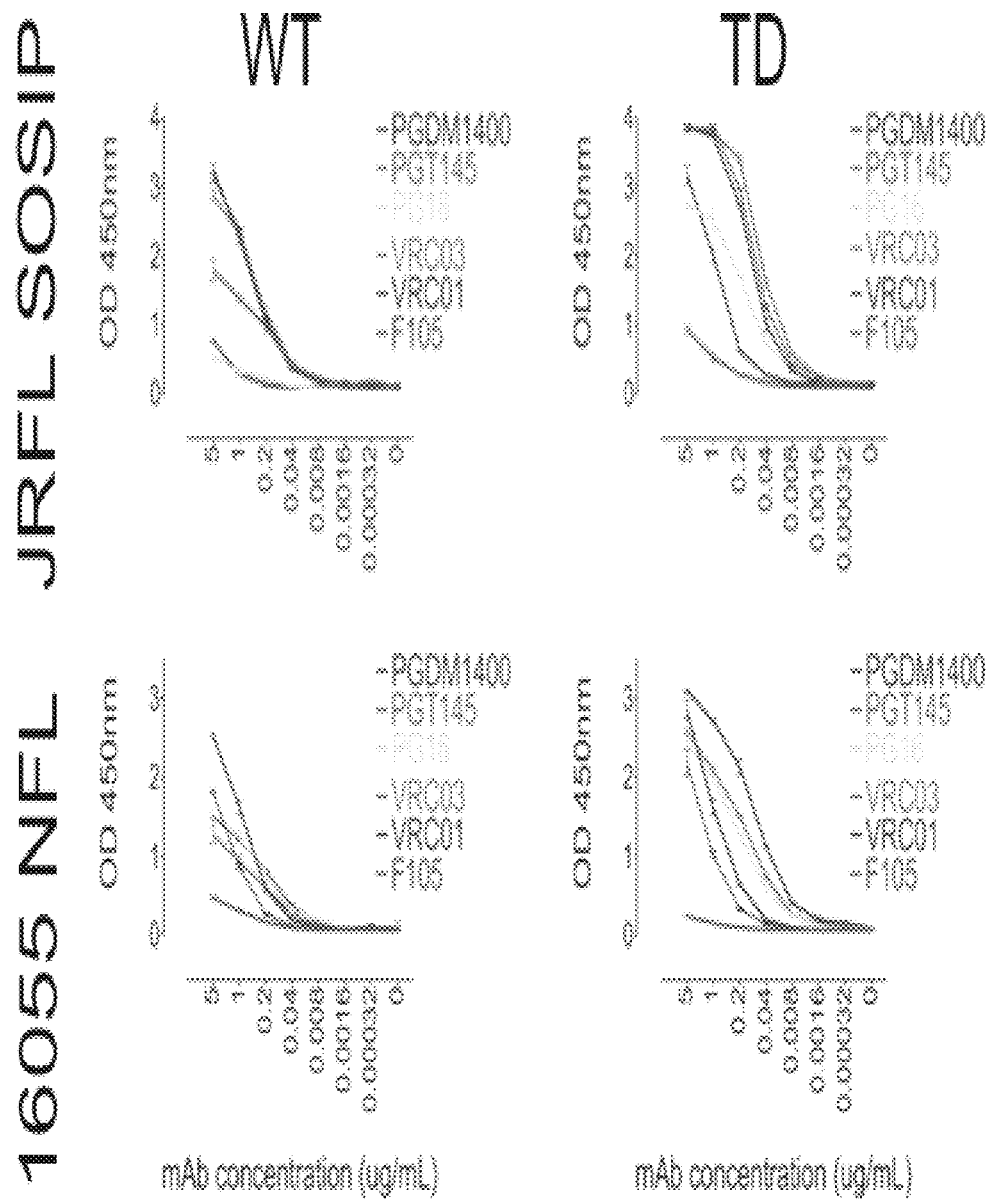
FIG. 6 shows TD mutations generate a more favorable antigenic profile in the absence of negative selection.

FIG. 6 shows TD mutations generate a more favorable antigenic profile in the absence of negative selection.

Figure 7:
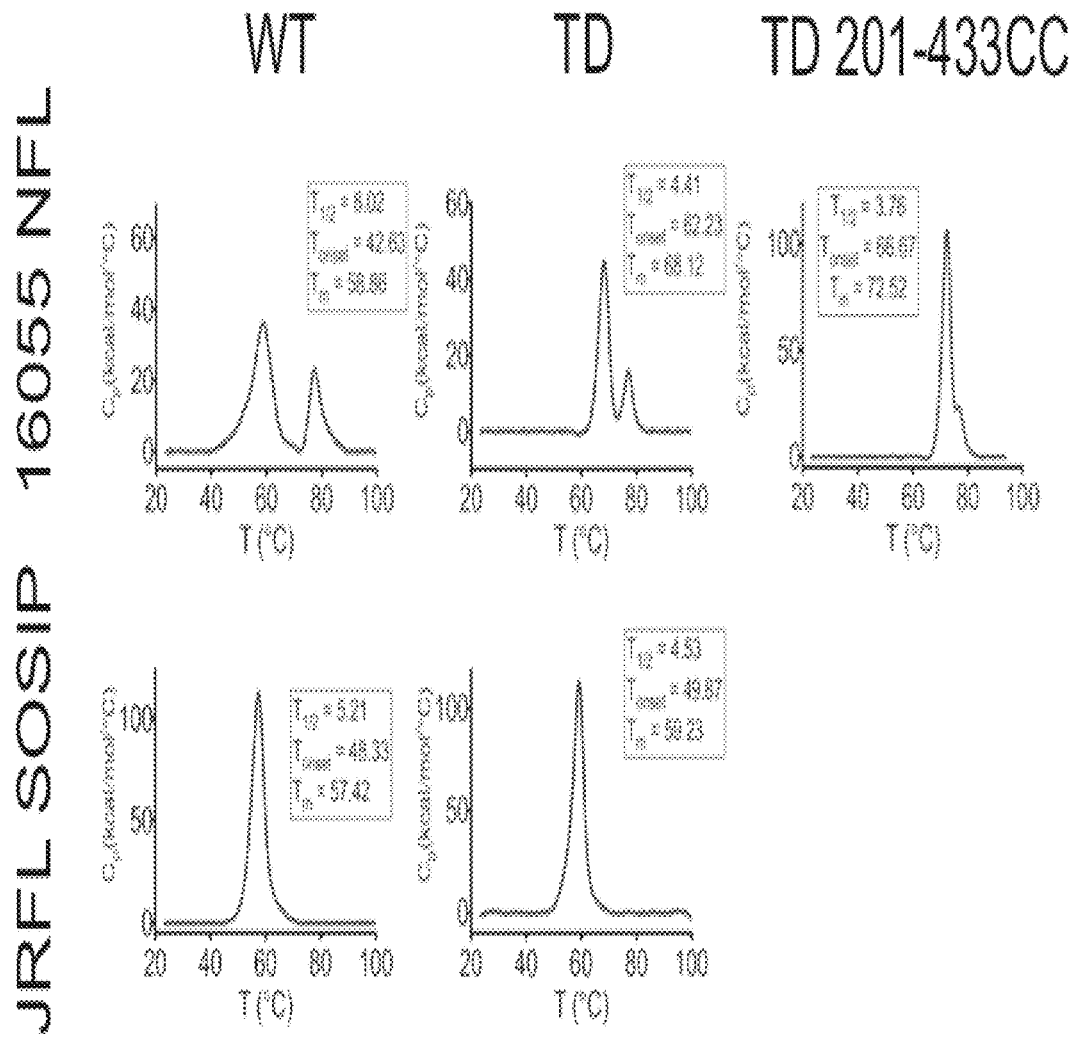
FIG. 7 shows TD mutations increased the thremostability of the trimers as measured by DSC.

FIG. 7 shows TD mutations increased the thremostability of the trimers as measured by DSC.

Figure 8:
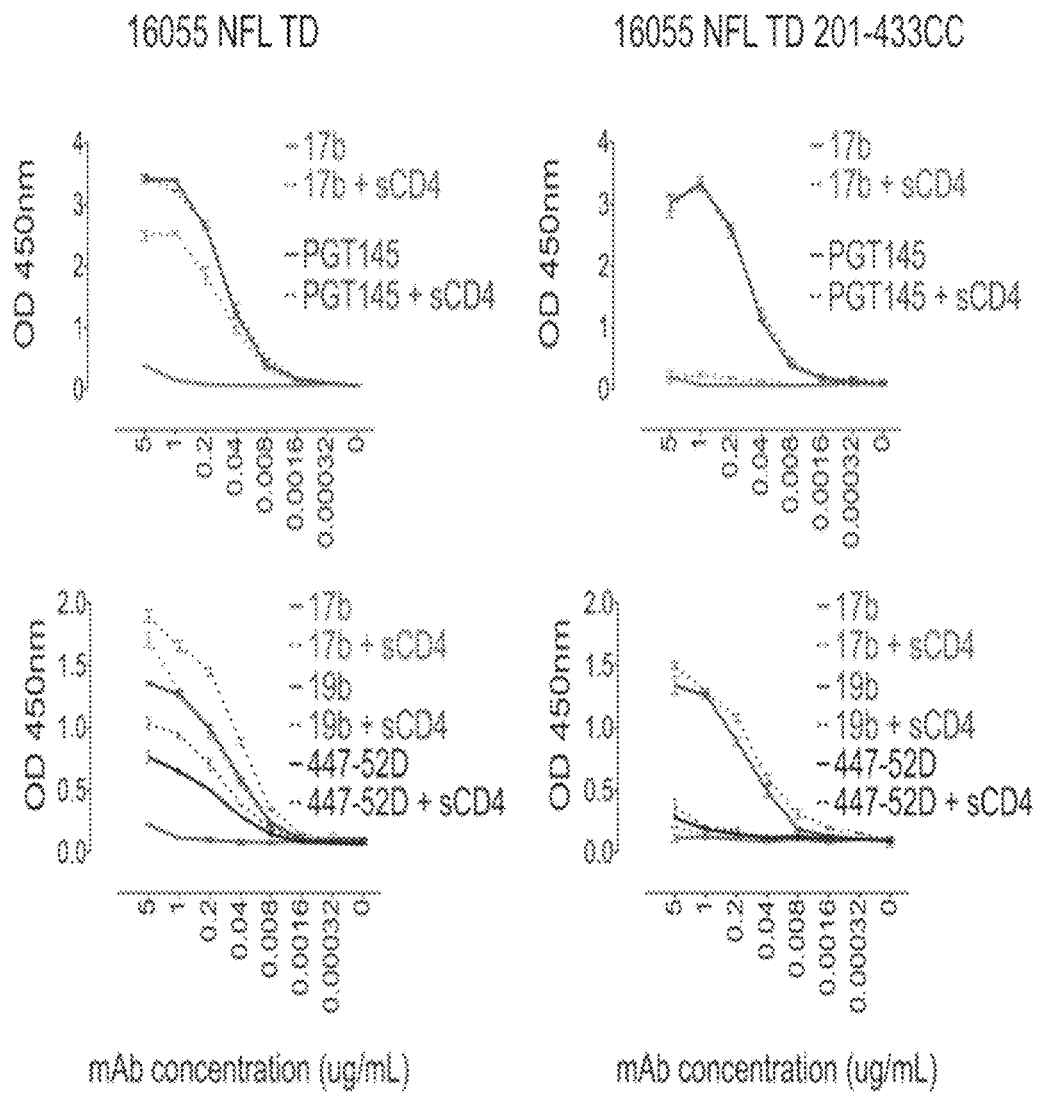
FIG. 8 shows a disulfide bridge linking residues 201-433 (β3 and β21) in addition to the TD mutations locks the pre-fusiogenic state of Env in 16055 NFL TD 201-433CC.

FIG. 8 shows a disulfide bridge linking residues 201-433 (β3 and β21) in addition to the TD mutations locks the pre-fusiogenic state of Env in 16055 NFL TD 201-433CC.

Figure 9:
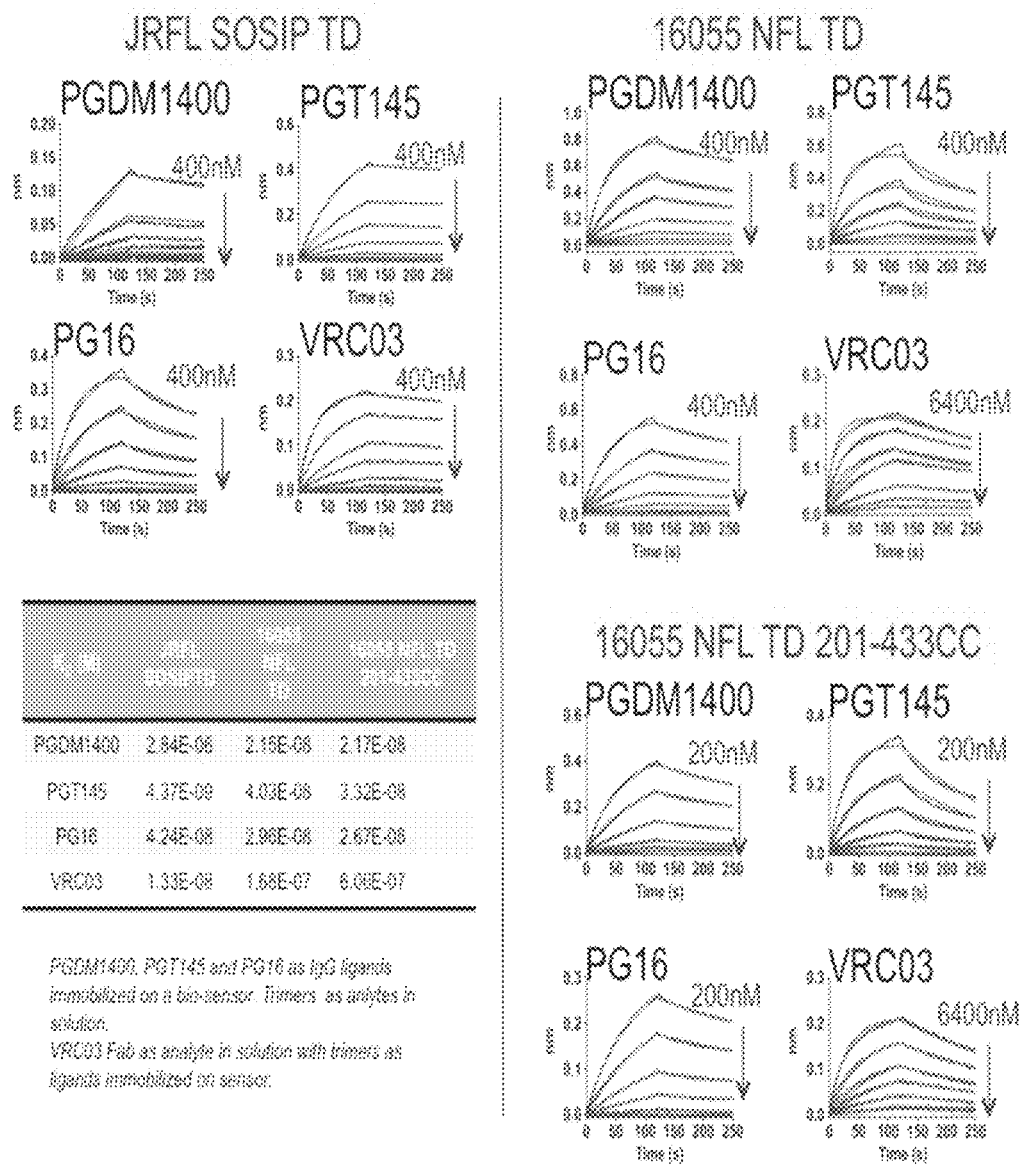
FIG. 9 shows trimer-preferred antibodies bind the TD trimers with a range of affinities.
Figure 10:
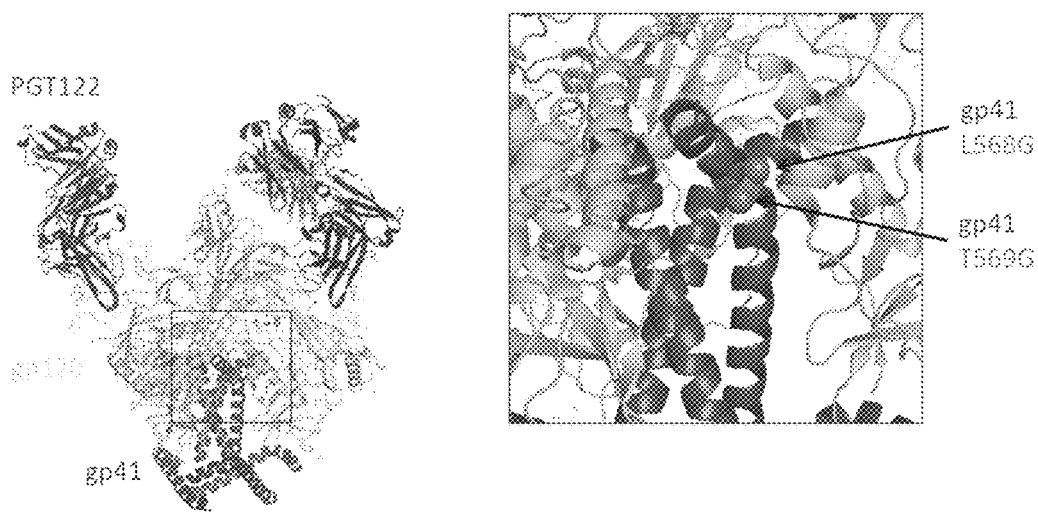
FIG. 10 depicts destabilization of HR1 gp41 to lock Env-based soluble trimers in the ground native-state.
Figure 11:
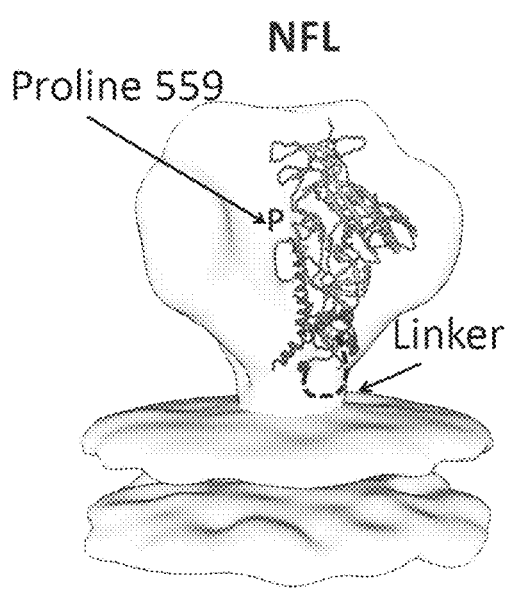
FIG. 11 depicts design details of the test trimer: 16055 NFL TD GL.
Figure 12:
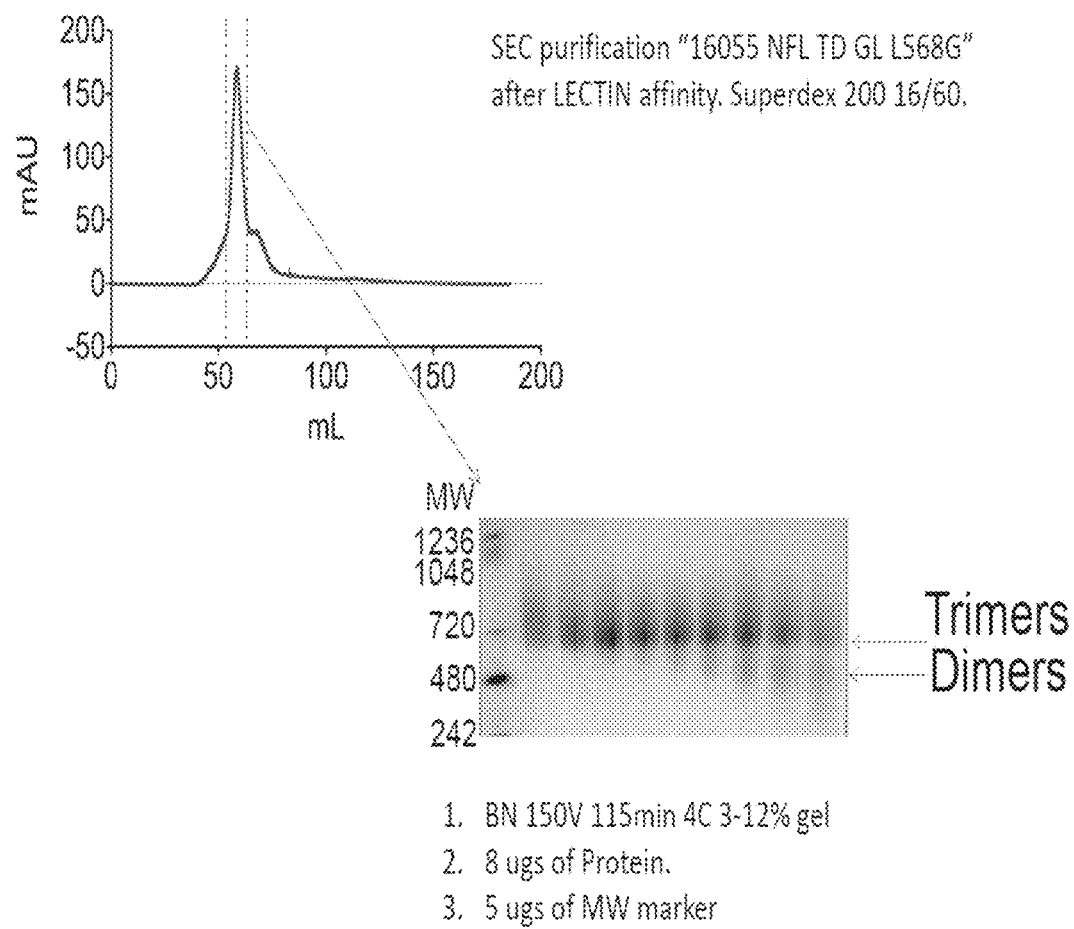
FIG. 12 depicts a biochemical characterizations of 16055 NFL TD GL.
Figure 13:
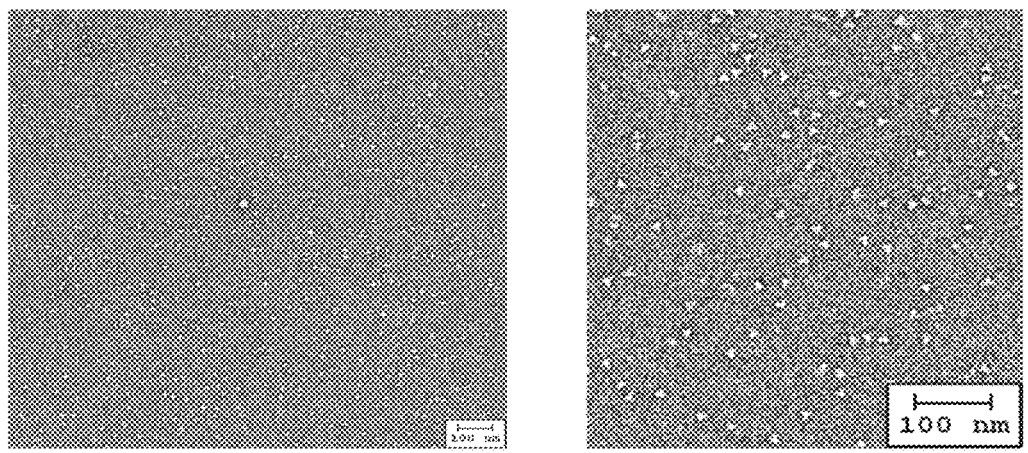
FIG. 13 depicts a biochemical characterizations of 16055 NFL TD GL: EM.
Figure 14:
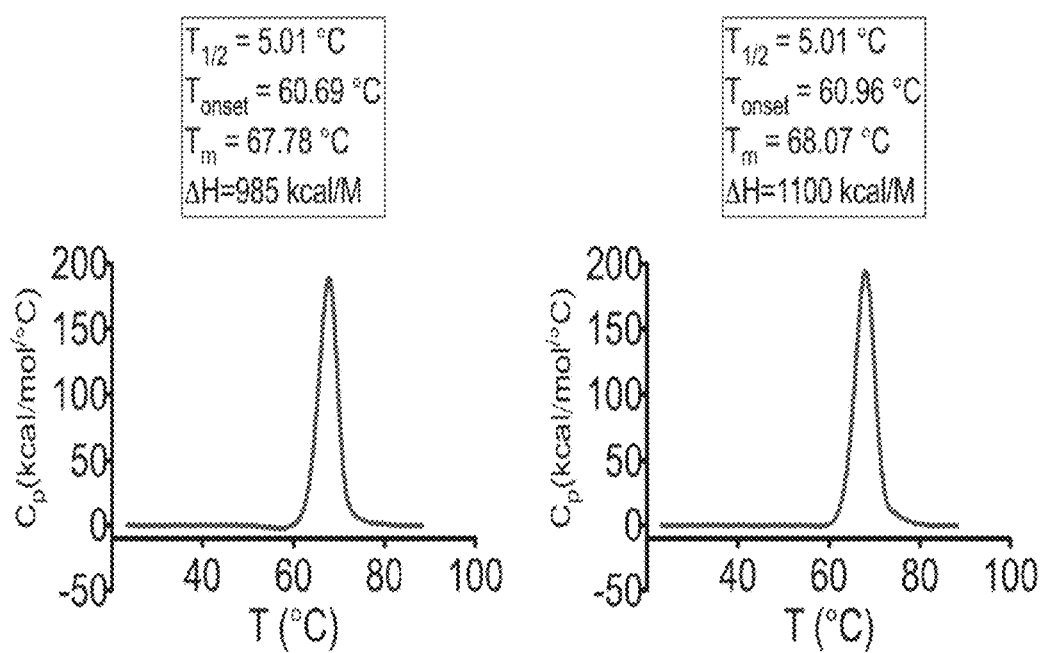
FIG. 14 depicts a biochemical characterization of 16055 NFL TD GL: DSC.
Figure 15:
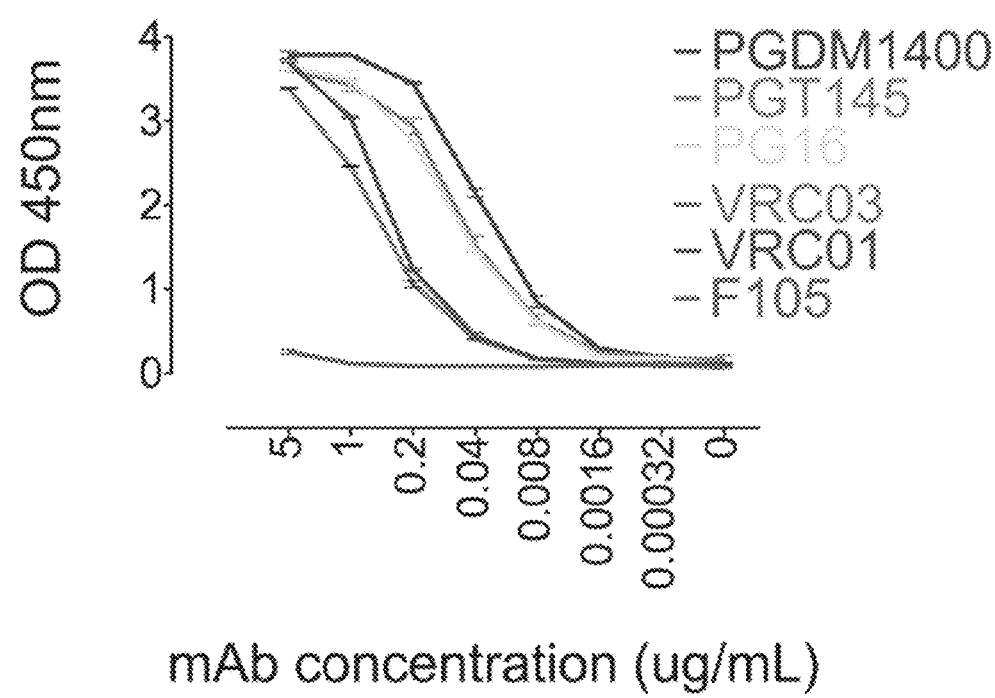
FIG. 15 depicts a biochemical characterization of 16055 NFL TD GL: ELISA.
Figure 17:
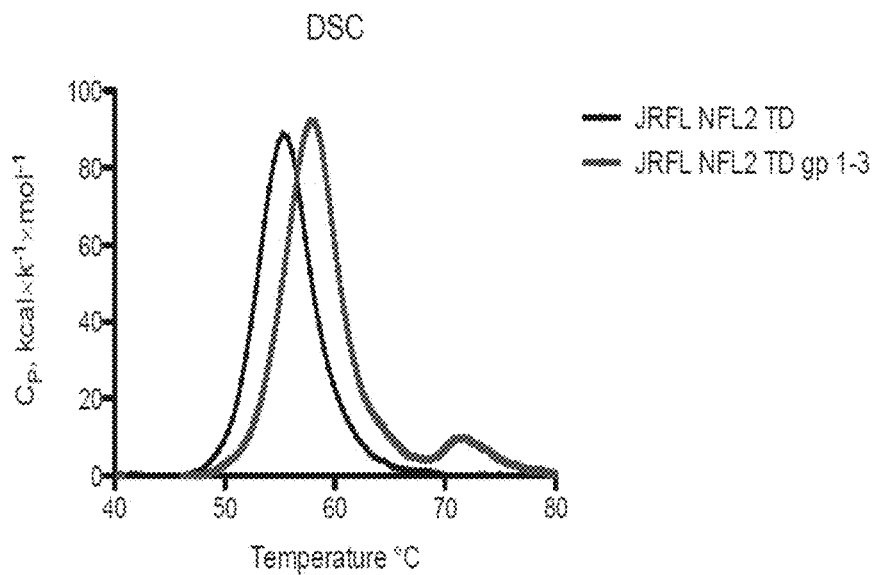
FIG. 17 depicts DSC data for JRFL NFL2 TD plus three stabilizing mutations in gp41 (L543N, Q567K and G588R).
Figure 19:
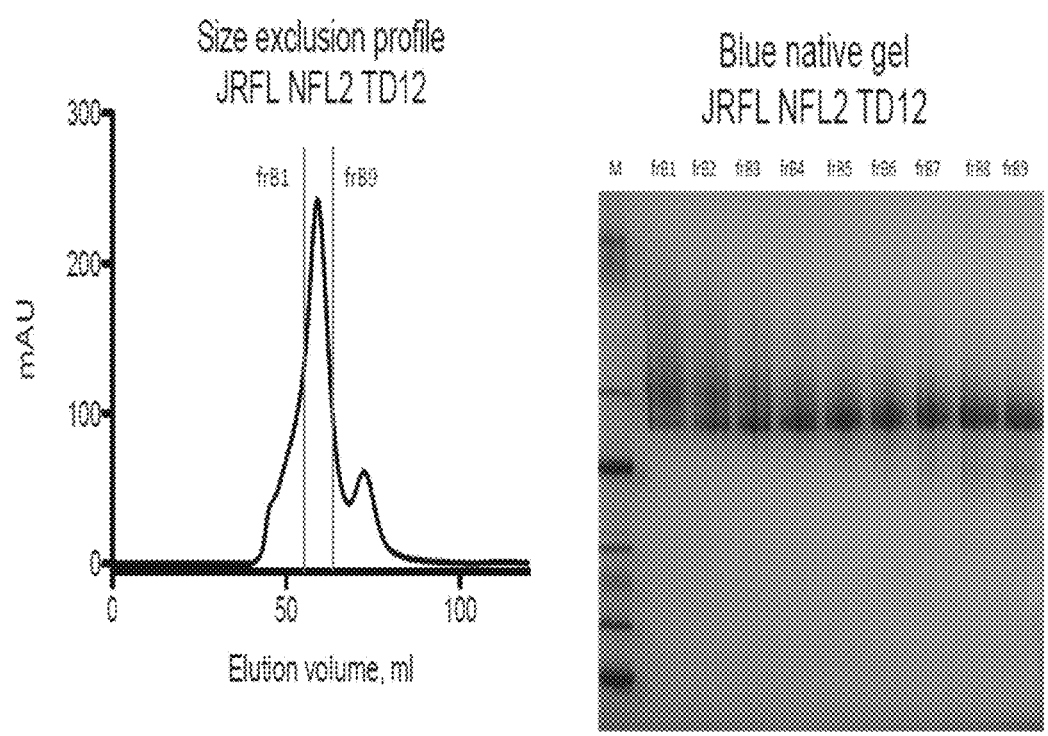
FIG. 19 depicts a size exclusion profile and blue native gel for JRFL NFL2 TD12.
Figure 20:
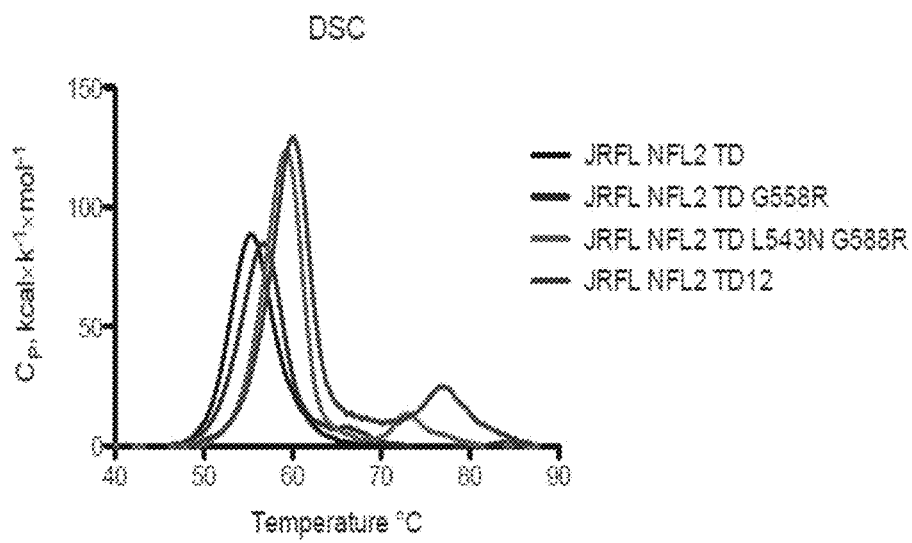
FIG. 20 depicts DSC data for JRFL NFL2 TD, JRFL NFL2 TD 6558R, JRFL NFL2 TD L543N G588R and JRFL NFL2 TD12.

FIG. 9 shows trimer-preferred antibodies bind the TD trimers with a range of affinities.

Without being bound by limitation, Applicants believe that TD mutations may strengthen the interaction between gp120 and gp41, increasing trimer formation.

Applicants believe that the glycine changes may lower the activation potential of the gp41 (and Env) to change conformation, and therefore results in better behaved trimers in a lower energy well from the "activation state" to spring to the next conformation. In a simple model, gp41 is essentially spring-loaded and constrained by gp120 until receptor binding. These mutations may contribute to reducing the springiness.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or specification.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J. Virol. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry. 1982 Sep. 28; 21(20):4839-43; Brayer & McPherson, J Biol Chem. 1982 Apr. 10; 257(7):3359-61; McPherson & Weickmann, J Biomol Struct Dyn. 1990 April; 7(5):1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates; providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silica" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG 16, and/or changes the conformation of a neutralizing antibody, such as PG9 or PG16. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

$F(ab')_2$, the fragment of the antibody that can be obtained by treating whole antibody with the enzyme pepsin without subsequent reduction; $F(ab')_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST(Washington University BLAST) version 2.0 software. WU-BLAST version 2.0 executable programs for several UNIX platforms can be downloaded from Washington University's blast ftp server. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404;

6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof; buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524, 584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1: Increased Propensity of HIV Env to Generate Highly Stable Soluble Spike Mimics by Structure-Based Design Due to high viral diversity, an effective HIV-1 vaccine will likely require Envs derived from multiple subtypes to generate broadly neutralizing antibodies (bNAbs). Soluble Env trimer mimetics, typified by the native, flexibly linked (NFL) and by the disulfide stabilized SOSIP derived from the subtype A BG505 Env, form highly homogeneous, well-ordered stable native-like trimers. However, other HIV-1 Env sequences, such as JRFL and 16055 from subtypes B and C, do so to a lesser degree, requiring negative selection to isolate the well-ordered trimer fraction. Here, Applicants identified BG505 trimer-derived (TD) residues that, when transferred, increased the propensity of the JRFL and 16055 Env sequences to form well-ordered, homogenous NFL trimers. Applicants further stabilized the NFL TD trimers by engineering an intra-protomer disulfide linkage in the pre-bridging sheet, I201C-A433C (CC) that locks the gp120 in the receptor non-triggered state. This disulfide pair prevented CD4 induced-conformational rearrangements. Coupling the TD modifications with the engineered disulfide linkage CC increased the propensity of Env to form soluble highly stable spike mimetics that can be used to test the hypothesis that such trimers will more efficiently elicit neutralizing antibodies.

The HIV-1 envelope glycoproteins (Env), which sparsely decorate the viral surface, are the sole target of host-elicited broadly neutralizing antibodies (bNAbs). A robust antibody response to Env will likely be required to generate a broadly effective HIV vaccine. To generate Env-specific neutralizing antibody responses, soluble mimetics have been developed with the objective of recapitulating the viral spike as candidate immunogens. Soluble mimetics of Env are difficult to produce in large part due to the labile nature of the normally non-covalent interaction between gp120 and gp41 subunits (Earl et al., 1994; Earl et al., 2001; Forsell et al., 2005; Gao et al., 2005; Kovacs et al., 2014; Spearman et al., 2011; Srivastava et al., 2003; Yang et al., 2000a; Yang et al., 2000b; Yang et al., 2002; Yang et al., 2001). However, Env modifications stabilize subunit interactions by engineered disulfides, resulting in the so-called SOSIP.664 trimers. These trimers are well-ordered native spike mimetics, requiring cleavage for proper quaternary packing (Binley et al., 2000; Binley et al., 2002; Sanders et al., 2013; Sanders et al., 2002). The recent high-resolution structure of the BG505 SOSIP trimer reinvigorated efforts to develop an HIV vaccine as it elicits tier 2 neutralizing serum antibodies in preclinical models (Bartesaghi et al., 2013; Do Kwon et al., 2015; Julien et al., 2013; Lyumkis et al., 2013; Pancera et al., 2014; Sanders et al., 2015). Applicants developed two other SOSIP trimers, the HIV subtype B JRFL- and subtype C 16055-derived trimers which require negative selection to yield homogenous, well-ordered trimers (Guenaga et al., 2015) and other clade B SOSIPs is also now available B41 (Pugach et al., 2015). Subsequently, Applicants designed a different means to covalently link the subunits, creating cleavage-independent Native Flexibly Linked (NFL) trimers which do not require precursor cleavage. The NFL trimers display a native-like conformation while obviating the need for cleavage by cellular furins required by the SOSIP trimers (Sharma et al., 2015).

BG505, JRFL and 16055 NFL and SOSIP trimers increase the expanding arsenal of soluble Env mimetics to assess immunogenicity in vivo as preclinical vaccine candidates. BG505-derived NFL and SOSIP designs form highly homogeneous and thermostable trimers that are purified by an initial affinity step (lectin or antibody), followed by size-exclusion chromatography (SEC) (Sanders et al., 2013; Sharma et al., 2015). JRFL- and 16055- or B41-derived trimers, however, are less homogenous and require negative or positive selection to generate trimer homogeneity (Guenaga et al., 2015; Pugach et al., 2015; Sharma et al., 2015). In this study, Applicants used BG505 structural information and sequence alignments to obtain improved variants of the 16055 and JRFL uncleaved NFL trimer. Applicants demonstrated that substitution of selected residues defined by the BG505 SOSIP structure in the 16055 and JRFL NFL contexts generated more homogenous and thermostable trimers, comparable to that of the BG505 NFL or SOSIP. The transfer of these dispersed residues, overcame the need for negative selection, yielding subtype B and C well-ordered NFL trimers directly from the SEC profile. This analysis revealed three regions of stability of Env, the gp120-gp41 interface, the pre-bridging sheet and the V2/V3 interface. These improvements allowed us to add an additional element of trimer stability, an intra-protomer disulfide bond. This internal cysteine pair was designed to prevent primate CD4-induced conformational changes on the trimer, limiting exposure of non-neutralizing epitopes. It does so, while still generating well-ordered trimeric spike mimetics, especially in the 16055 context. The lack of CD4 induction is desirable as the well-ordered trimers advance into preclinical testing in non-human primates, which possess CD4 that binds gp120 with high affinity (REFS). The properties of increased stability, along with furin-independence and increased yields, positions the improved NFL trimers for future clinical utility.

Disperse Env Elements Increase Stability of the NFL Trimers.

Figure 21A:
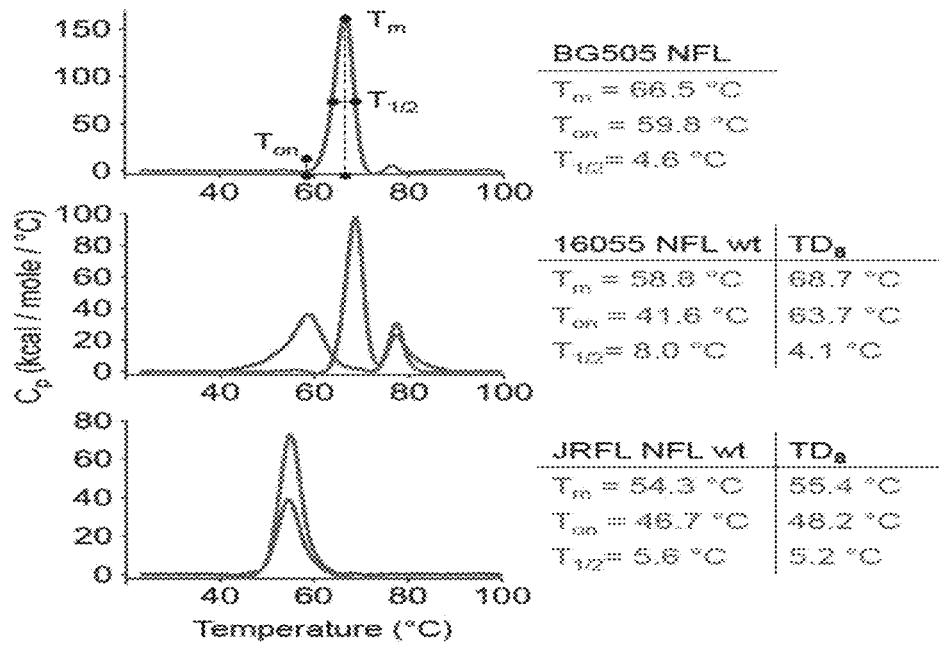
FIGS. 21A-B depicts thermostability and modifications of NFL trimers. (A) DSC analysis of NLF trimers before and after BG505-trimer derived (TD) substitutions. Clade A BG505, clade B JRFL and clade C 16055 NFL Wt DSC thermal transition curves are shown in blue while those corresponding to the NFL TD8 versions are shown in red. DSC parameters (Tm, Tonset, T1/2) are displayed next to the curves in corresponding colors. (B) Ribbon representation of the BG505 SOSIP structure (derived from PDB ID 4TVP) where gp120 is colored in green and gp41 in grey. Annotated with orange spheres are the eight BG505 TD residues located proximal to the trimer axis that were substituted in JRFL and 16055 NFL to make the TD8 variants. Red colored spheres represent residues identified in the sequence alignments but discarded due to their distant location from the trimer axis.

The BG505-Env derived NFL glycoprotein readily forms trimers that adopt a native-like conformation. These trimers can be purified in a two-step scheme of lectin affinity chromatography followed by size exclusion chromatography (SEC). JRFL and 16055 NFL trimers results in a mixture of native and aberrant trimers that are not resolved by this process and require the additional step of negative selection to remove aberrant trimers, contaminating monomers and dimers (Guenaga et al., 2015; Sharma et al., 2015). Consequently, yields of these trimers are lower than those of BG505 NFL trimers. Also, the JRFL and 16055 NFL trimers display inferior thermostability profiles in comparison to that of the BG505 NFLs, possessing lower thermal transition midpoints (Tm) (FIG. 21A). Applicants reasoned that the BG505 Env sequence contained elements of stability deficient in the other two Env sequences that increase the propensity to form well-ordered stable trimers in both the NFL and SOSIP platforms. By alignment of the three Env sequences BG505, JRFL and 16055 Applicants identified BG505 residues potentially involved in enhanced trimer formation. Applicants selected residues that differed for both 16055 and JRFL Env sequences from that of the BG505 Env sequence. Given the variability of Env sequences, this analysis yielded tens of residues. Annotating these differences in the context of the high-resolution structure of the BG505 SOSIP structure (Pancera et al., 2014), Applicants focused primarily on differences at or nearby the gp120: gp41 interface or trimer axis. Applicants reasoned that it was at the semi-conserved gp120-gp41 interface where the major elements of enhanced BG505 stability would likely reside due to the high diversity between all Envs in the variable regions. This approach allowed us to eliminate many hypervariable residues exposed on the surface of trimer, reducing the complexity of the analysis.

Figure 21B:
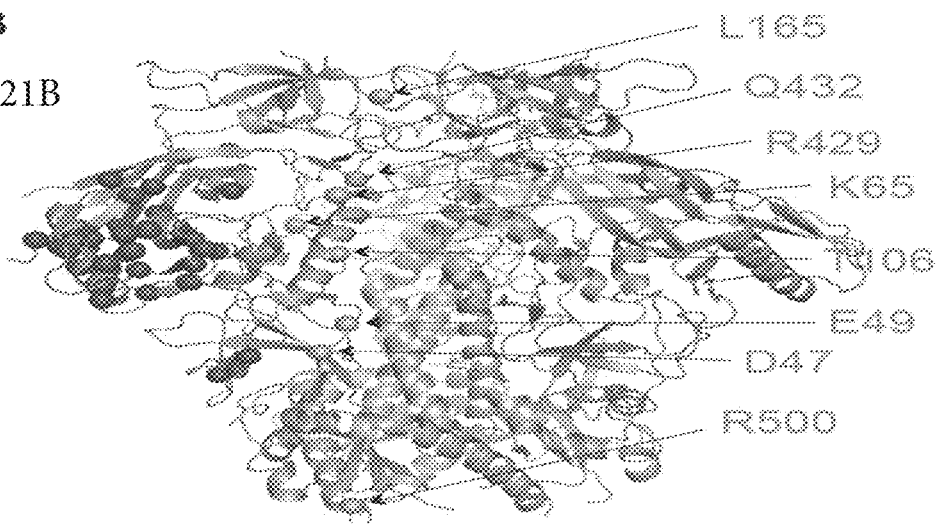

Applicants identified eight gp120 residues in the BG505 sequence: 47D, 49E, 65K, 106T, 165L, 429R, 432Q, 500R that differed in both JRFL and 16055. Applicants termed these amino acids "BG505 Trimer Derived (TD)" residues (FIG. 21B). Applicants transferred these eight residues (TD8) as a full set to 16055 and JRFL NFL coding sequences and evaluated their impact on trimer formation and stability. Following lectin affinity and SEC purification, Applicants assessed stability of the engineered 16055 and JRFL NFL "TD8" variant trimers by differential scanning calorimetry (DSC), revealing positive effects on stability. For the 16055 NFL trimers, the selected TD8 mutations increased the Tm of the 16055 NFL trimers from the unmodified wild-type (wt) trimers of 58.8° C. to 68.7° C. The latter value now actually exceeds that of the BG505 NFL trimer (66.5° C.). The effect of these mutations on Tm was less significant for the JRFL Env-derived NFL TD8 trimers (54.3° C. to 55.4° C.). Other DSC parameters, such as the width of the thermal transition at half height of the DSC peak (T1/2) and the melting starting onset temperature (Ton), also improved for the NFL TD8 variants in comparison with the parental wt variants (FIG. 21A). A lower T1/2 is associated with increased molecular homogeneity and a higher Ton indicates increased resistance of the trimer to disassemble.

Figure 22A:
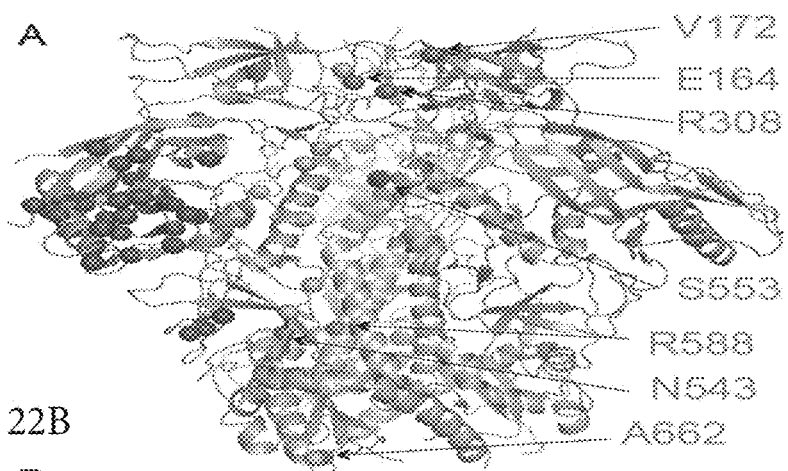
FIGS. 22A-C depicts additional TD modifications and thermostability of JRFL NFL variants. (A) Additional TD substitutions beyond the original TD8 residues in orange are annotated as blue spheres in the BG505 SOSIP structure (PDB ID 4TVP). A total of fifteen residues were transferred from the BG505 envelope sequence to the JRFL NFL trimer to make the more stable TD15 trimer variant. (B) DSC thermal transition curves and derived parameters of the JRFL HIV-1 sequence derived NFL trimers, Wt in blue, TD8 in red and TD15 in green show a progressive amelioration of the JRFL NFL trimer thermal stability. (C) BG505-trimer derived (TD) residues transferred to the JRFL and 16055 HIV sequences to make the more stable NFL TD variant trimers identify three regions of HIV envelope glycoprotein stability, the variable region V2/V3 colored in lavander, the pre-bridging sheet in teal and the gp120-gp41 interface in brown.
Figure 22B:
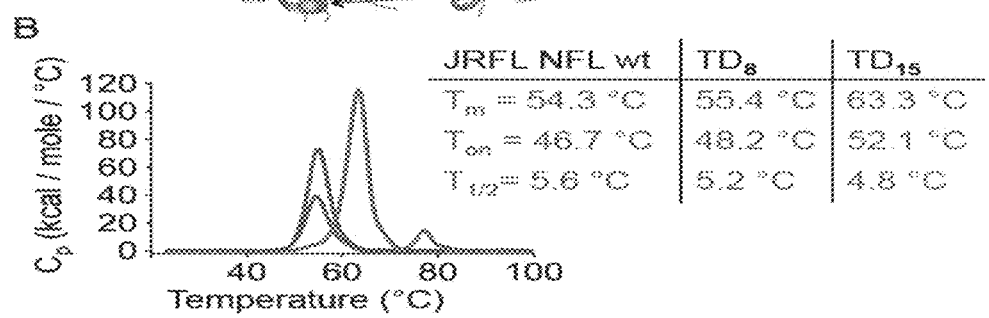
Figure 22C:
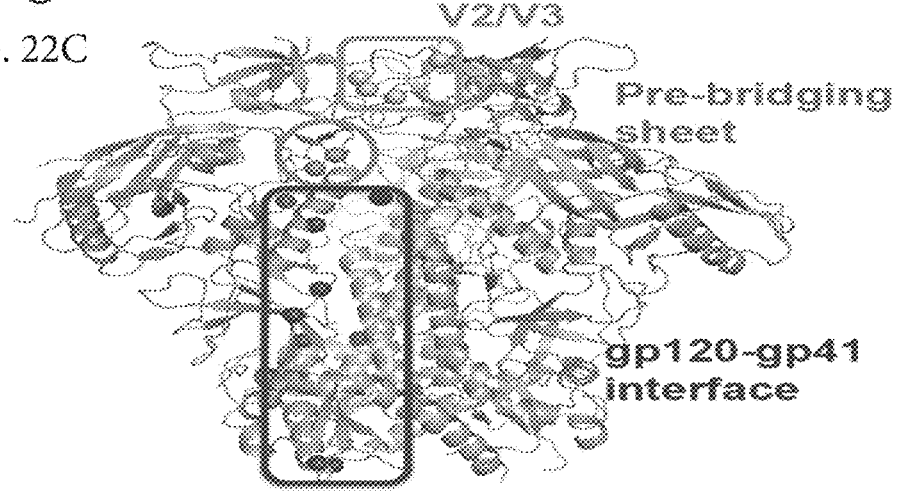
Figure 28:
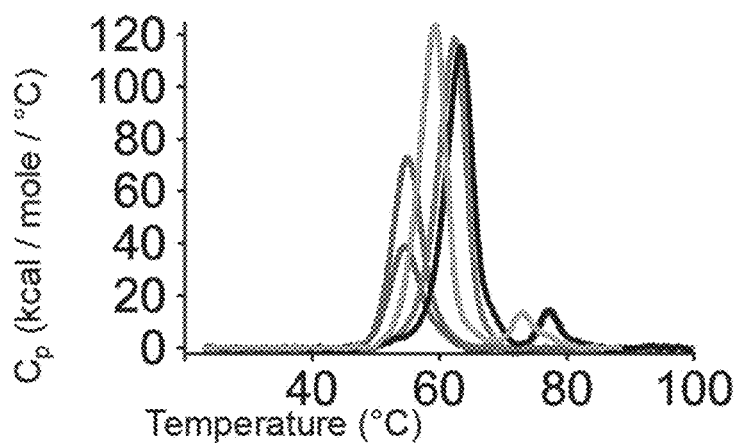
FIG. 28 depicts stability of JRFL NFL trimer variants by DSC. DSC thermal transitional curves corresponding to the JRFL NFL wt (blue), TD8 (red), TD12 (orange), TD14 (green) and TD15 (black) and corresponding derived DSC parameters.

Since the stability of 16055-derived trimers, but not that of the JRFL-Env derived trimers, reached that of the reference BG505-Env derived trimers, Applicants reasoned that there might be additional elements of Env stability that remained to be identified from Applicants' first screen that might further improve the JRLF NFLs. By now comparing the JRFL to the composite 16055 and BG505 Env sequences, Applicants identified additional residues that potentially contribute to the superior stability of both BG505 and 16055 TD8 NFL trimers relative to those derived from JRFL. These newly identified residues were located in gp41, at the gp41-gp120 interface (543N, 553S, 588R and 662A) and in the variable cap loops of gp120 (164E, E172V and 308R). Applicants transferred a total of fifteen residues from BG505/16055 to JRFL to generate JRFL NFL "TD15". These modifications included the original gp120 TD8 residues and the seven newly identified gp41/variable region cap residues (FIG. 22A). DSC analysis of the newly generated JRFL NFL TD 15 trimers revealed a considerable enhancement of stability as Tm increased from 54.3° C. to 63.3° C. with the newly identified residues, consistent with their overall contribution to increased JRFL NFL TD 15 stability (FIG. 22B). Along the pathway to TD15 design, Applicants also generated intermediate TD12 and TD14 variants which demonstrated step-wise ordered trimer stability (FIG. 28A). When interpreted in the context of the SOSIP high resolution structure, the TD residues clustered in three distinct, but disperse regions of Env, the gp120-gp41 interface (47, 49, 65, 106, 500, 543, 553, 588, 662), the variable loops (164, 165, 172, 308) and, as well, the pre-bridging sheet (429, 432) (FIG. 22C). The bridging sheet substitutions suggested additional modifications in this latter region might further increase stability, which Applicants further investigated below.

TD Modifications Increased NFL Trimer Formation Propensity and Yields.

Figure 23:
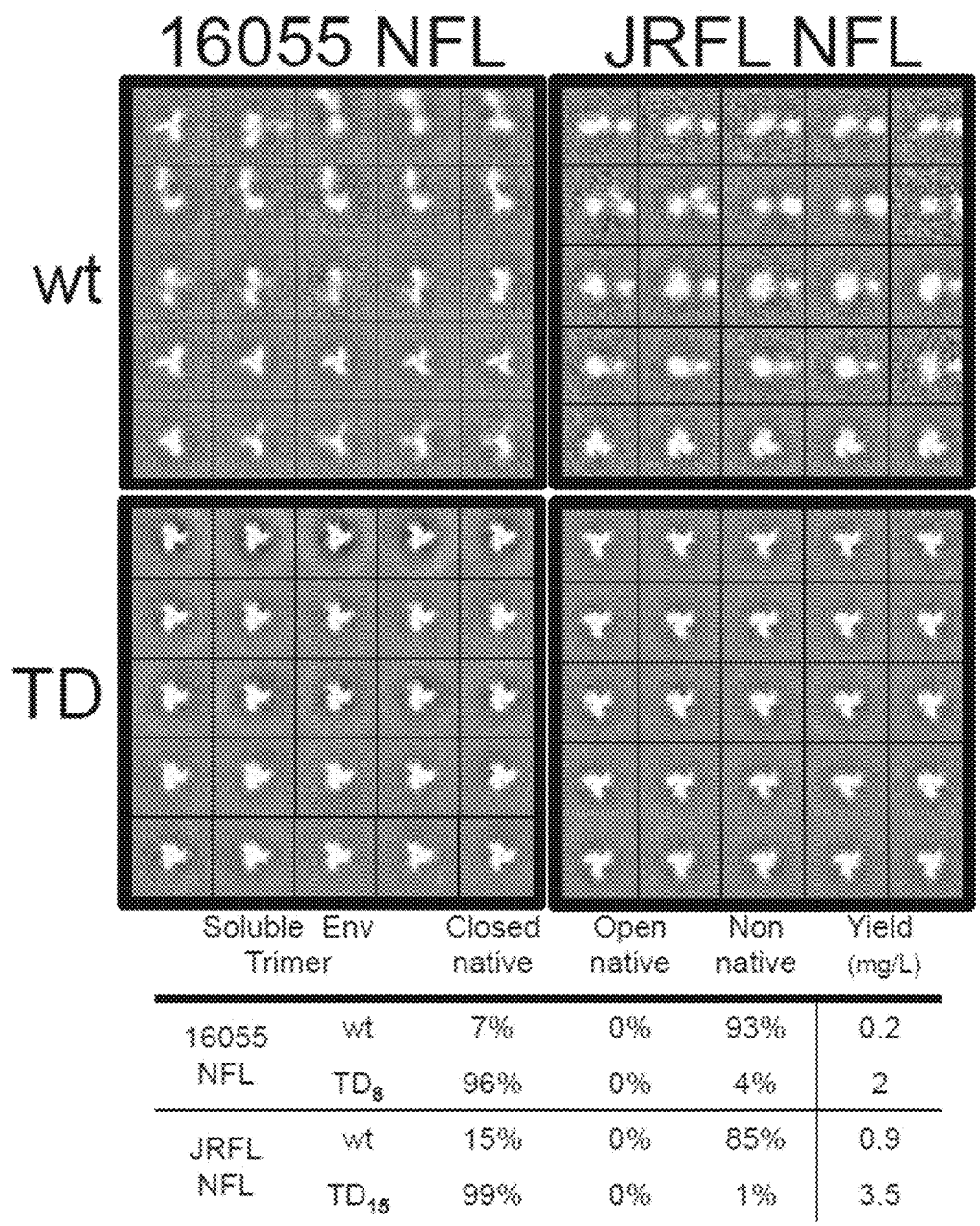
FIG. 23 depicts representative 2D-class averages of NFL trimers by Negative stain EM. Comparison of representative 2D-class averages of the 16055 and JRFL NFL Wt trimer (top panels) versus those corresponding to the TD variants (bottom panels) by NS-EM. Below the EM images are the corresponding calculated proportions of native trimers and non-native trimers and the final yields of protein in mg per liter of cells transfected.
Figure 29:
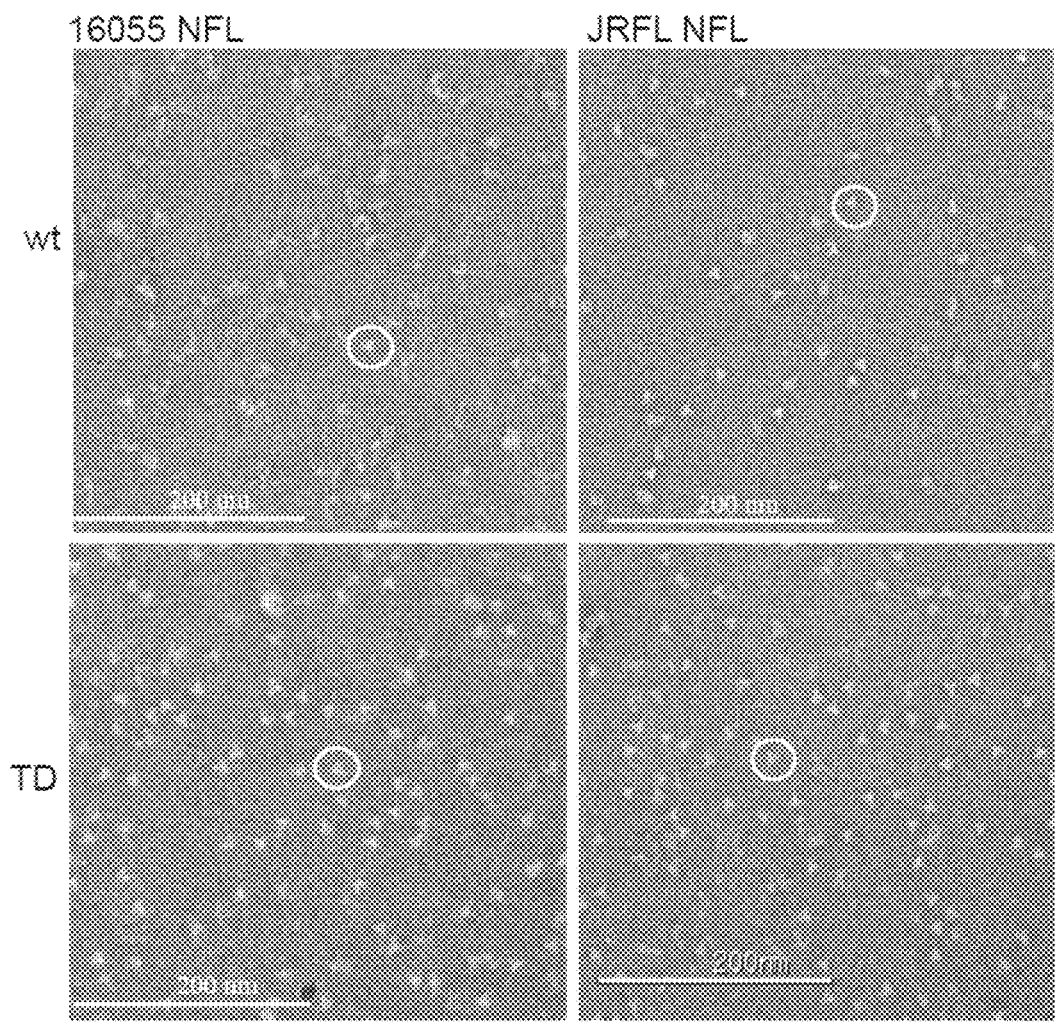
FIG. 29 depicts negative stain EM micrographs. Micrographs comparing 16055 NFL wt vs TD8 and JRFL NFL wt vs TD15.

Following lectin-affinity/SEC, Applicants investigated the conformational state of both unmodified (wt) and modified (TD) trimers by negative stain EM. Visual inspection of the EM micrographs of the Wt 16055 NFL trimers showed a preponderance of aggregates with the detection of few well-ordered trimers. Computational analysis of the EM micrographs revealed only 7% closed, native-like trimers. In contrast, analysis of the more stable 16055 NFL TD8s revealed well-ordered native-like trimers with counts exceeding 95% (FIGS. 23 and 29). Similarly, EM micrographs of the wt JRFL NFL trimers displayed a limited level of well-ordered trimers (~15%) whereas micrographs of the stabilized JRFL NFL TD 15 revealed a preponderance of well-ordered trimers, exceeding 95% (FIG. 23 and FIG. 29).

Figure 24:
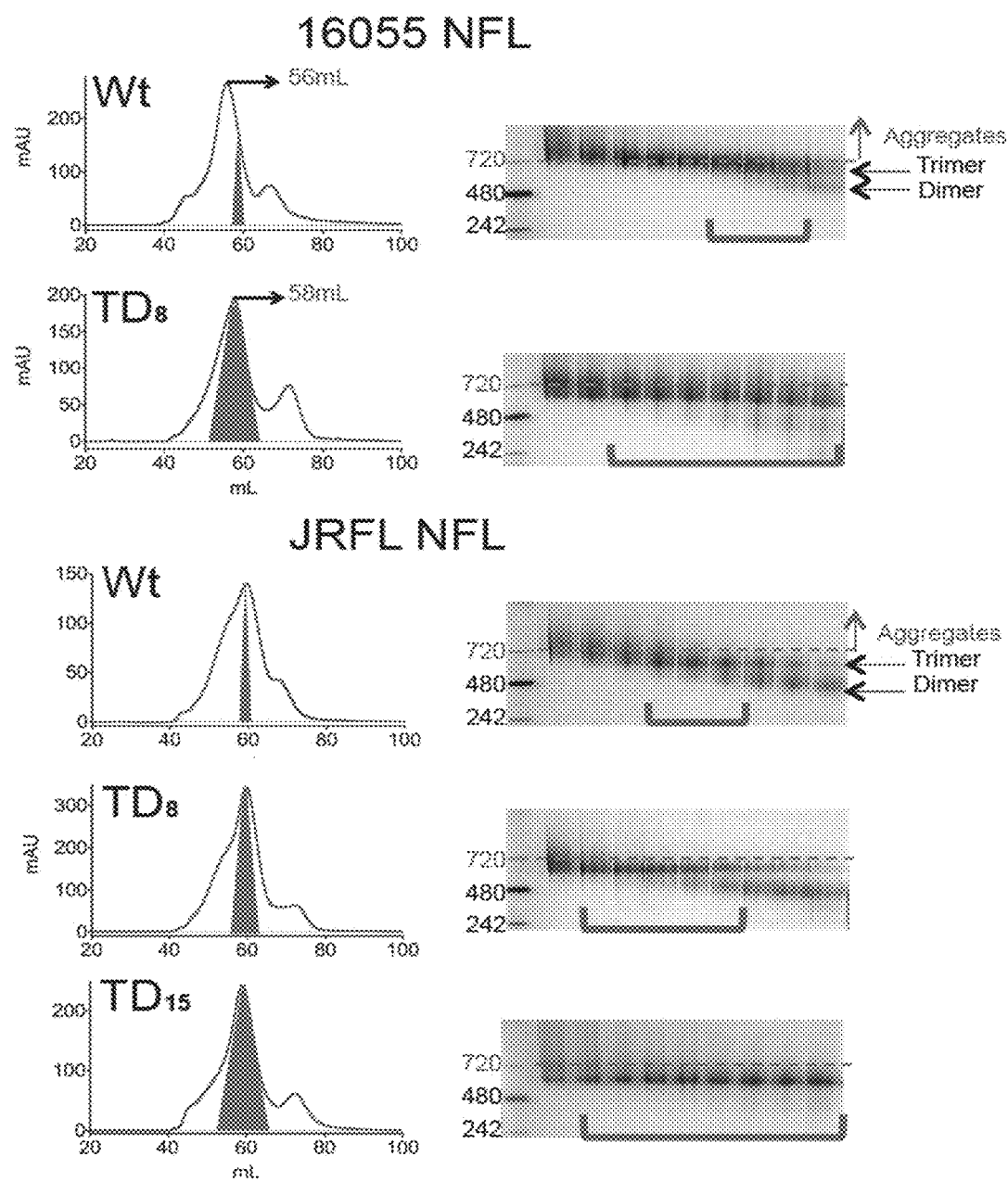
FIG. 24 depicts SEC profiles and BN gels of Lectin-affinity purified trimers. SEC profiles of letin-affinity purified Wt and TD 16055 NFL (top) and JRFL NFL (bottom) trimer variants. The shaded red area approximately defines the native-like trimer fractions noted with a red colored bracket in the BN gels.

By retrospective analysis, the enhanced propensity of the NFL TD variants to form well-ordered homogenous trimers as determined by DSC and EM was also manifested on SEC profiles and blue native (BN) gels of the trimer fractions collected during purification as follows. The wt 16055 NFL trimer peak normally is detected at 56 mls of the column volume. However, with the TD modifications the major peak elution volume shifted "to the right", from 56 to 58 mLs, indicating a smaller Stokes radius of the TD trimers (FIG. 24). The collected SEC trimer fractions were analyzed by BN gel electrophoresis where the smaller molecular mass was corroborated. While the wt 16055 NFL protein showed a preponderance of bands at a higher molecular weight aggregates (~720 kD) the TD8 variant displayed a majority of bands at the expected molecular size of a well-ordered trimeric soluble Env mimic (~640 kD) (FIG. 24). Similarly, a narrower SEC trimer peak was observed for the final JRFL NFL TD15 variant, suggesting an increased propensity to form homogenous trimers as computed by the EM analysis (FIGS. 23 and 24). Accordingly, BN gels revealed a decreased in aggregate, dimer and monomer bands with the full set of TD15 mutations (FIG. 24). Overall, the EM negative stain analysis, SEC profiles and BN gels indicated that the TD trimer variants were conformationally more homogeneous and native-like than the parental wt versions. This general improvement in trimer homogeneity and stability indicates that the TD mutations increased the propensity of 16055 and JRFL Env to form well-ordered trimers, favorably increasing final trimer yields (FIG. 23).

TD Trimers are Efficiently Recognized by bNAbs but not by Non-Neutralizing Antibodies.

Figure 25A:
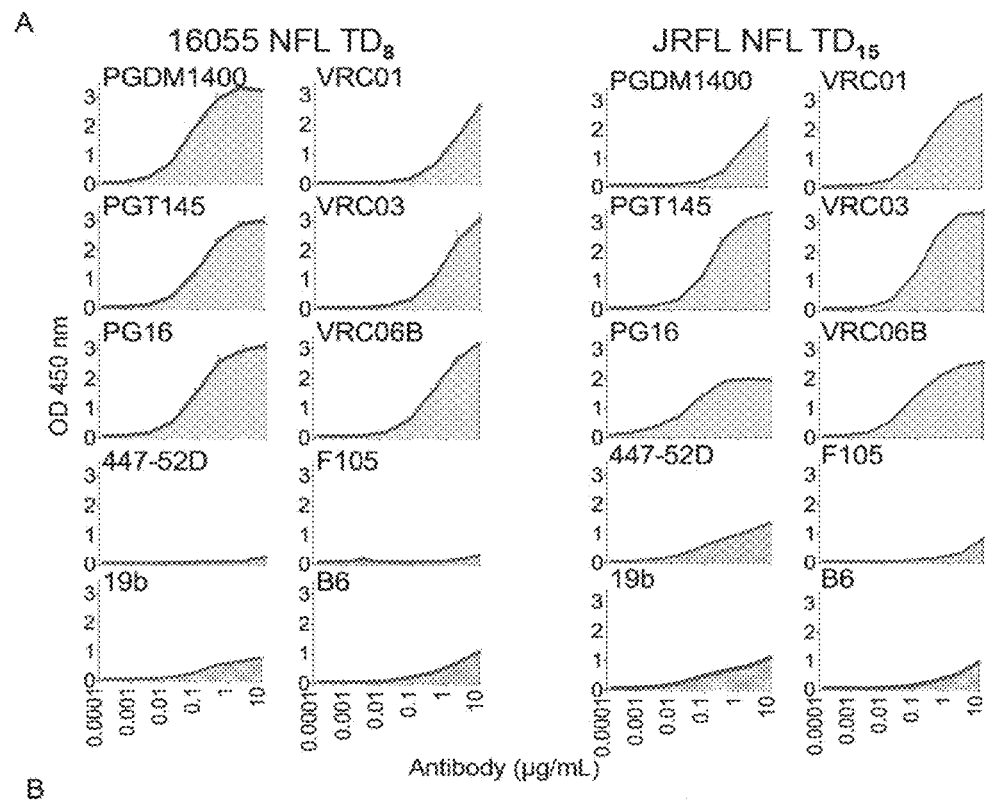
FIGS. 25A-B depicts ELISA and Octet binding of selected antibodies to the NFL TD trimers. (A) ELISA binding of selected bNAbs (in blue) and Non-NAbs (in red) targeting the Variable cap and CD4bs envelope glycoprotein regions to 16055 NFL TD8 (left) and JRFL NFL TD15 (right) trimers purified by lectin-affinity followed by SEC. (B) Kinetic parameters derived by bio-layer light interferometry using three trimer-preferred bNAbs as analytes and the NFL TD trimers as ligands.
Figure 30:
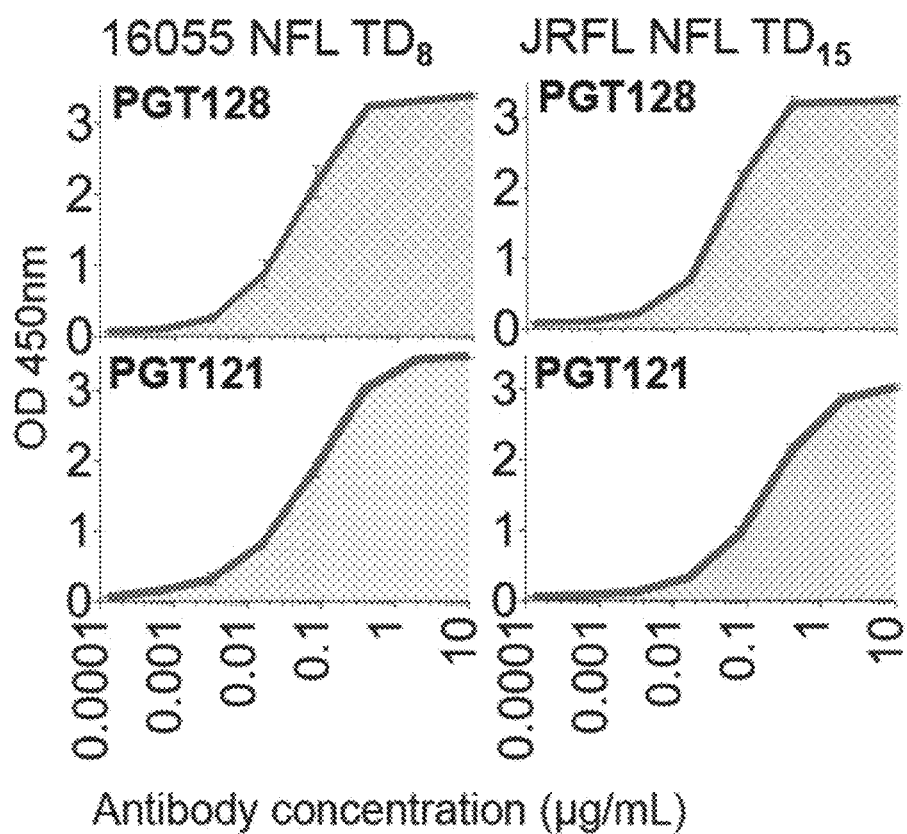
FIG. 30 depicts trimer recognition of selected N332-targeting bNAbs. ELISA binding curves corresponding to the N332-supersite targeting bNAbs PGT128 and PGT121 recognizing the 16055 NFL TD8 and JRFL NFL TD15 trimers.

Following EM and DSC analysis Applicants sought to verify that the favorable antigenic profile of the well-ordered trimers was maintained following the TD modifications. Anti-HIV Env antibodies targeting different regions of Env provide valuable information about the quaternary conformation of the soluble trimers as demonstrated in several recent studies (Blattner et al., 2014; Do Kwon et al., 2015; Georgiev et al., 2015; Guenaga et al., 2015; Pugach et al., 2015; Sharma et al., 2015). The antibodies PGDM1400, PGT145 and PG16 are potent broadly neutralizing antibodies (bNAbs) targeting the variable cap of the spike and are considered to be "trimer-preferring" since they selectively bind the native spike and well-ordered native-like soluble trimers (Sok et al., 2014; Walker et al., 2011; Walker et al., 2009). Efficient recognition by the trimer-preferring antibodies indicates a native-like assembly of the soluble trimers. In contrast, the antibodies 447-52D and 19b, also targeting the variable cap V3 region, are considered non-neutralizing antibodies (non-NAbs) since they neutralize only HIV-1 tier 1A or 1B isolates that are not representative of most circulating clinical isolates. Efficient trimer binding by these antibodies is not desired since recognition likely indicates an open conformation of Env. Such global opening occurs in disordered trimers lacking proper quaternary packing. Or for full-length functional Env, or soluble, ordered trimers, in the CD4-triggered state. Similarly, at the conserved CD4 binding site (CD4bs), efficient recognition by the CD4-binding site-directed bNAbs, VRC01, VRC03 and VRC06b, is desired, as is inefficient binding by the non-neutralizing CD4bs-directed b6 and F015 mAbs (Li et al., 2012; Wu et al., 2010). Accordingly, Applicants performed ELISA binding avidity experiments to assess recognition of the NFL TD trimer variants by a panel of bNAbs and non-NAbs. Both 16055 NFL TD8 and JRFL NFL TD15 were well recognized by bNAbs and poorly recognized by non-NAbs at both the variable cap and the CD4b binding regions of Env (FIG. 25A). 16055 NFL TD8 was better recognized by the variable cap trimer-preferring bNAbs PGDM1400, PGT145 and PG16 than JRFL NFL TD15, while the latter was better recognized by the CD4bs-directed bNAbs VRC01, VRC03 and VRC06b (FIG. 25A). This recognition pattern is likely explained in part since the "PG" bNAbs were isolated from patients infected with subtype C HIV whereas the "VRC" bNAbs were isolated from a patient infected with subtype B HIV (Li et al., 2007; Li et al., 2012; Walker et al., 2011; Walker et al., 2009; Wu et al., 2010). In general, within a given Env context, the bNAbs recognized the TD trimers with higher avidity than non-NAbs suggesting native presentation of these two sites and quaternary assembly of the TD trimers. The bNAbs, PGT121 and PGT128, targeting the N332 supersite bound with high avidity to both 16055 and JRFL NFL TD trimers (FIG. 30). The N332 glycan is naturally absent in the 16055 Env but was introduced in the 16055 NFL TD version to accommodate binding of bNAbs targeting this site of vulnerability.

Figure 25B:
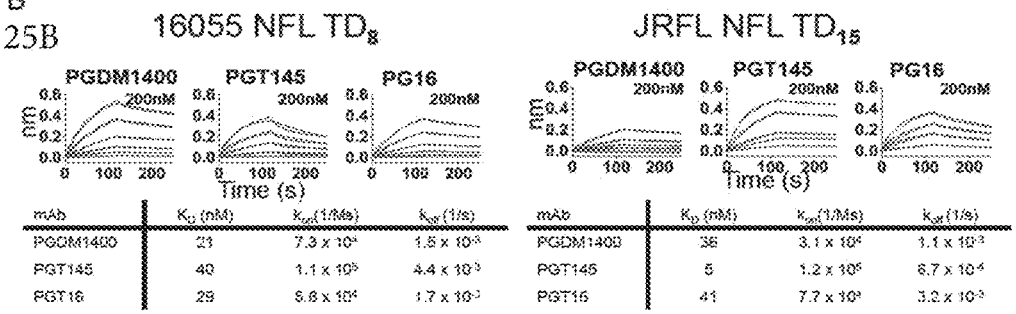

Additionally, since PGDM1400, PGT145 and PG16 only bind one site per spike, Applicants were able to determine bona fide binding kinetics and affinities for these trimer-preferring bNAbs by BLI/Octet. All of these cap-directed bNAbs recognized the TD trimers with nanomolar affinity with PGDM1400 displayed the highest affinity for 16055 NFL TD of 21 nM while PGT145 displayed the highest affinity for JRFL NFL TD of 5 nM (FIG. 25B).

An Engineered Intra-Protomer Disulfide (201-433CC) Link Prevents CD4-Induced NFL Trimer Rearrangements.

Figure 31:
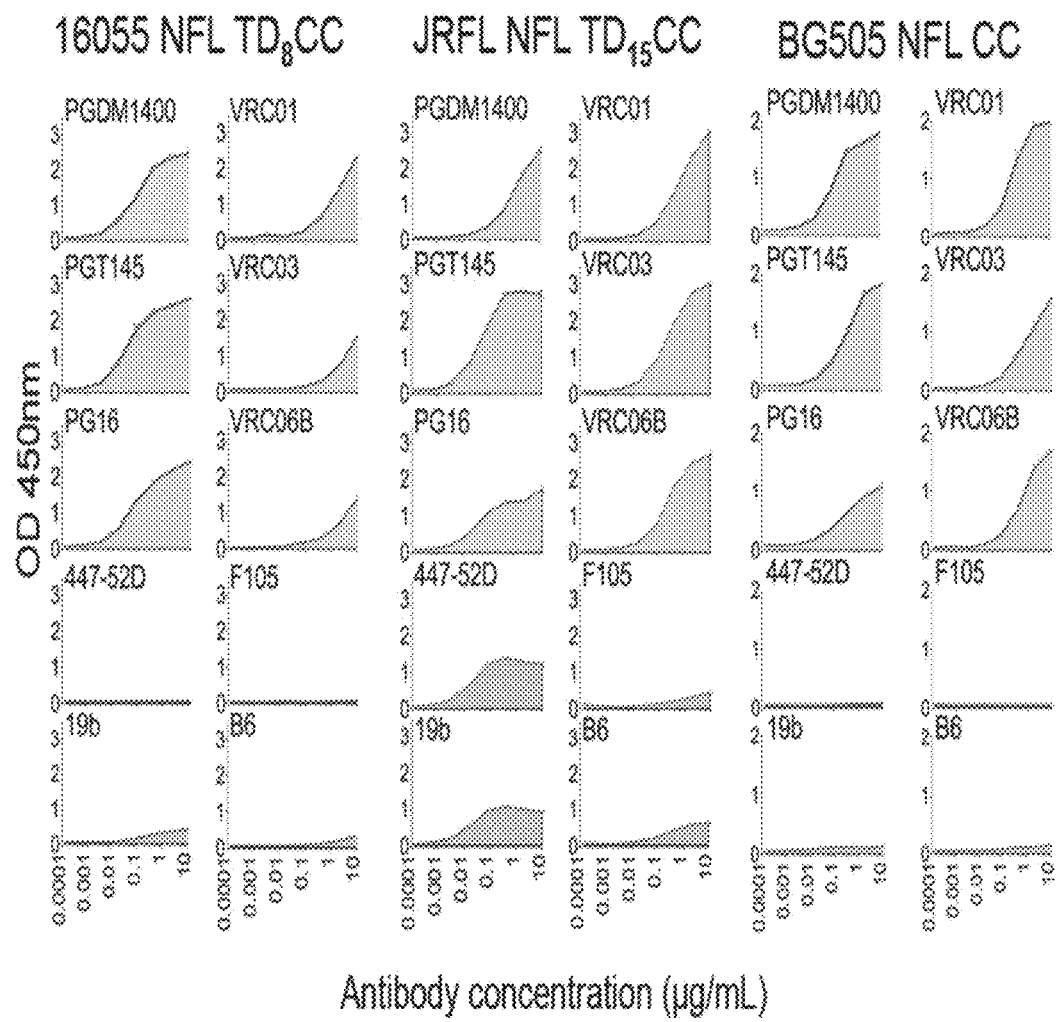
FIG. 31 depicts antigenic profiles of stabilized (201-433CC) NFL trimers. ELISA binding curves of selected bNAbs in blue and non-NAbs in red. PGDM1400, PGT145 and PG16 are trimer-preferring bNABs that target the variable cap region of Env. VRC01, VRC03 and VRC06B are CD4bs-targeting bNAbs. In contrast, 447-52D and 19b are non-NAbs targeting the variable loop 3 and F105 and B6 are non-NAbs targeting the CD4bs.

During natural infection, Env on the surface of the virus engages the primary receptor, CD4, on the target T cell, leading to large conformational changes that form the HIV Env co-receptor binding site. Because in the context of vaccination, these Env soluble mimics will encounter CD4 in NHPs and humans, elimination of CD4-induced changes is desirable if other aspects of the ordered trimers are maintained. Consequently, Applicants sought to further stabilize the NFL trimers beyond the TD modifications so that they would not respond to CD4 engagement, preventing CD4-induced conformational changes that would alter quaternary packing and expose non-neutralizing epitopes. For this purpose, Applicants engineered a disulfide bond between gp120 residues 201 on β3 and 433 on β21 of the gp120 subunit (FIG. 26A). A similar approach has recently been reported in the context of the BG505 SOSIP trimer (Do Kwon et al., 2015). These two β strands are situated adjacent to each other and in parallel in the preceptor-engaged spike structure (Lyumkis et al., 2013). In contrast, published sCD4-liganded gp120 structures reveal β2 rearrangements relative to 133, indicating that CD4 binding influences B20-21, allowing β2-β3 to rearrange and formation of the bridging sheet (FIG. 26A) (Kwong et al., 1998). β2-β3 transition forces V1/V2 to pivot 180 degrees, freeing the underlying V3 "loop" to spring open for co-receptor interaction as part of the viral entry process. This open trimer conformation is recognized by non-NAbs such as 17b or Vc813 that target the receptor-triggered bridging sheet epitope and in a vaccine context may hinder the elicitation of neutralizing antibodies (Huang et al., 2004; Li et al., 2012). Applicants can infer formation of the Cys-Cys pair through trimer binding experiments using the antibodies 17b and Vc813 in the absence or precense of soluble CD4 (sCD4). The bridging sheet epitope is not formed in the pre-receptor engaged spike and becomes accessible only after CD4 engagement. The antibodies 17b and Vc813 efficiently recognized the 16055 NFL TD8, JRLF NFL TD15 and BG505 NFL Wt trimers after incubation with sCD4, indicating the formation of the bridging sheet following CD4-induced conformational changes. In contrast, the disulfide-stabilized trimer variants were not recognized by 17b Vc813 in the absence or presence of sCD4, demonstrating that the bridging sheet was not induced in these additionally stabilized trimers (FIG. 26B). To confirm quaternary packing, Applicants demonstrated that the disulfide engineered NFL trimers were efficiently recognized by bNAbs, including the trimer-preferring and inefficiently by the Non-neutralizing antibodies (FIG. 31).

Figure 27A:
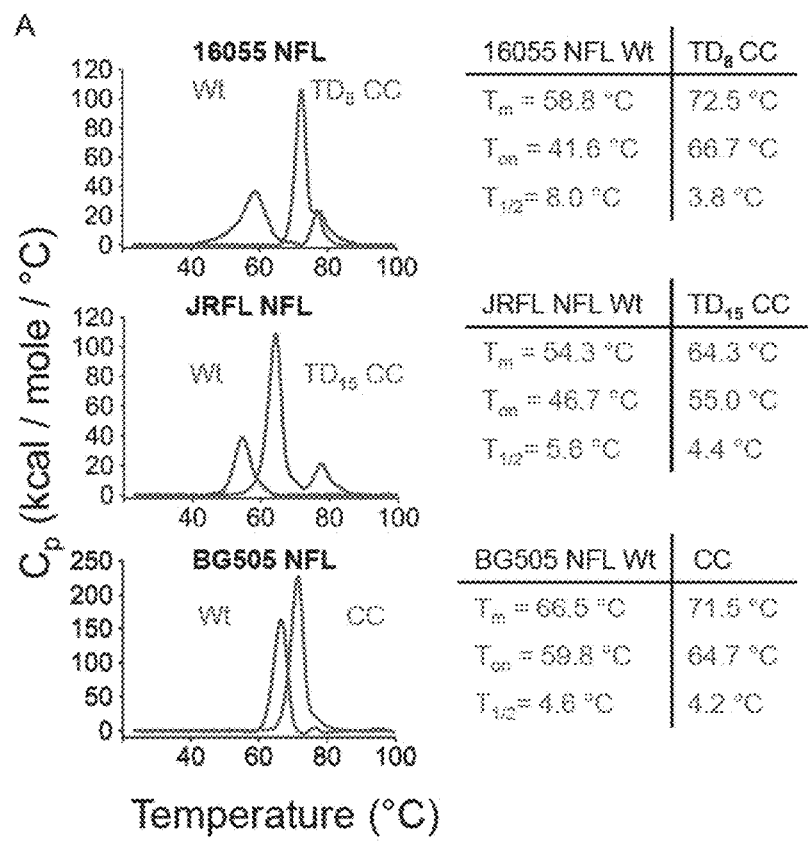
FIGS. 27A-B depicts DSC and EM analysis of the disulfide 201-433CC stabilized NFL trimers. (A) DSC thermal transition curves comparing the wt NFL trimers versus the stabilized trimer variants 16055 NFL TD8 CC, JRFL NFL TD15 CC and BG505 NFL CC. DSC parameters are shown next to the curves in blue for Wt NFLs and in red for the stabilized NFL trimers. (B) Representative negative stain EM 2D-class averages corresponding to the disulfide stabilized NFL trimer variants 16055 NFL TD8 CC, JRFL NFL TD15 CC and BG505 NFL CC.
Figure 27B:
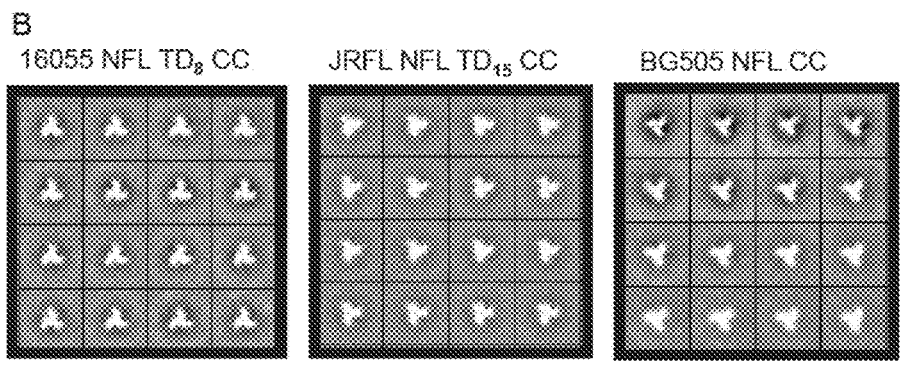
Figure 32:
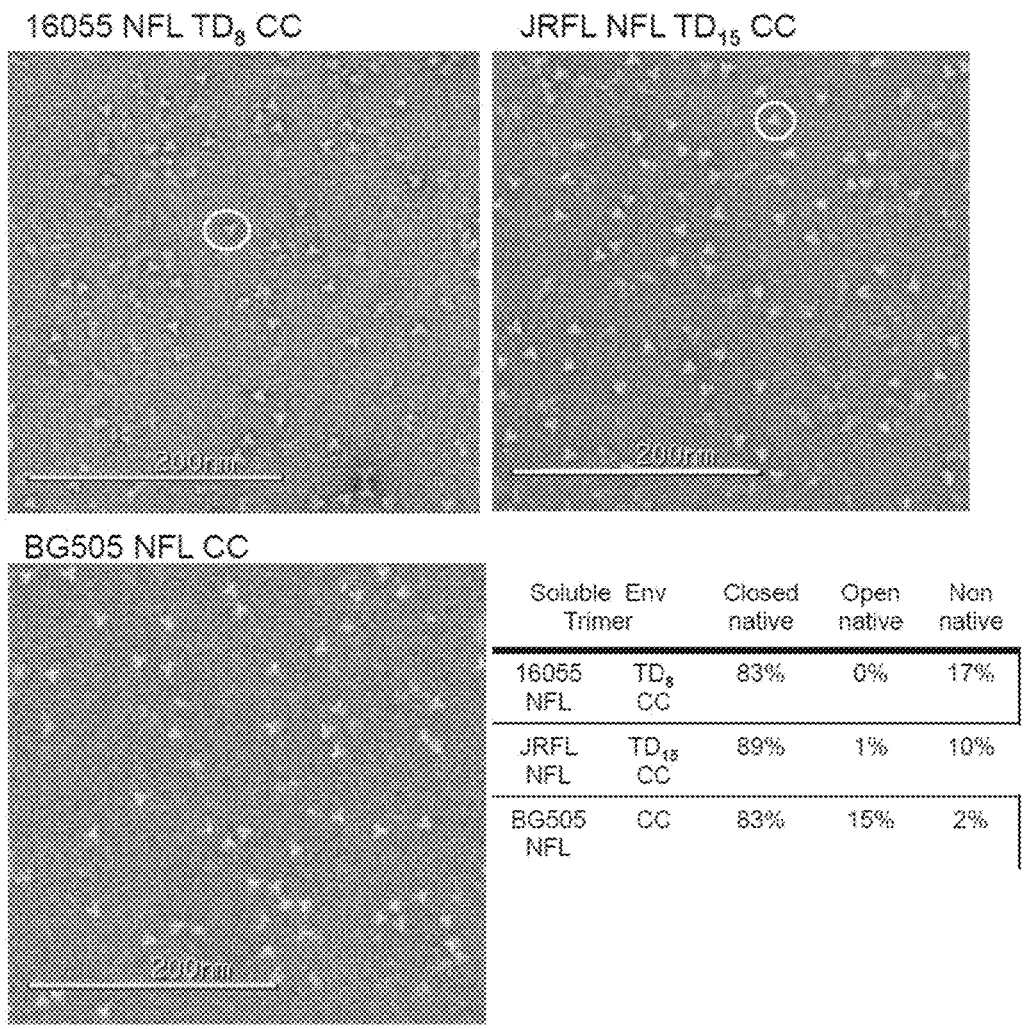
FIG. 32 depicts negative stain EM micrographs of the (201-433CC) stabilized NFL trimers. Micrographs corresponding to negative strain EM for 16055 NFL TD8 CC, JRFL NFL TD15 CC and BG505 NFL CC. Also, the table shows the calculated fractions of native and non-native trimers in the samples.
Figure 33A:
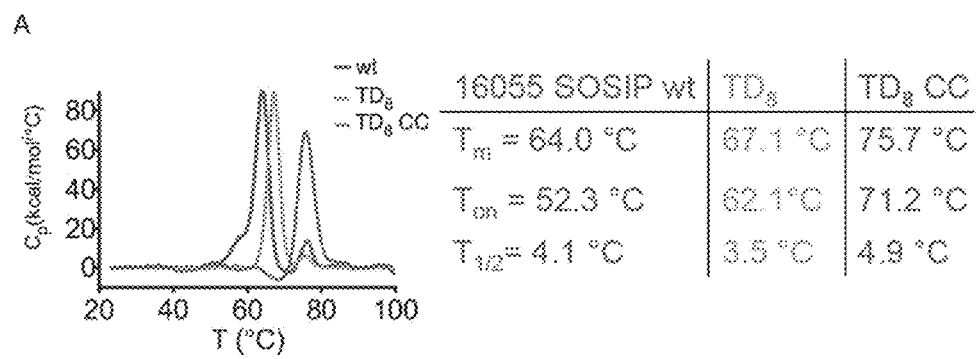
FIGS. 33A-B depicts DSC and EM characterization of stabilized 16055 SOSIP trimer variants. (A) DSC transition melting curves corresponding to 16055 SOSIP wt (blue), TD8 (orange) and TD8 CC (red) and derived DSC parameters. (B) Negative stain EM micrographs and derived 2D class averages for 16055 NFL TD8 and 16055 NFL TD8 CC.
Figure 33B:
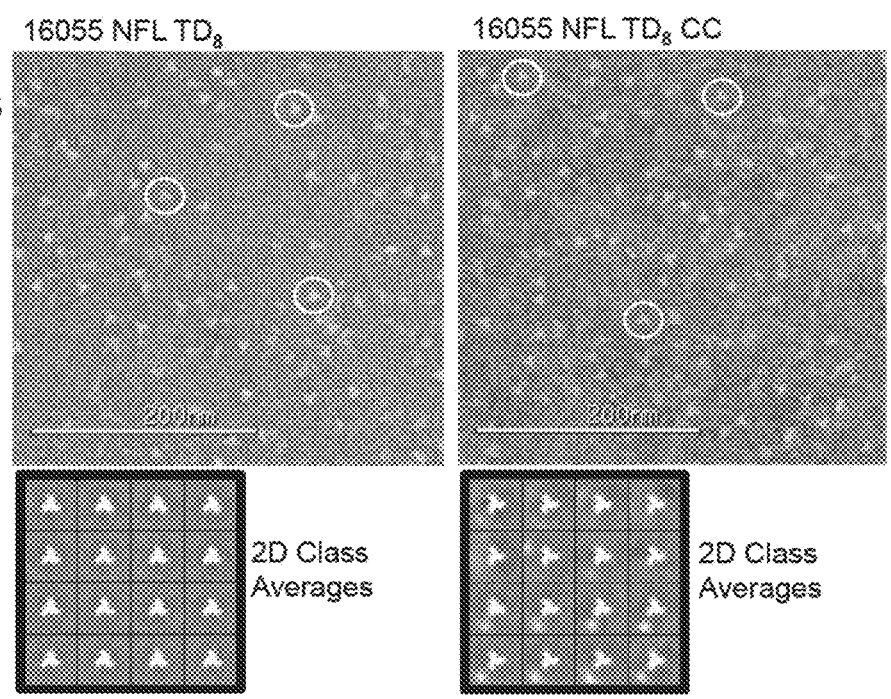

Applicants then investigated the effect of the engineered disulfide linkage (201-433 CC) on overall trimer thermostability. Trimer stability may be relevant to maintain structural integrity in adjuvant at 37° C. in serum or lymph and for antigen presentation in the context of vaccination, improvements of which may lead to a qualitatively better antibody responses. Applicants assessed the Tm of the TD CC trimers by DSC. 16055 NFL TD CC displayed a Tm of 72.5° C., significantly higher than the original wt 16055 NFL trimer (58° C.) (FIG. 27A). Similarly, JRFL NFL TD15 CC displayed a Tm of 64.3° C. significantly higher than the wt JRFL NFL at 54.3° C. and BG505 NFL CC experienced a significant increase in the Tm, to 71.5° C. from wt BG505 NFL 66.5° C. The T1/2 values were narrower; indicating increased molecular homogeneity (FIG. 27A). Analysis of the TD CC trimers by negative-stain EM confirmed that the majority of the trimers adopted a native-like conformation (FIGS. 27B and 32). Applicants introduced the same modifications in the context of 16055 SOSIP, the resulting Tms increased from 64.0° C. for wt to 67.1° C. for the TD8 and 75.7° C. for the TD8 CC variant (FIG. 33A). Unlike the NFLs, the SOSIP CC variant's T1/2 was wider, suggesting increased trimer heterogeneity, likely due to the two unnatural disulfides introduced (SOS and CC), however, EM micrographs and 2D class averages of the SOSIP trimers showed predominantly well-ordered trimers (FIG. 33B).

In this study, Applicants generated improved variants of the soluble NFL trimers derived from the prototypic clade C 16055 and clade B JRFL. Applicants also identified disperse elements of stability of Env that contributed to the enhancement in homogeneity and stability of the improved soluble NFL trimers. To accomplish these improvements, Applicants identified a set of trimer-associated residues via sequence alignment, followed by structure-guided selection on the BG505 SOSIP high-resolution structure (Pancera et al., 2014). Transfer of selected BG505-TD residues, distributed in disperse and distinct regions of Env, was sufficient to increase the propensity of 16055 and JRFL Env sequences to form well-ordered native-like NFL trimers, decreasing aggregation and dissociation into dimers and monomers. Furthermore, the stability of the NFL TD trimer variants, as judged by their thermostability profiles, increased substantially, achieving stability parameters similar to the BG505-derived trimers, demonstrating that the residues identified in this study accurately pinpointed important Env stability elements. Transfer of the BG505 TD residues to the 16055 and JRLF NFL trimers also enhanced homogeneity and ordered trimer final yields. These elements of stability clustered in three different areas of Env; the gp120-gp41 interface, the pre-bridging sheet and the variable region cap. In the 16055 Env context, eight single-residue substitutions were sufficient to increase both homogeneity and stability, while JRFL Env required fifteen to achieve levels of homogeneity and stability approaching that of BG505-derived well-ordered trimers. It is possible that although the specific residues may somewhat differ depending on the specific HIV Env sequence under question, the premise and method of identification of the stability residues could potentially be applicable to many other Env sequences, extending options and Applicants' capacity to generate more diverse, HIV Env soluble spike mimetics. Applicants transferred these improvements as groups of substitutions, making strategic intermediates, but Applicants did not map out the contribution of every residue. Therefore, at this juncture, Applicants do not know the absolute contribution of each of these individual residues, a subject of further study.

In addition to this transferrable trimer-enhancing propensity BG505 signature, Applicants layered on top of these NFL TD trimers, a structure-guided approach, also adopted by others, to further stabilize these spike mimetics. Applicants engineered an intra-protomer disulfide linkage at the proximal positions 201 and 433 of the gp120 subunit. This unnatural covalent bond linking β3 and β21, if formed, would prevent the formation of the bridging sheet by not allowing the positional receptor triggered "switch" between β3 and β2. This swap is inferred from the structures of the BG505 SOSIP, which is presumably in the pre-receptor-engaged state, in which β3 aligns in parallel to β21. By inference and using the CD4-bound gp120 core high-resolution structure, β2 aligns in an antiparallel manner with respect to β21, reflecting β2- and β3-focused conformational changes following CD4 engagement. Essentially CD4 extracts β21-22, allowing a repositioning of β2 relative to β3 of nearly 180 degrees, this pivot triggers that torqueing of the V1 stem, allowing V1/V2 to swing open from the closed pre-receptor state, forming the full coreceptor binding site (CoRbs) with the distal bridging sheet and now V1/V2-released and V3 extended.

The antibodies 17b and Vc813 recognized the 16055 NFL TD8, JRFL NFL TD15 and BG505 NFL trimers after CD4 induction while they did not recognize the disulfide-stabilized CC trimer variants. These results are consistent with the formation of the engineered linkage between the β3 and β21, and with an inability to form the receptor-induced bridging sheet. The stabilized (201-433CC) trimers displayed a superior thermostability profile compared to the TD and wt variants, with higher Tms and narrower T1/2s, providing supporting evidence that the engineered disulfide was formed. EM analysis revealed that the trimers remained well-ordered in the presence of the specific substitutions. In the absence of a high-resolution structure, formation of the bridging sheet disulfide pair is indirect but the experimental data described here are consistent with Cys-Cys pair formation and the subsequent inability of CD4 to induce 17b-sensing conformational changes in the 201-433 CC variant compared to TD trimer alone.

Overall enhanced trimer stability is desired to maintain conformational integrity in vivo so that during the immune response/GC reaction, B cells will encounter only the preferentially exposed neutralizing epitopes on the trimeric immunogens, thereby preferentially driving B cells sensing these targets. B cells recognizing non-neutralizing determinants, exposed when the trimer loses structural integrity, should be disfavored. In addition, engineered stable and well-ordered trimers that are not conformationally altered by soluble CD4 interaction may be important when such spike mimetics are inoculated into NHPs or humans that possess CD4+ cells displaying CD4 with high affinity for Env. Immunogen:CD4 interaction could potentially disrupt the quaternary packing of the novel well-ordered HIV-1 soluble spike mimetics and expose undesirable non-neutralizing epitopes to the primate humoral immune system. The stepwise designs described here provide insight into key regions of Env involved in trimer integrity. These designs also provide improved tools to interrogate the immune response to test the hypothesis whether structure-based Env trimer stability will alter the immunogenic outcome or if eliminating induction by CD4 in primates will better elicit vaccine-induced HIV-1 neutralizing antibodies.

Design of NFL TD Trimer Constructs.

The 16055 and JRFL primary sequences were modified as follows to express fully uncleaved but covalently linked soluble gp140s. The furin cleavage motif at the C-terminus of gp120, "REKR" (SEQ ID NO: 1), was genetically deleted and replaced with 2 copies of the G45 (GGGGS (SEQ ID NO: 2)) flexible linker, joining gp120 covalently to the N-terminus of gp41. A proline substitution at residue 559 was introduce to facilitate trimerication (Sanders et al., 2002). The MPER sequence was deleted from the constructs for better expression (Klasse et al., 2013) and the native signal sequence was replaced by the CD5 leader sequence for better secretion of the proteins. The gp140 sequence was terminated at D664 followed by a G45 linker (SEQ ID NO: 2), His6 tag (SEQ ID NO: 3) and stop codon. For JRFL, E168K mutation was introduced to restore PG9/PG16 binding, and K334S was introduced in 16055 to restore the N-glycan at position 332. The gene constructs were codon optimized for mammalian expression and synthesized (GenScript). The gp140s designed here are designated as "Native Flexibly Linked" (NFL) Envs, with 2× G45 (SEQ ID NO: 4) named as Wt NFL. The NFL TD variants contained the additional substitutions derived from the BG505 HIV Env sequences as follows: for 16055 NFL TD8 (E47D, K49E, V65K, E106T, I165L, E429R, R432Q, A500R) and for JRFL NFL TD15 (E47D, T49E, V65K, E106T, S164E, I165L, E172V, H308R, E429R, K432Q, K500R, L543N, N553S, G588R, E662A). The TD CC variants contained the TD modifications and the following additional substitutions: I201C and A433C.

Site-Directed Mutagenesis.

The TD and CC substitutions were introduced via site-directed mutagenesis PCR reaction using a QuikChange Lightning Multi Site-Directed Mutagenesis kit (Agilent Technologies). In brief, single primers were designed for each mutation. Applicants used up to five primers in each reaction to knock in multiple substitutions at once. Reaction products were transformed into competent bacterial cells and plated on Kanamycin resistant plates for colony selection and subsequent plasmid DNA sequencing.

Expression and Purification of Soluble Trimeric Proteins.

The trimeric proteins were transiently expressed in 293F cells using 293fectin transfection reagent (Invitrogen). Cell culture supernatants were harvested 5-6 days post transfection and the proteins purified by affinity chromatography using a *Galanthus nivalis* lectin-agarose (Vector Labs) column. The bound proteins were eluted with PBS containing 500 mM NaCl and 500 mM methyl-α-D-mannopyranoside then concentrated with an Amicon filer device (100 kDa) to 1 mL. The lectin-purified proteins were subsequently purified by size exclusion chromatography (SEC) using a HiLoad Superdex 200 16/60 column to isolate the trimer fractions.

Differential Scanning Calorimetry (DSC).

The thermal melting of 16055 and JRFL trimeric proteins was probed by DSC using a MicroCal VP-Capillary differential scanning calorimeter instrument (General Electric). Prior to the DSC melting scan, the protein samples were extensively dialyzed in PBS, pH 7.4 and the concentration was adjusted to 0.25 mg/ml. The dialysis buffer was used as the reference solution. The DSC experiments were done at the scanning rate of 1 K/min under 3.0 atmospheres of pressure. DSC data were analyzed after buffer correction, normalization and baseline subtraction using CpCalc software provided by the manufacturer.

Electron Microscopy Sample Preparation.

The purified trimers were analyzed by negative stain-EM. A 3 µL aliquot containing ~0.03 mg/mL of the sample was applied for 15 s onto a carbon-coated 400 Cu mesh grid that had been glow discharged at 20 mA for 30 s, then negatively stained with 2% uranyl formate for 30 s. Data were collected using a FEI Tecnai Spirit electron microscope operating at 120 kV, with an electron dose of ~30 e-/Å2 and a magnification of 52,000× that resulted in a pixel size of 2.05 Å at the specimen plane. Images were acquired with a Tietz 4 k×4 k TemCam-F416 CMOS camera using a nominal defocus of 1000 nm and the Leginon package (Suloway et al., 2005).

Data Processing.

Particles were picked automatically using DoG Picker and put into a particle stack using the Appion software package (Lander et al., 2009; Voss et al., 2009). Reference-free, two-dimensional (2D) class averages were calculated using particles binned by two via the iterative msa/mra Clustering 2D Alignment (Sorzano et al., 2010) and IMAGIC software systems (van Heel et al., 1996) and sorted into classes. To analyze the quality of the trimers (closed, open or non-native like trimers) the reference free 2D class averages were examined by eye using the same metrics that previously described (Pugach et al., 2015).

Trimer Binding Analysis by ELISA.

MaxiSorp plates (Thermo) were coated overnight at 4° C. with 1 µg/mL of a mouse anti-HIS tag monoclonal antibody (R&D Systems) in PBS pH 7.5. The next day the plates were incubated at 4° C. in blocking buffer (2% weight Milk powder+5% vol. Fetal Bovine Serum in PBS pH 7.5) for 2 hours and then washed three times in 0.05% Tween 20 PBS p H 7.4. The Env soluble trimer was added to the plate (100 µL per well) at a concentration of 2 µg/mL in blocking buffer and incubated at 4° C. for 1 hour. The plates were washed three times in 0.05% Tween 20 PBS pH 7.4. The primary antibodies (human HIV bNABs) were added to the plates at a maximum concentration of 5 µg/mL and serially diluted 1:5 in blocking buffer. The plates were incubated at 4° C. for 1 hour and then washed three times in 0.05% Tween 20 PBS p H 7.4. A secondary antibody (peroxidase conjugated goat anti-human IgG antibody by Jackson ImmunoResearch Labs) diluted 5000× in blocking buffer was added to the plates and incubated at 4° C. for 30 minutes. Then the plates were washed three times in 0.05% Tween 20 PBS p H 7.4. The substrate solution (TMB Chromogen Solution (3,3'5,5 tetramethyl benzyidine by Invitrogen) was added to the plates (100 µL per well) and incubate at RT for 5 minutes. 100 µL per well of 1N Sulfuric Acid was added to stop reaction and the plates were read at 450 nm.

Bio-Layer Interferometry (BLI) Binding Analysis and Kinetics.

Kinetic measurements were obtained with an Octet Red instrument immobilizing IgGs on a previously hydrated (PBS pH 7.4) anti-human IgG Fc sensors (Fortebio, Inc.). The NFL trimers were analyzed as analytes free in solution (PBS pH 7.4). Briefly, the bio-sensors were immersed in PBS pH 7.4 containing IgGs at a concentration of 10 ug/mL for 2 minutes and 1000 rpm prior to encounter the analyte (NFL trimers at a maximum concentration of 200 nM and then serially diluted 1:2 to 12.5 nM). The IgG-immobilized sensor was in contact with the analyte in solution for 2 minutes at 1000 rpm and then removed from the analyte and placed into PBS pH 7.4 for another 3 minutes. These time intervals generated the association and dissociation binding curves reported in this study. Data Analysis was done using the ForteBio analysis software version 7.1 (ForteBio) and the kinetic parameters were calculated using a global fit 1:1 model for applicable mAbs.

REFERENCES

Bartesaghi, A., Merk, A., Borgnia, M. J., Milne, J. L., Subramaniam, S., 2013. Prefusion structure of trimeric HIV-1 envelope glycoprotein determined by cryo-electron microscopy. Nat Struct Mol Biol 20, 1352-1357.

Binley, J. M., Sanders, R. W., Clas, B., Schuelke, N., Master, A., Guo, Y., Kajumo, F., Anselma, D. J., Maddon, P. J., Olson, W. C., Moore, J. P., 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74, 627-643.

Binley, J. M., Sanders, R. W., Master, A., Cayanan, C. S., Wiley, C. L., Schiffner, L., Travis, B., Kuhmann, S., Burton, D. R., Hu, S. L., Olson, W. C., Moore, J. P., 2002. Enhancing the proteolytic maturation of human immunodeficiency virus type 1 envelope glycoproteins. J Virol 76, 2606-2616.

Blattner, C., Lee, J. H., Sliepen, K., Derking, R., Falkowska, E., de la Pena, A. T., Cupo, A., Julien, J. P., van Gils, M., Lee, P. S., Peng, W., Paulson, J. C., Poignard, P., Burton, D. R., Moore, J. P., Sanders, R. W., Wilson, I. A., Ward, A. B., 2014. Structural Delineation of a Quaternary, Cleavage-Dependent Epitope at the gp41-gp120 Interface on Intact HIV-1 Env Trimers. Immunity.

Do Kwon, Y., Pancera, M., Acharya, P., Georgiev, I. S., Crooks, E. T., Gorman, J., Joyce, M. G., Guttman, M., Ma, X., Narpala, S., Soto, C., Terry, D. S., Yang, Y., Zhou, T., Ahlsen, G., Bailer, R. T., Chambers, M., Chuang, G. Y., Doria-Rose, N. A., Druz, A., Hallen, M. A., Harned, A., Kirys, T., Louder, M. K., O'Dell, S., Ofek, G., Osawa, K., Prabhakaran, M., Sastry, M., Stewart-Jones, G. B., Stuckey, J., Thomas, P. V., Tittley, T., Williams, C., Zhang, B., Zhao, H., Zhou, Z., Donald, B. R., Lee, L. K., Zolla-Pazner, S., Baxa, U., Schon, A., Freire, E., Shapiro, L., Lee, K. K., Arthos, J., Munro, J. B., Blanchard, S. C., Mothes, W., Binley, J. M., McDermott, A. B., Mascola, J. R., Kwong, P. D., 2015. Crystal structure, conformational fixation and entry-related interactions of mature ligand-free HIV-1 Env. Nat Struct Mol Biol.

Earl, P. L., Broder, C. C., Long, D., Lee, S. A., Peterson, J., Chakrabarti, S., Doms, R. W., Moss, B., 1994. Native oligomeric human immunodeficiency virus type 1 envelope glycoprotein elicits diverse monoclonal antibody reactivities. J Virol 68, 3015-3026.

Earl, P. L., Sugiura, W., Montefiori, D. C., Broder, C. C., Lee, S. A., Wild, C., Lifson, J., Moss, B., 2001. Immunogenicity and protective efficacy of oligomeric human immunodeficiency virus type 1 gp140. J Virol 75, 645-653.

Forsell, M. N., Li, Y., Sundback, M., Svehla, K., Liljestrom, P., Mascola, J. R., Wyatt, R., Karlsson Hedestam, G. B., 2005. Biochemical and immunogenic characterization of soluble human immunodeficiency virus type 1 envelope glycoprotein trimers expressed by semliki forest virus. J Virol 79, 10902-10914.

Gao, F., Weaver, E. A., Lu, Z., Li, Y., Liao, H. X., Ma, B., Alam, S. M., Scearce, R. M., Sutherland, L. L., Yu, J. S., Decker, J. M., Shaw, G. M., Montefiori, D. C., Korber, B. T., Hahn, B. H., Haynes, B. F., 2005. Antigenicity and immunogenicity of a synthetic human immunodeficiency virus type 1 group m consensus envelope glycoprotein. J Virol 79, 1154-1163.

Georgiev, I. S., Joyce, M. G., Yang, Y., Sastry, M., Zhang, B., Baxa, U., Chen, R. E., Druz, A., Lees, C. R., Narpala, S., Schon, A., Van Galen, J., Chuang, G. Y., Gorman, J., Harned, A., Pancera, M., Stewart-Jones, G. B., Cheng, C., Freire, E., McDermott, A. B., Mascola, J. R., Kwong, P. D., 2015. Single-chain soluble BG505.SOSIP gp140 trimers as structural and antigenic mimics of mature closed HIV-1 Env. J Virol.

Guenaga, J., de Val, N., Tran, K., Feng, Y., Satchwell, K., Ward, A. B., Wyatt, R. T., 2015. Well-Ordered Trimeric HIV-1 Subtype B and C Soluble Spike Mimetics Generated by Negative Selection Display Native-like Properties. PLoS Pathog 11, e1004570.

Huang, C. C., Venturi, M., Majeed, S., Moore, M. J., Phogat, S., Zhang, M. Y., Dimitrov, D. S., Hendrickson, W. A., Robinson, J., Sodroski, J., Wyatt, R., Choe, H., Farzan, M., Kwong, P. D., 2004. Structural basis of tyrosine sulfation and VH-gene usage in antibodies that recognize the HIV type 1 coreceptor-binding site on gp120. Proc Natl Acad Sci USA 101, 2706-2711.

Julien, J. P., Cupo, A., Sok, D., Stanfield, R. L., Lyumkis, D., Deller, M. C., Klasse, P. J., Burton, D. R., Sanders, R. W., Moore, J. P., Ward, A. B., Wilson, I. A., 2013. Crystal structure of a soluble cleaved HIV-1 envelope trimer. Science 342, 1477-1483.

Klasse, P. J., Depetris, R. S., Pejchal, R., Julien, J. P., Khayat, R., Lee, J. H., Marozsan, A. J., Cupo, A., Cocco, N., Korzun, J., Yasmeen, A., Ward, A. B., Wilson, I. A., Sanders, R. W., Moore, J. P., 2013. Influences on trimerization and aggregation of soluble, cleaved HIV-1 SOSIP envelope glycoprotein. J Virol 87, 9873-9885.

Kovacs, J. M., Noeldeke, E., Ha, H. J., Peng, H., Rits-Volloch, S., Harrison, S. C., Chen, B., 2014. Stable, uncleaved HIV-1 envelope glycoprotein gp140 forms a tightly folded trimer with a native-like structure. Proc Natl Acad Sci USA 111, 18542-18547.

Kwong, P. D., Wyatt, R., Robinson, J., Sweet, R. W., Sodroski, J., Hendrickson, W. A., 1998. Structure of an HIV gp120 envelope glycoprotein in complex with the CD4 receptor and a neutralizing human antibody. Nature 393, 648-659.

Lander, G. C., Stagg, S. M., Voss, N. R., Cheng, A., Fellmann, D., Pulokas, J., Yoshioka, C., Irving, C., Mulder, A., Lau, P. W., Lyumkis, D., Potter, C. S., Carragher, B., 2009. Appion: an integrated, database-driven pipeline to facilitate EM image processing. Journal of structural biology 166, 95-102.

Li, Y., Migueles, S. A., Welcher, B., Svehla, K., Phogat, A., Louder, M. K., Wu, X., Shaw, G. M., Connors, M., Wyatt, R. T., Mascola, J. R., 2007. Broad HIV-1 neutralization mediated by CD4-binding site antibodies. Nat Med 13, 1032-1034.

Li, Y., O'Dell, S., Wilson, R., Wu, X., Schmidt, S. D., Hogerkorp, C. M., Louder, M. K., Longo, N. S., Poulsen, C., Guenaga, J., Chakrabarti, B. K., Doria-Rose, N., Roederer, M., Connors, M., Mascola, J. R., Wyatt, R. T., 2012. HIV-1 neutralizing antibodies display dual recognition of the primary and coreceptor binding sites and preferential binding to fully cleaved envelope glycoproteins. J Virol 86, 11231-11241.

Lyumkis, D., Julien, J. P., de Val, N., Cupo, A., Potter, C. S., Klasse, P. J., Burton, D. R., Sanders, R. W., Moore, J. P., Carragher, B., Wilson, I. A., Ward, A. B., 2013. Cryo-EM structure of a fully glycosylated soluble cleaved HIV-1 envelope trimer. Science 342, 1484-1490.

Pancera, M., Zhou, T., Druz, A., Georgiev, I. S., Soto, C., Gorman, J., Huang, J., Acharya, P., Chuang, G. Y., Ofek, G., Stewart-Jones, G. B., Stuckey, J., Bailer, R. T., Joyce, M. G., Louder, M. K., Tumba, N., Yang, Y., Zhang, B., Cohen, M. S., Haynes, B. F., Mascola, J. R., Morris, L., Munro, J. B., Blanchard, S. C., Mothes, W., Connors, M., Kwong, P. D., 2014. Structure and immune recognition of trimeric pre-fusion HIV-1 Env. Nature.

Pugach, P., Ozorowski, G., Cupo, A., Ringe, R., Yasmeen, A., de Val, N., Derking, R., Kim, H. J., Korzun, J., Golabek, M., de Los Reyes, K., Ketas, T. J., Julien, J. P., Burton, D. R., Wilson, I. A., Sanders, R. W., Klasse, P. J., Ward, A. B., Moore, J. P., 2015. A native-like SOSIP.664 trimer based on a HIV-1 subtype B env gene. J Virol.

Sanders, R. W., Derking, R., Cupo, A., Julien, J. P., Yasmeen, A., de Val, N., Kim, H. J., Blattner, C., de la Pena, A. T., Korzun, J., Golabek, M., de Los Reyes, K., Ketas, T. J., van Gils, M. J., King, C. R., Wilson, I. A., Ward, A. B., Klasse, P. J., Moore, J. P., 2013. A next-generation cleaved, soluble HIV-1 Env Trimer, BG505 SOSIP.664 gp140, expresses multiple epitopes for broadly neutralizing but not non-neutralizing antibodies. PLoS Pathog 9, e1003618.

Sanders, R. W., van Gils, M. J., Derking, R., Sok, D., Ketas, T. J., Burger, J. A., Ozorowski, G., Cupo, A., Simonich, C., Goo, L., Arendt, H., Kim, H. J., Lee, J. H., Pugach, P., Williams, M., Debnath, G., Moldt, B., van Breemen, M.

J., Isik, G., Medina-Ramirez, M., Back, J. W., Koff, W. C., Julien, J. P., Rakasz, E. G., Seaman, M. S., Guttman, M., Lee, K. K., Klasse, P. J., LaBranche, C., Schief, W. R., Wilson, I. A., Overbaugh, J., Burton, D. R., Ward, A. B., Montefiori, D. C., Dean, H., Moore, J. P., 2015. HIV-1 VACCINES. HIV-1 neutralizing antibodies induced by native-like envelope trimers. Science 349, aac4223.

Sanders, R. W., Vesanen, M., Schuelke, N., Master, A., Schiffner, L., Kalyanaraman, R., Paluch, M., Berkhout, B., Maddon, P. J., Olson, W. C., Lu, M., Moore, J. P., 2002. Stabilization of the soluble, cleaved, trimeric form of the envelope glycoprotein complex of human immunodeficiency virus type 1. J Virol 76, 8875-8889.

Sharma, S. K., de Val, N., Bale, S., Guenaga, J., Tran, K., Feng, Y., Dubrovskaya, V., Ward, A. B., Wyatt, R. T., 2015. Cleavage-Independent HIV-1 Env Trimers Engineered as Soluble Native Spike Mimetics for Vaccine Design. Cell reports 11, 539-550.

Sok, D., van Gils, M. J., Pauthner, M., Julien, J. P., Saye-Francisco, K. L., Hsueh, J., Briney, B., Lee, J. H., Le, K. M., Lee, P. S., Hua, Y., Seaman, M. S., Moore, J. P., Ward, A. B., Wilson, I. A., Sanders, R. W., Burton, D. R., 2014. Recombinant HIV envelope trimer selects for quaternary-dependent antibodies targeting the trimer apex. Proc Natl Acad Sci USA 111, 17624-17629.

Sorzano, C. O., Bilbao-Castro, J. R., Shkolnisky, Y., Alcorlo, M., Melero, R., Caffarena-Fernandez, G., Li, M., Xu, G., Marabini, R., Carazo, J. M., 2010. A clustering approach to multireference alignment of single-particle projections in electron microscopy. Journal of structural biology 171, 197-206.

Spearman, P., Lally, M. A., Elizaga, M., Montefiori, D., Tomaras, G. D., McElrath, M. J., Hural, J., De Rosa, S. C., Sato, A., Huang, Y., Frey, S. E., Sato, P., Donnelly, J., Barnett, S., Corey, L. J., NIAID, H.I.V.V.T.N.o., 2011. A trimeric, V2-deleted HIV-1 envelope glycoprotein vaccine elicits potent neutralizing antibodies but limited breadth of neutralization in human volunteers. J Infect Dis 203, 1165-1173.

Srivastava, I. K., Stamatatos, L., Kan, E., Vajdy, M., Lian, Y., Hilt, S., Martin, L., Vita, C., Zhu, P., Roux, K. H., Vojtech, L., D, C. M., Donnelly, J., Ulmer, J. B., Barnett, S. W., 2003. Purification, characterization, and immunogenicity of a soluble trimeric envelope protein containing a partial deletion of the V2 loop derived from SF162, an R5-tropic human immunodeficiency virus type 1 isolate. J Virol 77, 11244-11259.

Suloway, C., Pulokas, J., Fellmann, D., Cheng, A., Guerra, F., Quispe, J., Stagg, S., Potter, C. S., Carragher, B., 2005. Automated molecular microscopy: the new Leginon system. Journal of structural biology 151, 41-60.

van Heel, M., Harauz, G., Orlova, E. V., Schmidt, R., Schatz, M., 1996. A new generation of the IMAGIC image processing system. Journal of structural biology 116, 17-24.

Voss, N. R., Yoshioka, C. K., Radermacher, M., Potter, C. S., Carragher, B., 2009. DoG Picker and TiltPicker: software tools to facilitate particle selection in single particle electron microscopy. Journal of structural biology 166, 205-213.

Walker, L. M., Huber, M., Doores, K. J., Falkowska, E., Pejchal, R., Julien, J. P., Wang, S. K., Ramos, A., Chan-Hui, P. Y., Moyle, M., Mitcham, J. L., Hammond, P. W., Olsen, O. A., Phung, P., Fling, S., Wong, C. H., Phogat, S., Wrin, T., Simek, M. D., Protocol, G. P. I., Koff, W. C., Wilson, I. A., Burton, D. R., Poignard, P., 2011. Broad neutralization coverage of HIV by multiple highly potent antibodies. Nature 477, 466-470.

Walker, L. M., Phogat, S. K., Chan-Hui, P. Y., Wagner, D., Phung, P., Goss, J. L., Wrin, T., Simek, M. D., Fling, S., Mitcham, J. L., Lehrman, J. K., Priddy, F. H., Olsen, O. A., Frey, S. M., Hammond, P. W., 2009. Broad and potent neutralizing antibodies from an African donor reveal a new HIV-1 vaccine target. Science 326, 285-289.

Wu, X., Yang, Z. Y., Li, Y., Hogerkorp, C. M., Schief, W. R., Seaman, M. S., Zhou, T., Schmidt, S. D., Wu, L., Xu, L., Longo, N. S., McKee, K., O'Dell, S., Louder, M. K., Wycuff, D. L., Feng, Y., Nason, M., Doria-Rose, N., Connors, M., Kwong, P. D., Roederer, M., Wyatt, R. T., Nabel, G. J., Mascola, J. R., 2010. Rational design of envelope identifies broadly neutralizing human monoclonal antibodies to HIV-1. Science 329, 856-861.

Yang, X., Farzan, M., Wyatt, R., Sodroski, J., 2000a. Characterization of stable, soluble trimers containing complete ectodomains of human immunodeficiency virus type 1 envelope glycoproteins. J Virol 74, 5716-5725.

Yang, X., Florin, L., Farzan, M., Kolchinsky, P., Kwong, P. D., Sodroski, J., Wyatt, R., 2000b. Modifications that stabilize human immunodeficiency virus envelope glycoprotein trimers in solution. J Virol 74, 4746-4754.

Yang, X., Lee, J., Mahony, E. M., Kwong, P. D., Wyatt, R., Sodroski, J., 2002. Highly stable trimers formed by human immunodeficiency virus type 1 envelope glycoproteins fused with the trimeric motif of T4 bacteriophage fibritin. J Virol 76, 4634-4642.

Yang, X., Wyatt, R., Sodroski, J., 2001. Improved elicitation of neutralizing antibodies against primary human immunodeficiency viruses by soluble stabilized envelope glycoprotein trimers. J Virol 75, 1165-1171.

Example 2: Stabilization of V2/V3 Loop and Fusion Peptide of HIV Env Mimetic

Using the JRFL-NFL trimer, Applicants sought to discover pocket filling mutations in the V2/V3 loop and fusion peptide areas to stabilize the trimer without compromising native trimer formation and to apply positive mutations to other NFL trimers such as BG505 and 16055.

Figure 34:
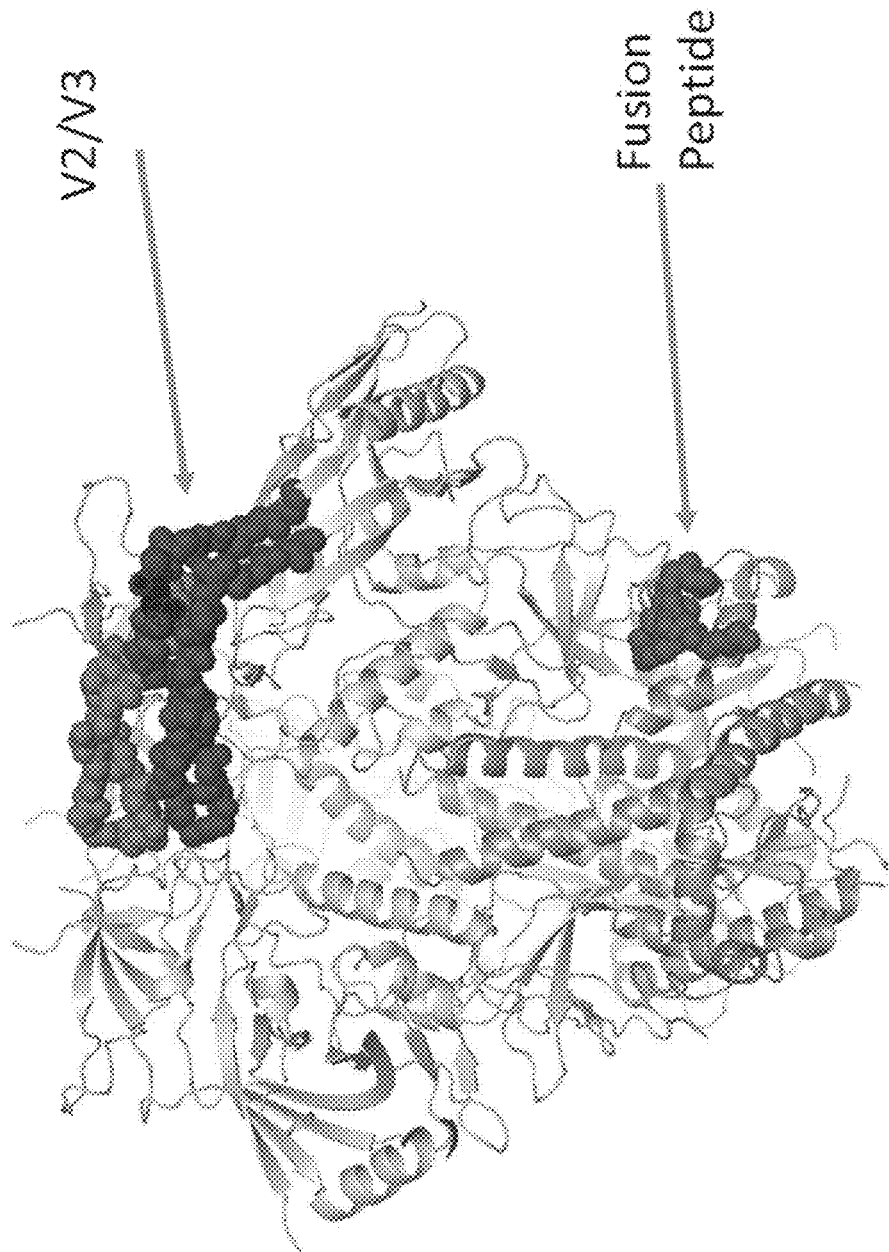
FIG. 34 depicts a structure of the V2/V3 loop and the fusion peptide. Applicants looked at pocket filling mutations in these regions to their flexibility. Applicants initially screened with tryptophans since they are large, bulky and hydrophobic. Applicants made changes and checked for thermal stability as well as trimer formation.

FIG. 34 depicts a structure of the V2/V3 loop and the fusion peptide. Applicants looked at pocket filling mutations in these regions to their flexibility. Applicants initially screened with tryptophans since they are large, bulky and hydrophobic. Applicants made changes and checked for thermal stability as well as trimer formation.

Figure 35:
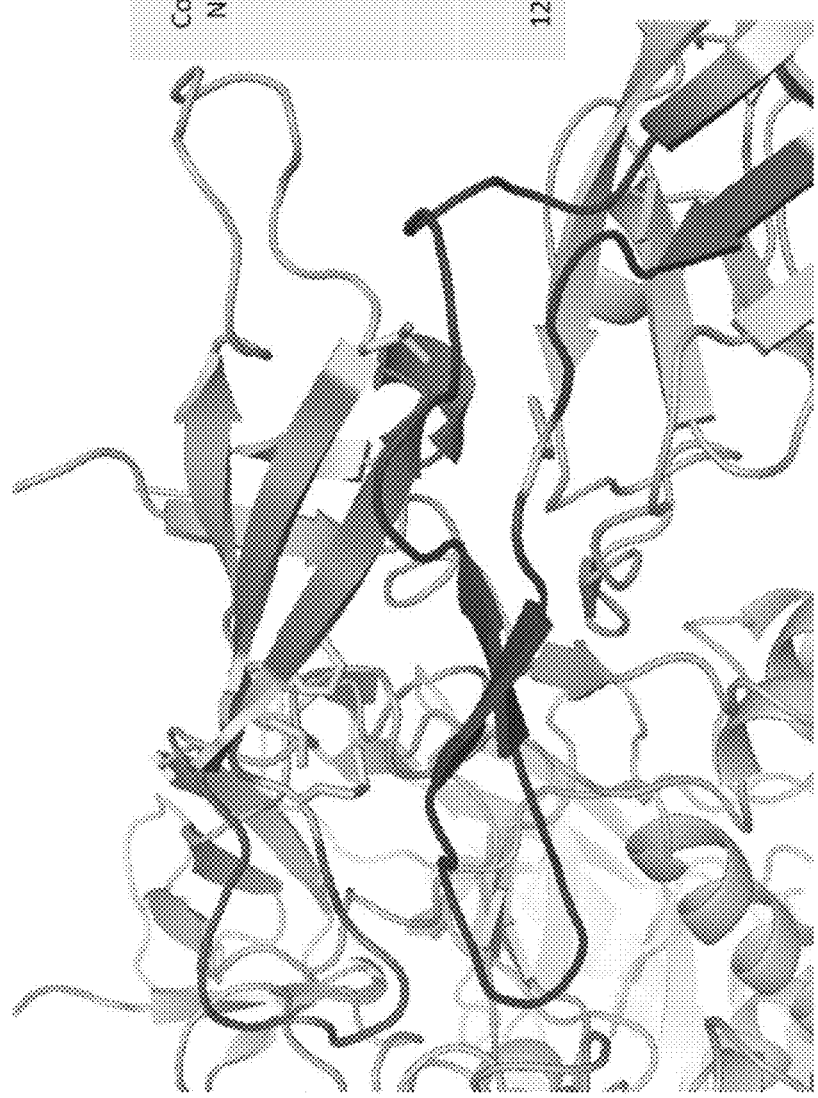
FIG. 35 depicts a close up view of the V2/V3 loop region. The residues in yellow where Applicants made mutations. Of all the loop constructs, only 302W gave a positive result which Applicants used as 302Y.

FIG. 35 depicts a close up view of the V2/V3 loop region. The residues in yellow where Applicants made mutations. Of all the loop constructs, only 302W gave a positive result which Applicants used as 302Y.

Figure 36:
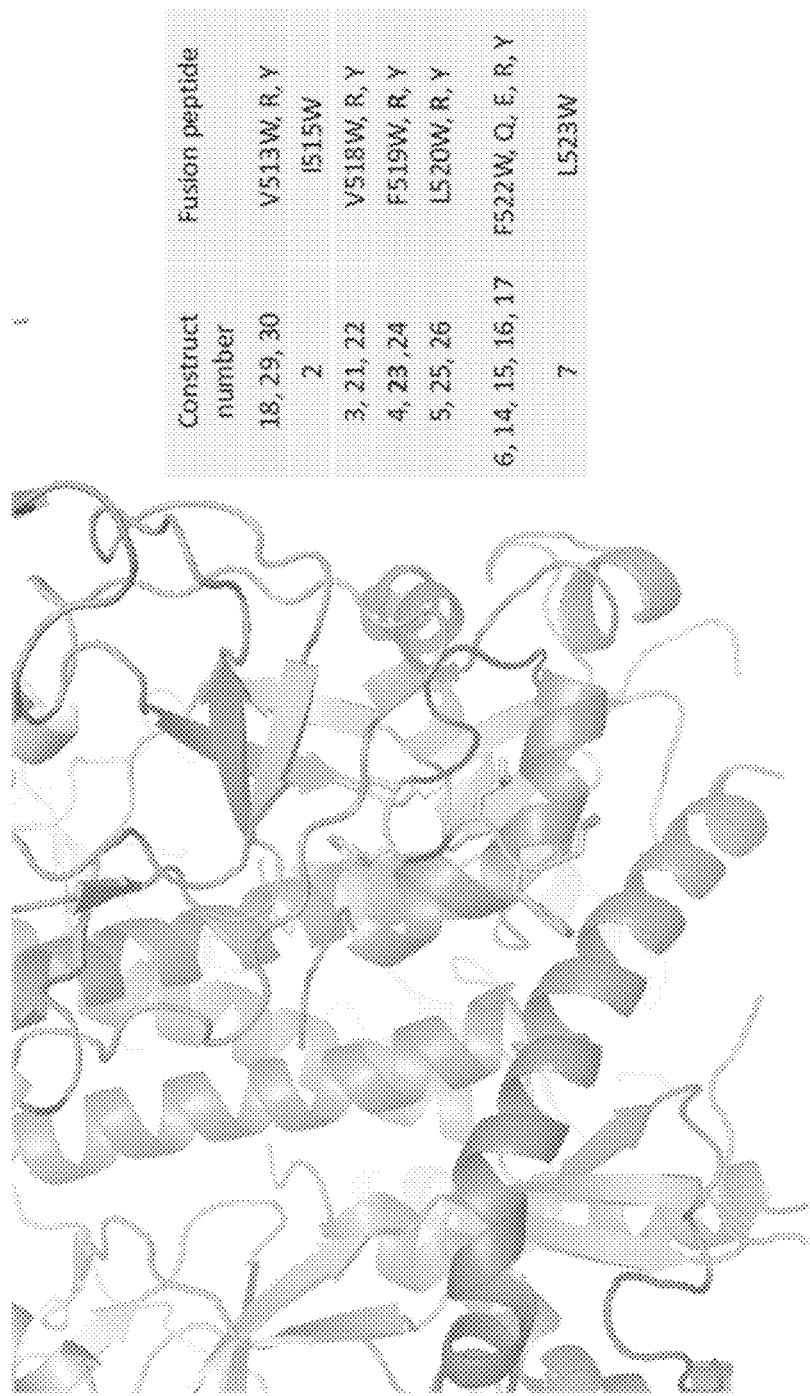
FIG. 36 shows that multiple mutations worked, but Applicants ultimately decided to pursue 519 and 520W which were best when Arginine was inserted.

FIG. 36 shows that multiple mutations worked, but Applicants ultimately decided to pursue 519 and 520W which were best when Arginine was inserted.

Figure 37:
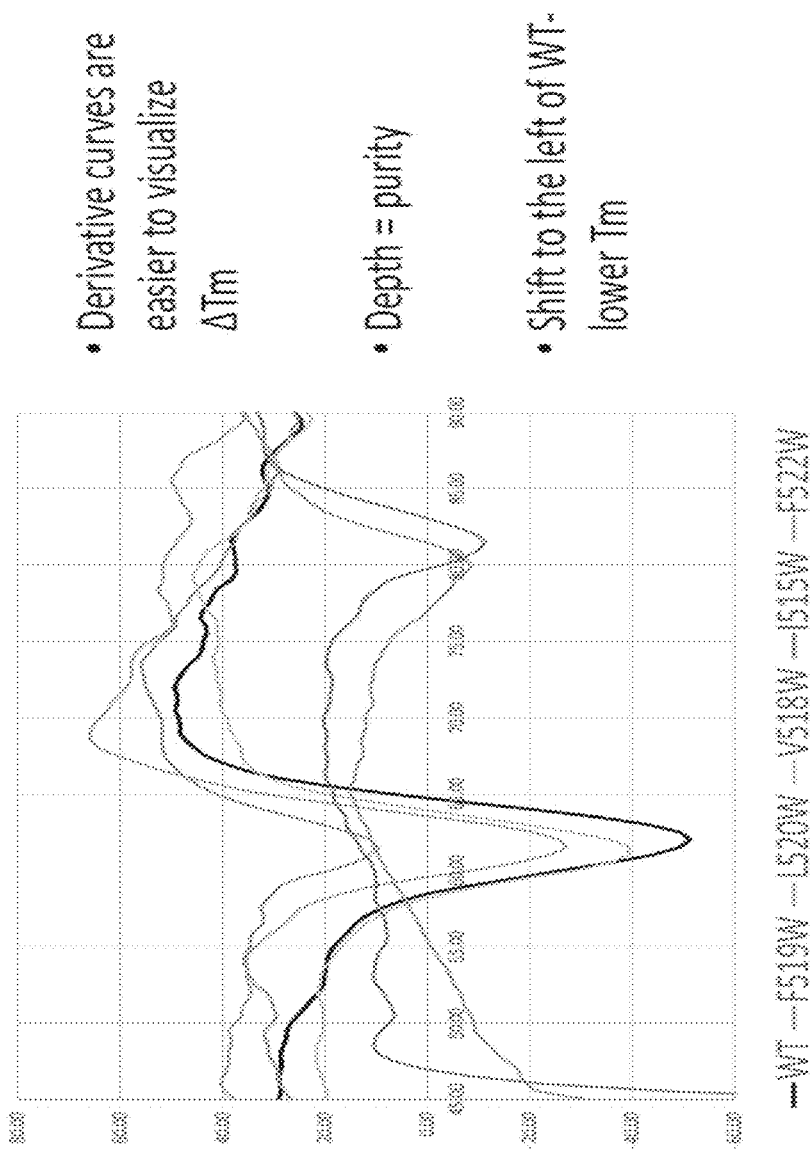
FIG. 37 depicts fusion peptide initial substitutions. After the tryptophans did not really change the melting temperature, but supported trimer formation so Applicants pursued new substitutions like QERY and found R and Y were best. The two curves up around 80 are aggregates.

FIG. 37 depicts fusion peptide initial substitutions. After the tryptophans did not really change the melting temperature, but supported trimer formation so Applicants pursued new substitutions like QERY and found R and Y were best. The two curves up around 80 are aggregates.

Figure 38:
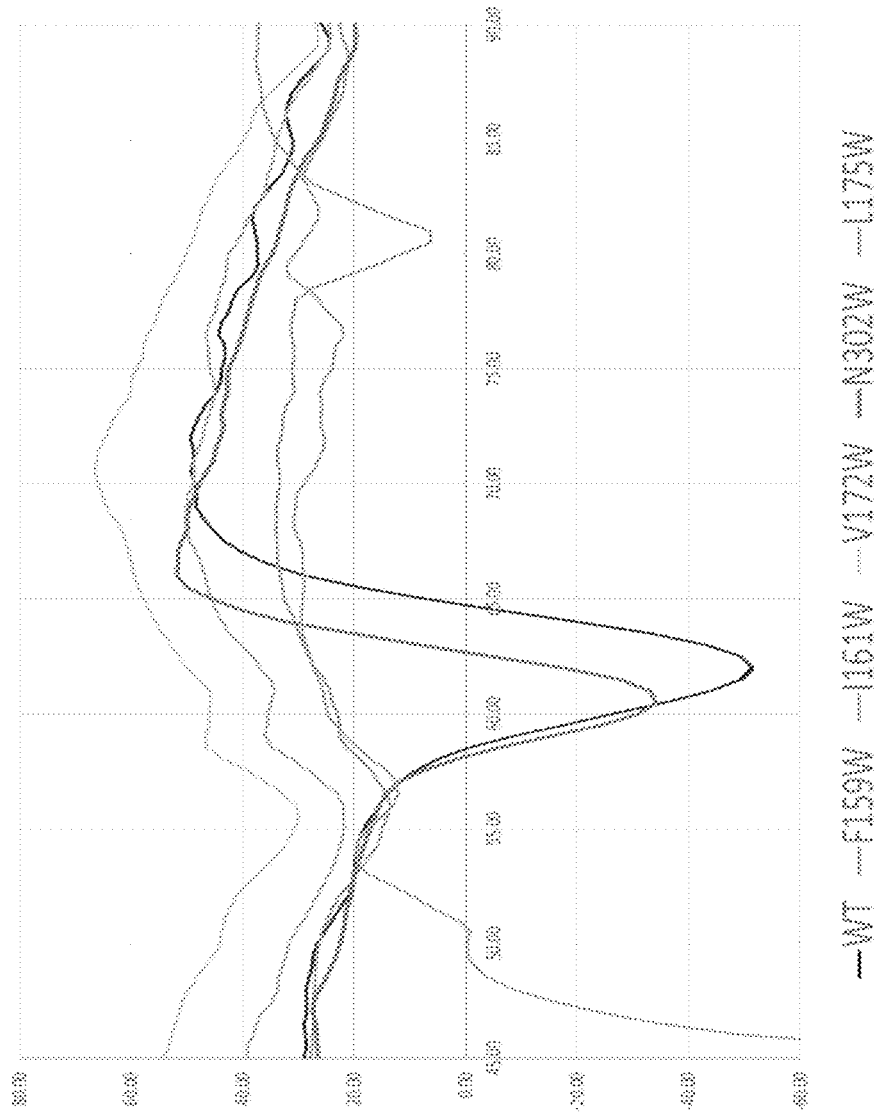
FIG. 38 depicts V2/V3 initial mutations. Only 302 showed a decent melting curve and the orange curve shows aggregates at ~80.

FIG. 38 depicts V2/V3 initial mutations. Only 302 showed a decent melting curve and the orange curve shows aggregates at ~80.

Figure 39:
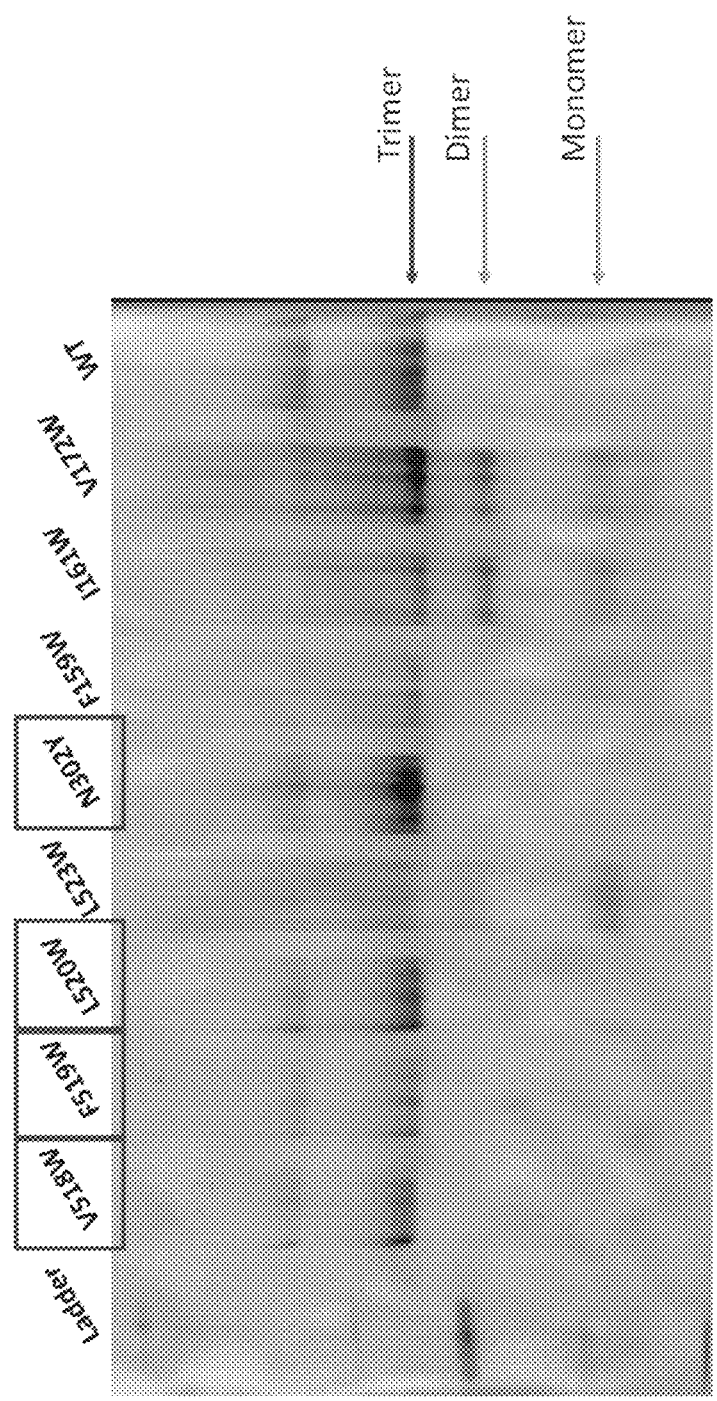
FIG. 39 depicts some of the poorly former trimers, and the aggregation that can be seen. The gels that mimicked WT were taken further into new mutations.

FIG. 39 depicts some of the poorly former trimers, and the aggregation that can be seen. The gels that mimicked WT were taken further into new mutations.

Figure 40:
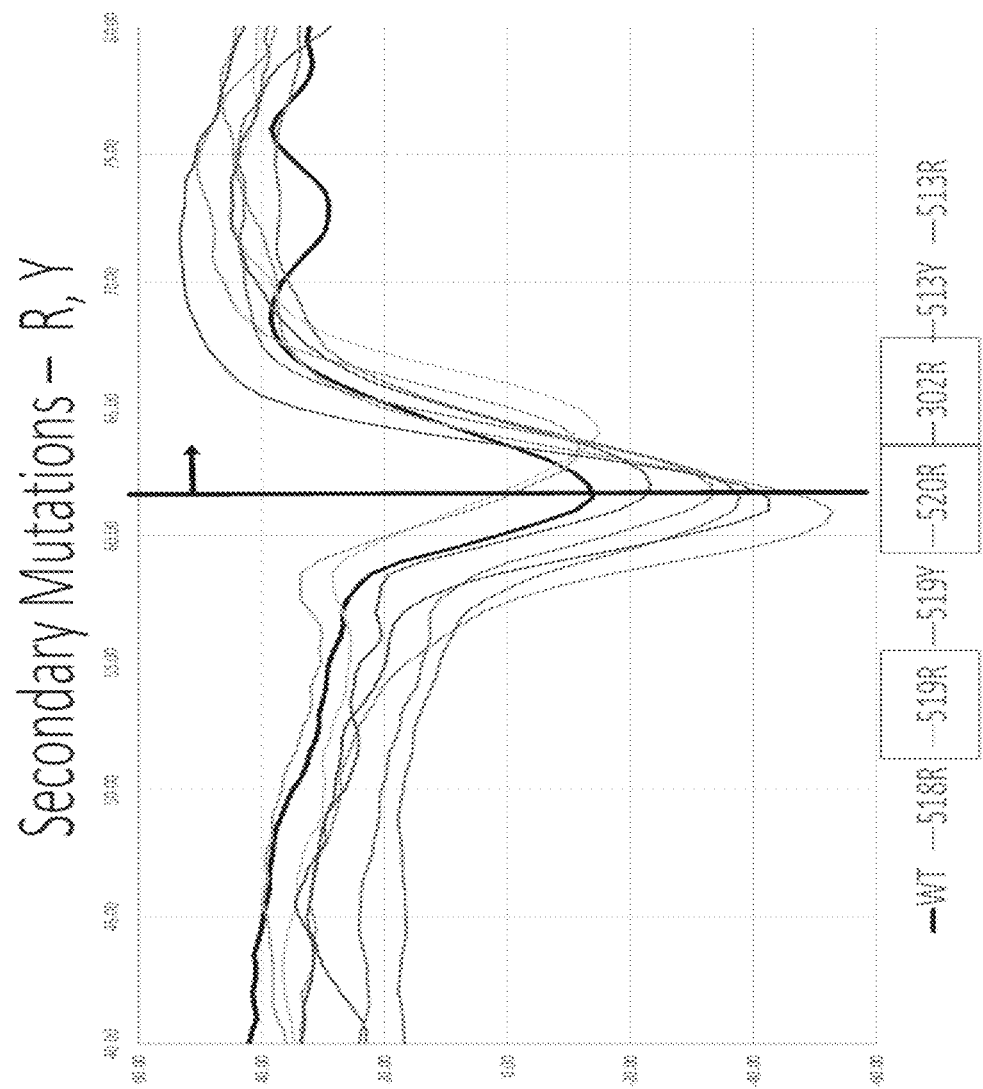
FIG. 40 depicts secondary mutations—R, Y. A shift of F519R (red arrow) as well as 302Y and 520R melting temp compared to WT in black. Using Glutamic acid and Glutamine did not result in positive interactions when used, so Applicants used Tyrosine and Arginine. Anything to the right of the line, the EC50 of WT, is improved thermal stability.

FIG. 40 depicts secondary mutations—R, Y. A shift of F519R (red arrow) as well as 302Y and 520R melting temp compared to WT in black. Using Glutamic acid and Glutamine did not result in positive interactions when used, so Applicants used Tyrosine and Arginine. Anything to the right of the line, the EC50 of WT, is improved thermal stability.

Figure 41:
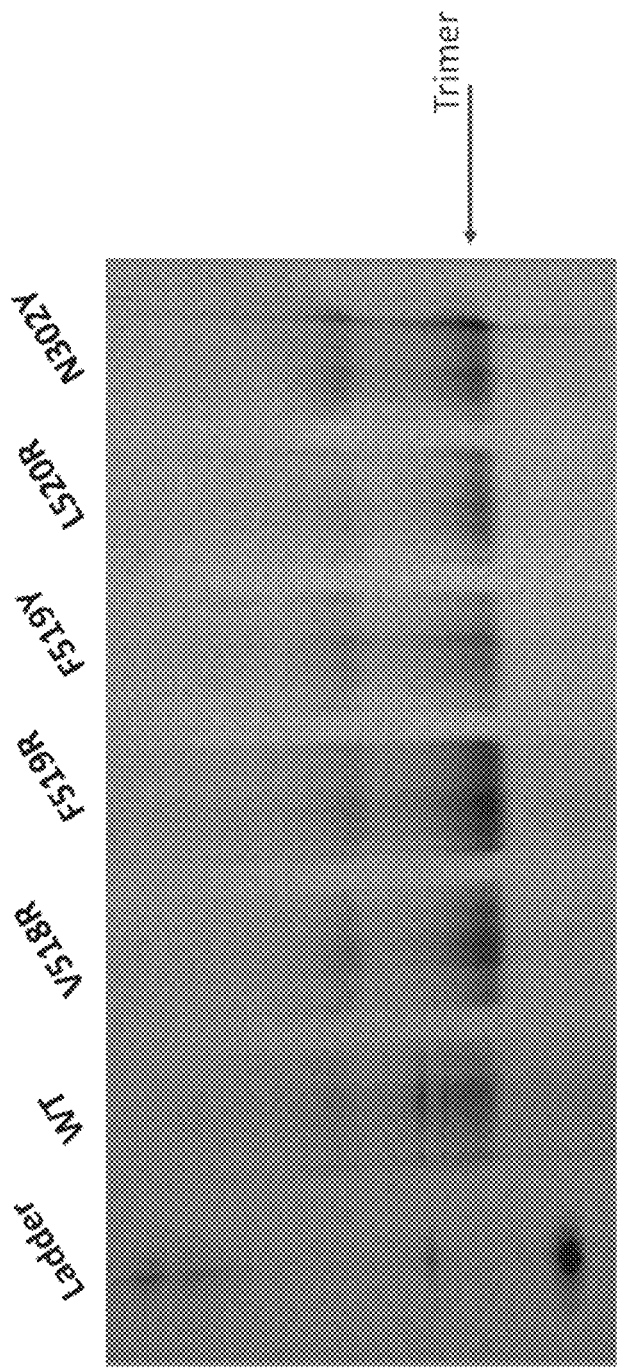
FIG. 41 shows that after making the secondary mutations, trimer formation was maintained, as well as an increase in stability.

FIG. 41 shows that after making the secondary mutations, trimer formation was maintained, as well as an increase in stability.

Figure 42:
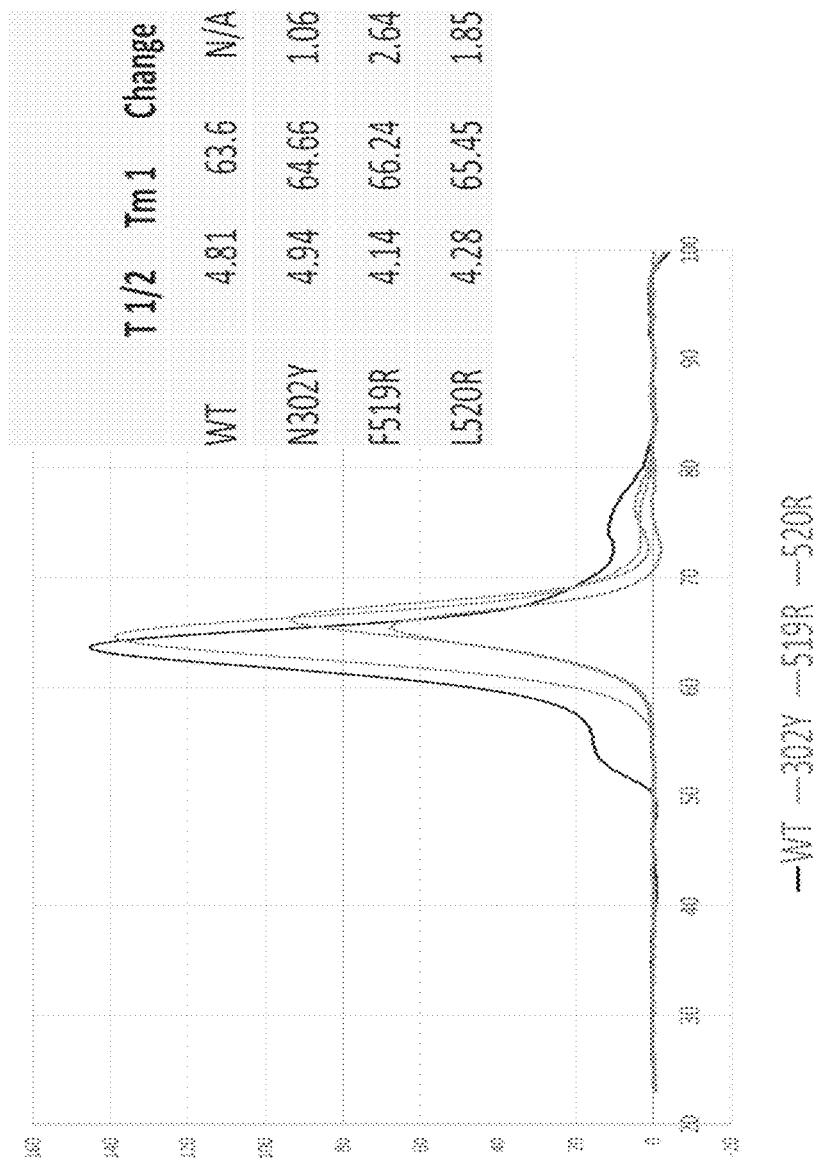
FIG. 42 depicts single mutation DSC. Mutations 302Y, 519R and 520R all supported trimer formation and gave an increase in melting temperature.
Figure 44:
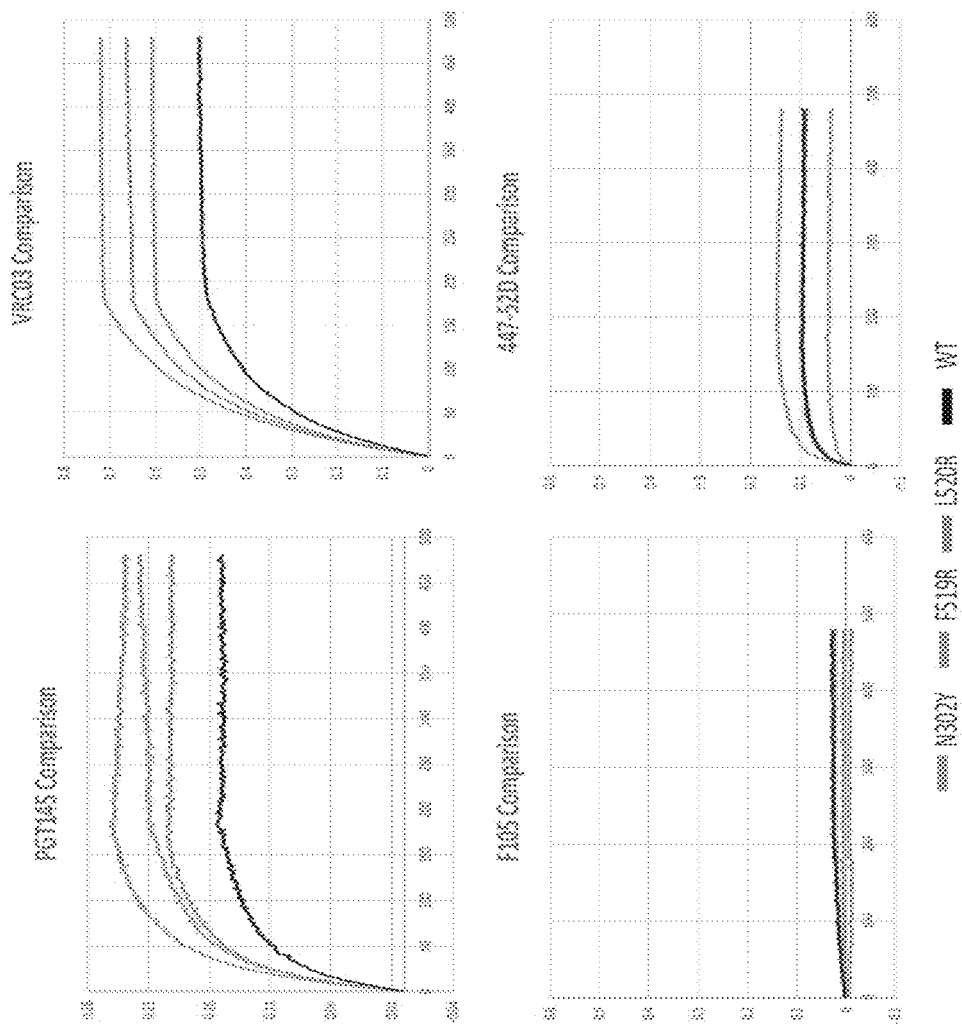
FIG. 44 depicts an octet binding analysis to show that all three mutations had the same binding profiles as wildtype, there was no improper binding. The 302Y mutation on the V loop decreased 447-52D binding.
Figure 45:
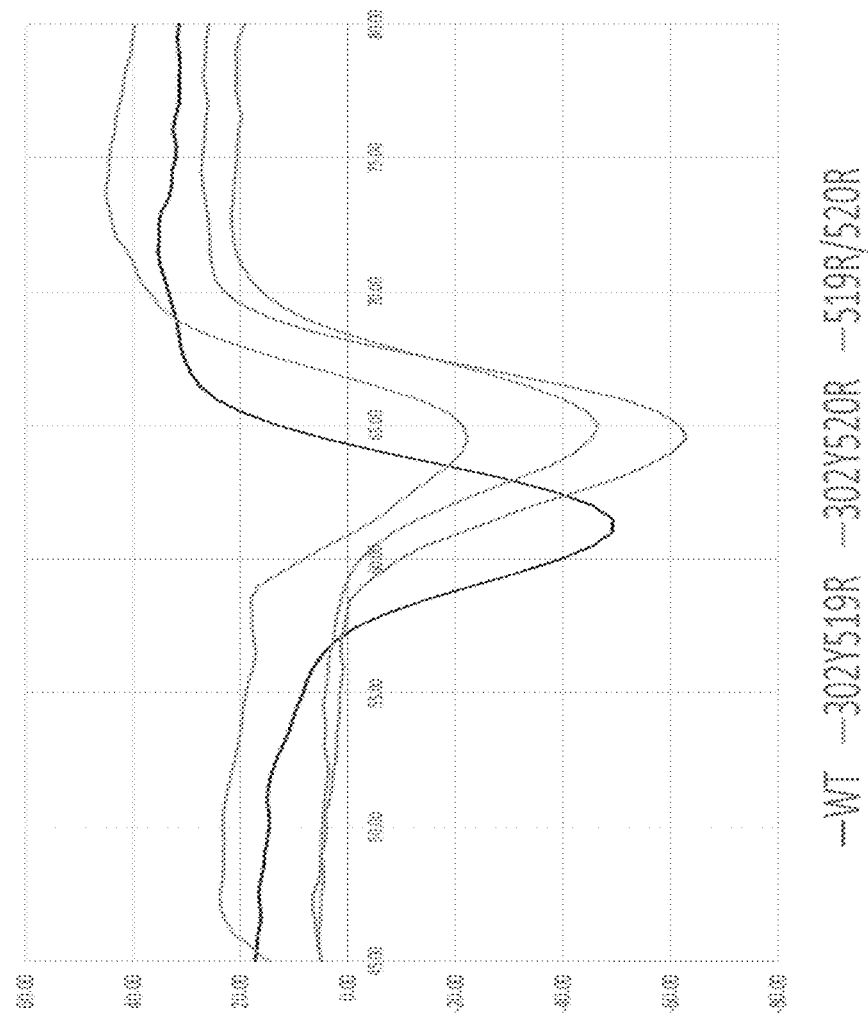
FIG. 45 depicts double mutant screening. The only issue with using DSF is that there tends to be a lower homogeneity compared to wildtype after just lectin chrom, but the DSC after SEC is used for actual results.
Figure 46:
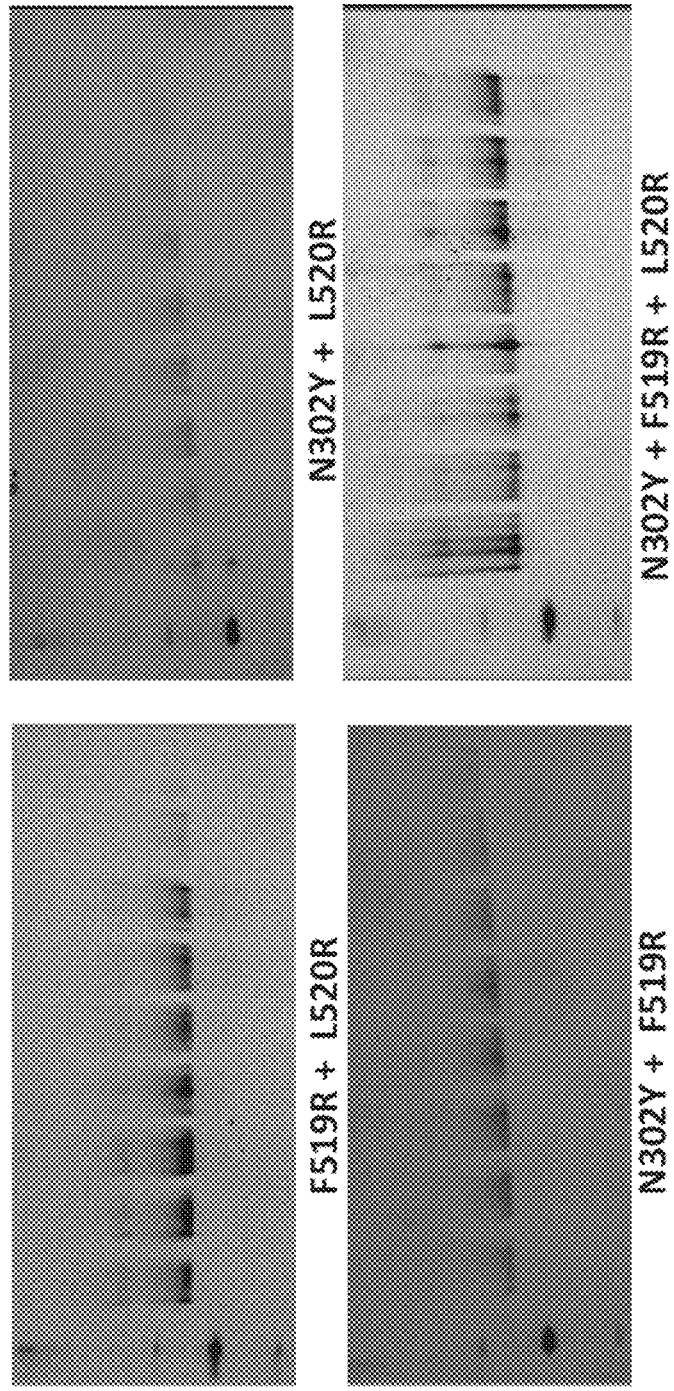
FIG. 46 depicts combination mutation SEC BNG. A lower load in 302Y/520 and 302Y/519 due to using only 100 mL transfection for SEC instead of the normal 1 L resulting in less protein.
Figure 47:
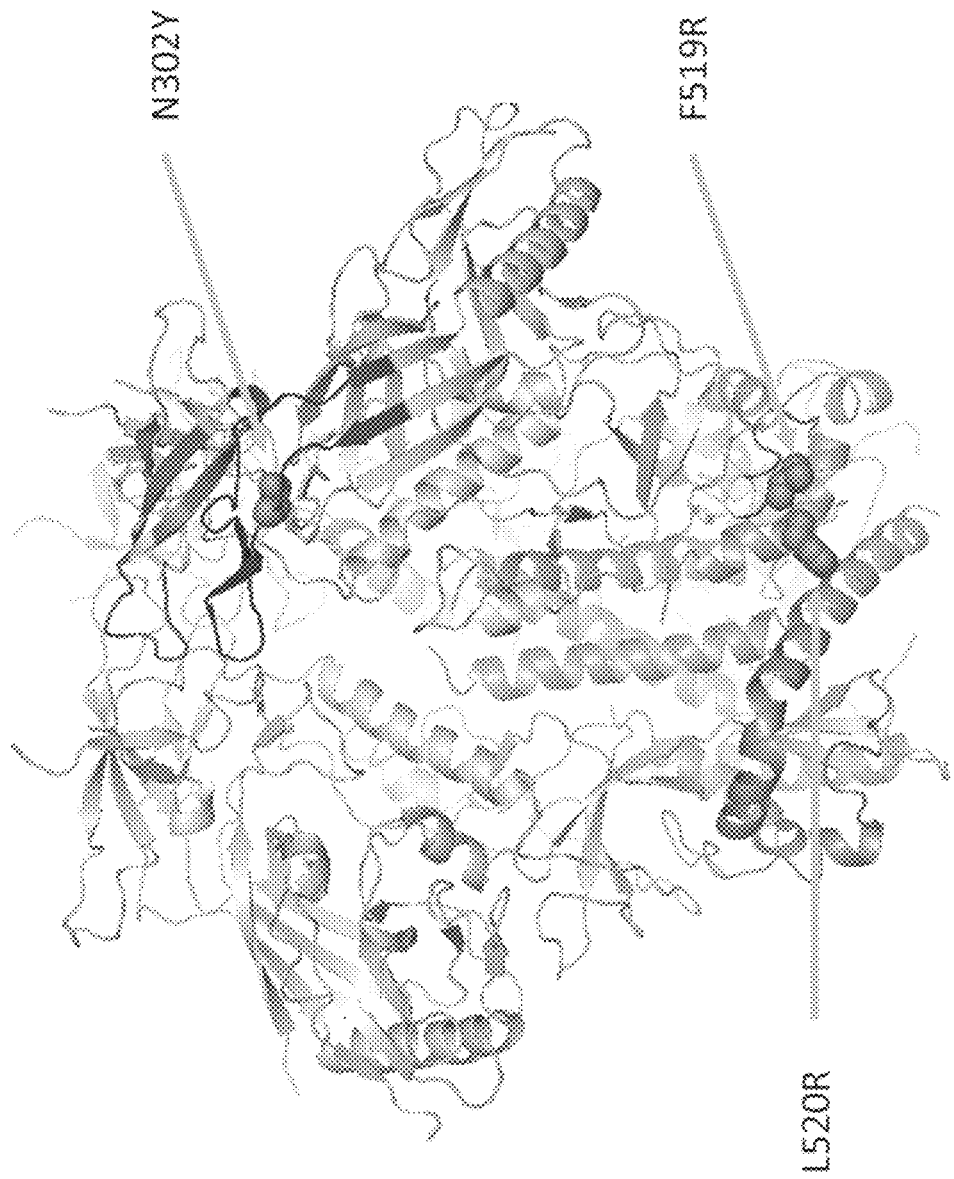
FIG. 47 shows highlighted in orange space filling are the three mutations that Applicants added together. Applicants predicted that N302Y stabilizes the V3 loop and that the 519 and 520 form a "cinch" using interchain interactions of a salt bridge and H bond.
Figure 48:
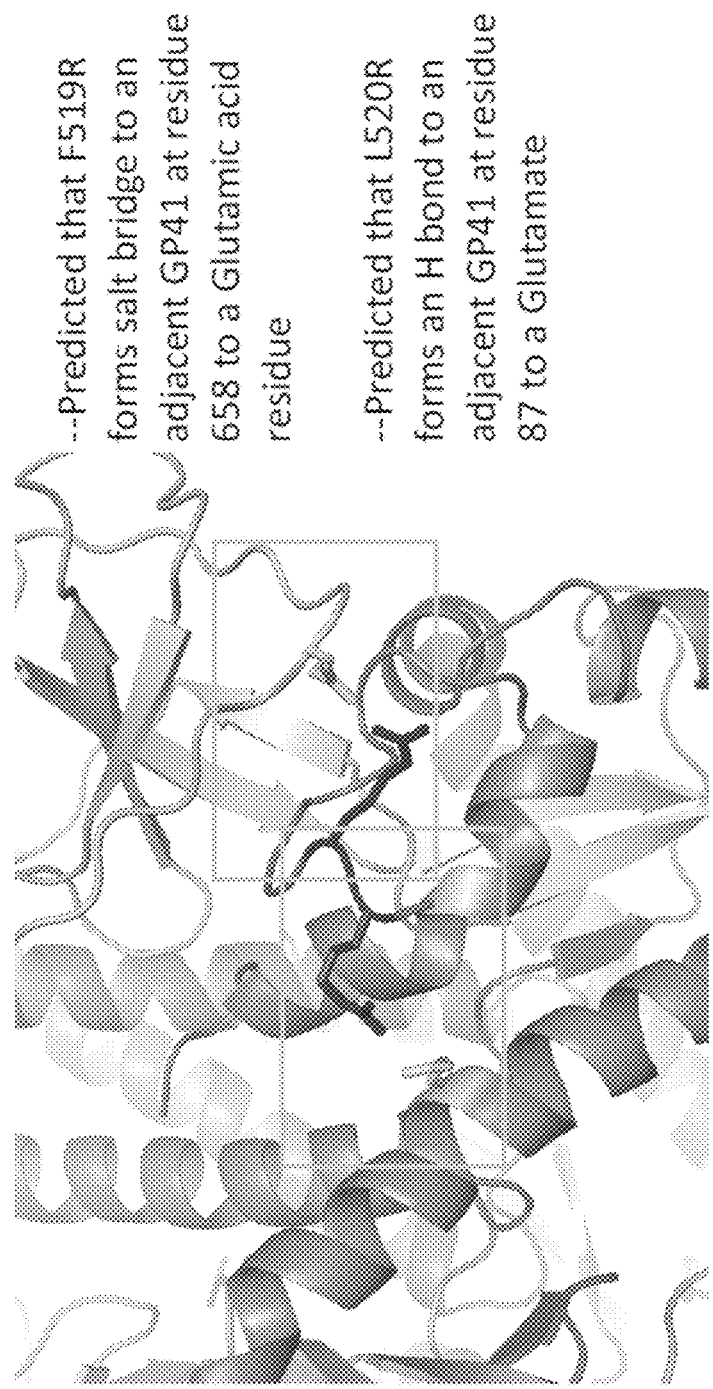
FIG. 48 depicts that 519 and 520 exist at the same time and form a "cinch" of interactions at the base of gp41, inter-chain bonds aid to stabilize.
Figure 49:
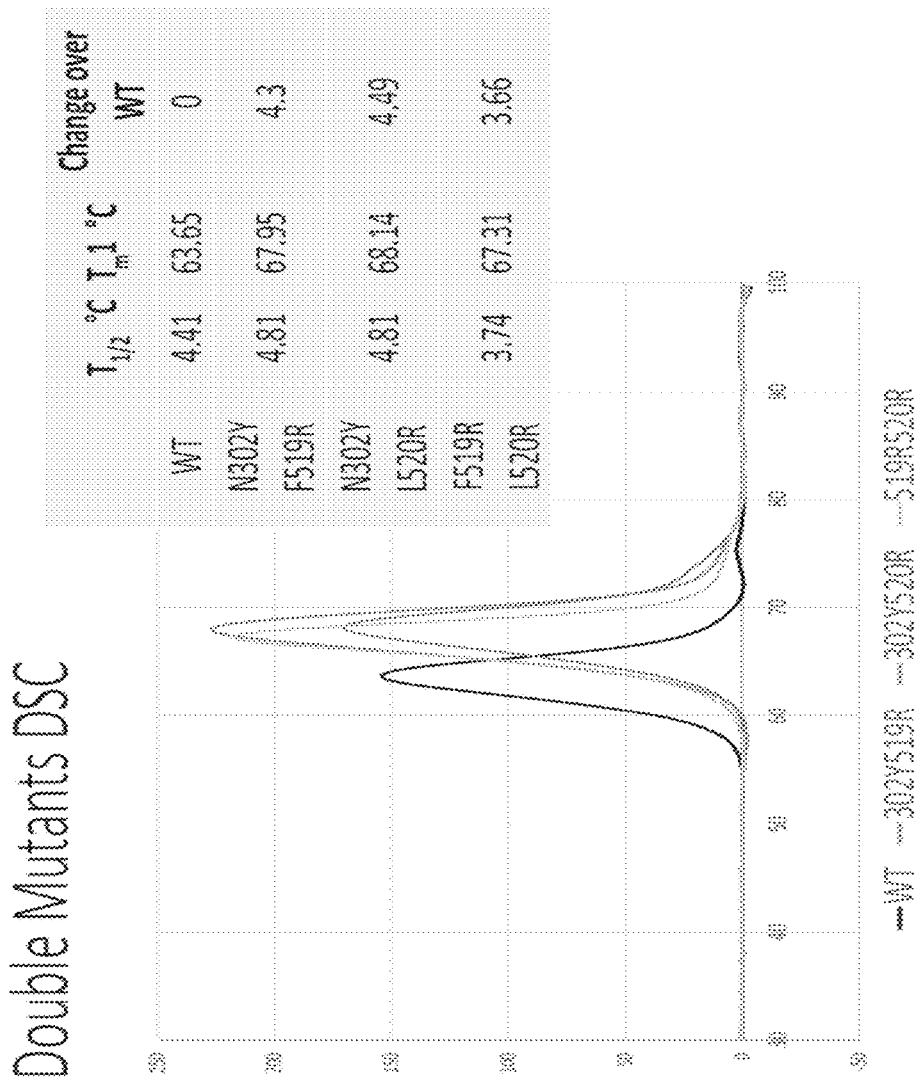
FIG. 49 depicts double mutants DSC. After doing the additive math, the combinations are not 100% additive to the increase in temperature.
Figure 50:
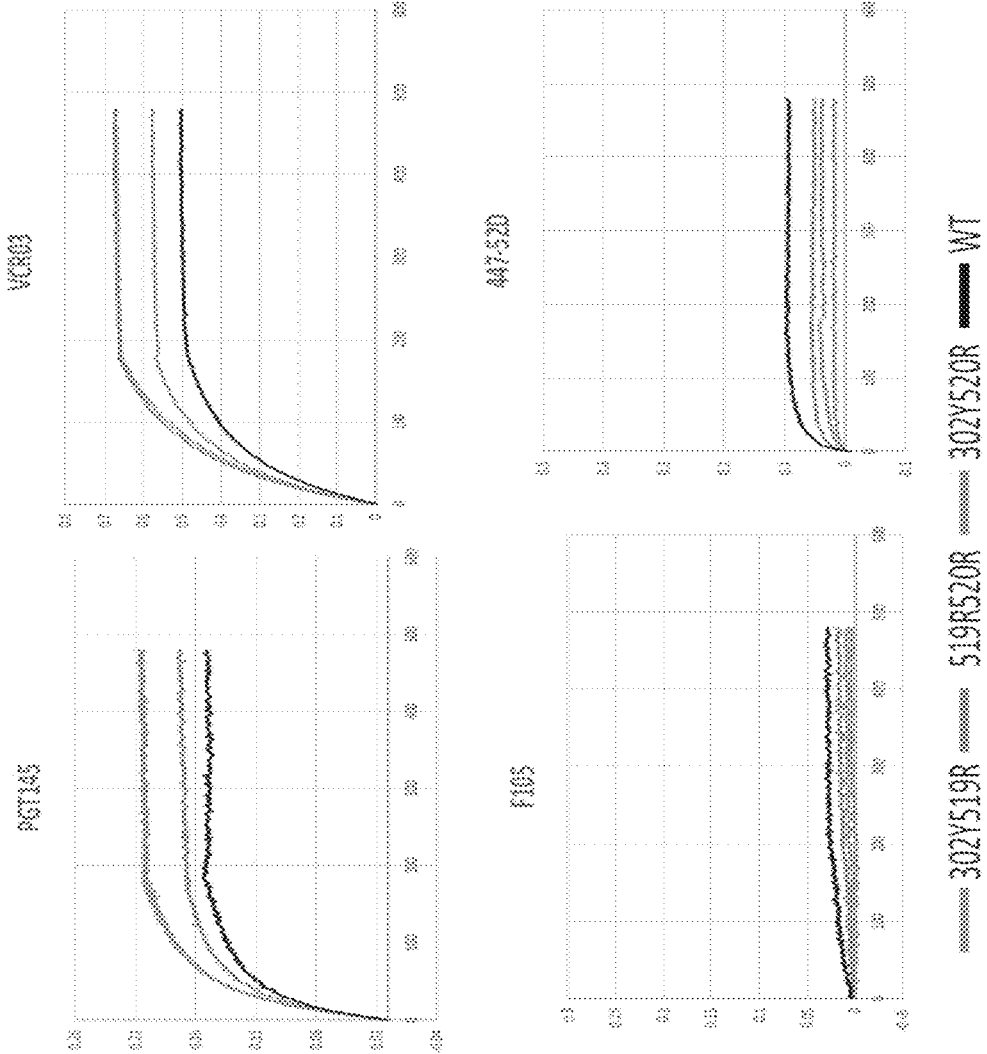
FIG. 50 depicts that mutants have better antibody binding to broadly neutralizing antibodies and worse binding to non neutralizing antibodies.
Figure 51:
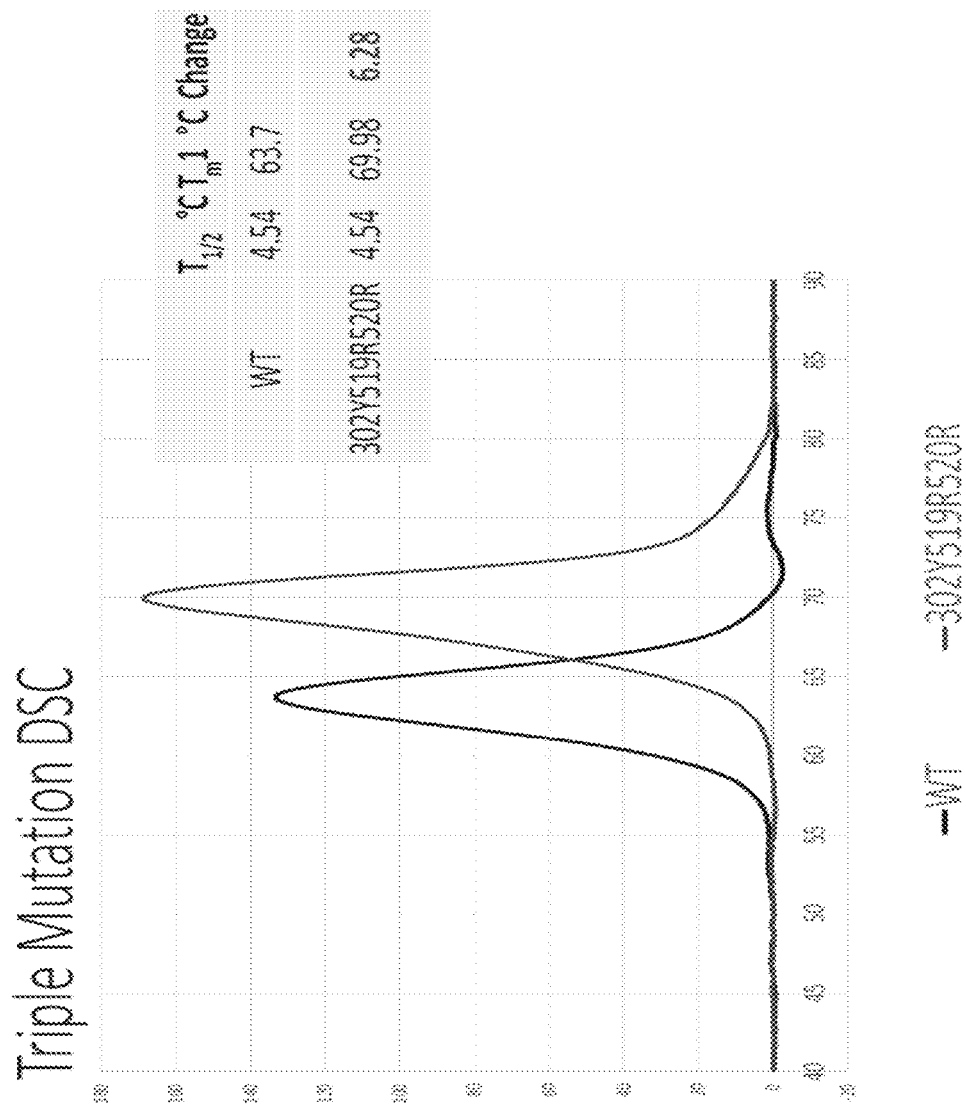
FIG. 51 depicts a triple mutation DSC.
Figure 52:
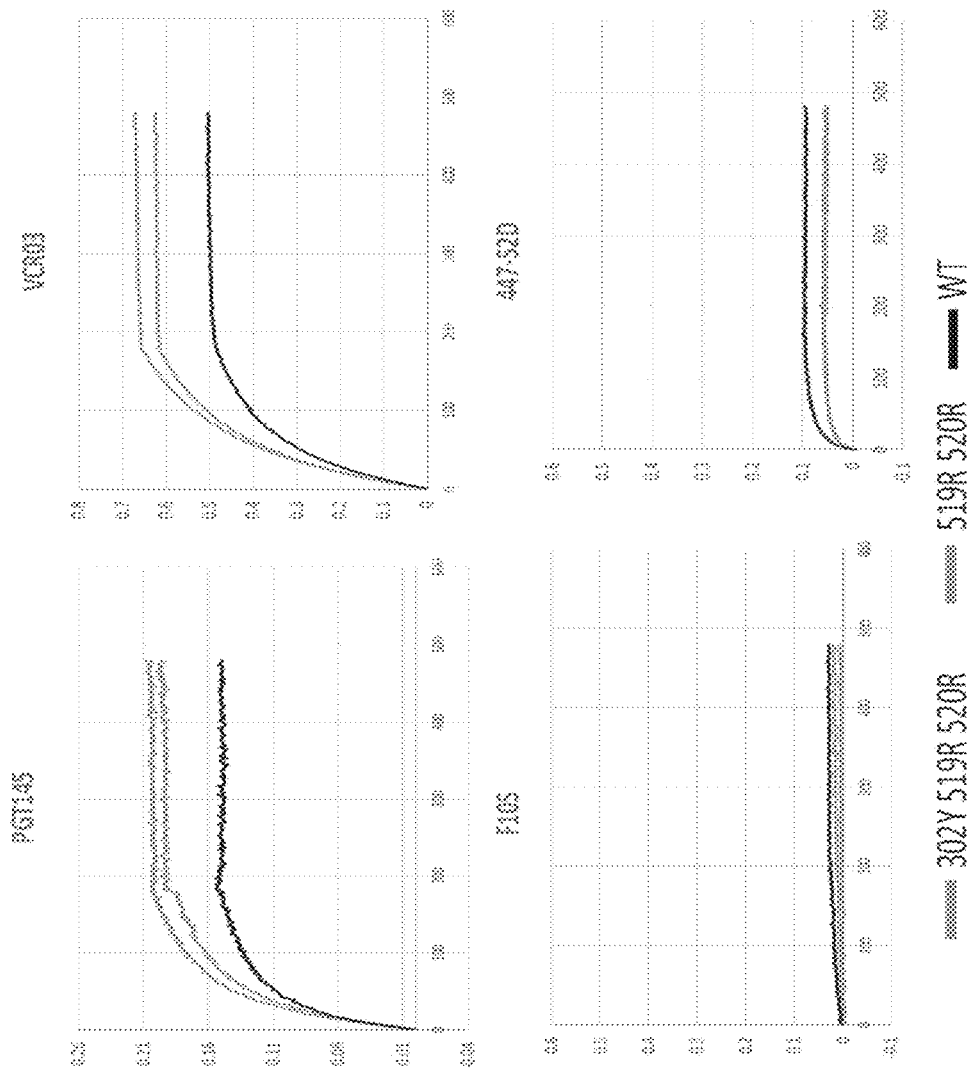
FIG. 52 depicts that the antibody binding profiles are nearly identical and yet the triple mutant has almost 2.6 degrees more stability.
Figure 54:
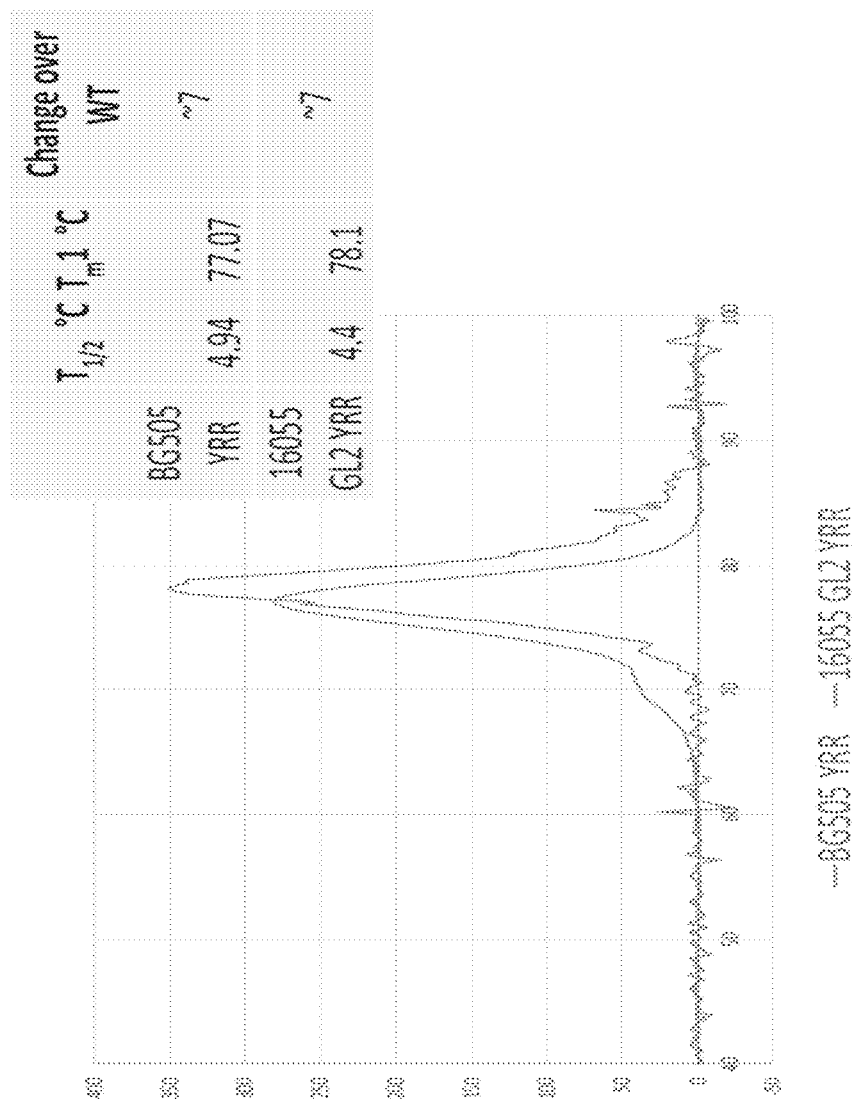
FIG. 54 depicts BG505 and 16055 YRR. The melting temp is still elevated beyond wild type.

FIG. 42 depicts single mutation DSC. Mutations 302Y, 519R and 520R all supported trimer formation and gave an increase in melting temperature.

FIG. 43 depicts single mutant SEC fractions which loaded too much protein so they look aggregated, but actually had solid purification profiles.

FIG. 44 depicts an octet binding analysis to show that all three mutations had the same binding profiles as wildtype, there was no improper binding. The 302Y mutation on the V loop decreased 447-52D binding.

FIG. 45 depicts double mutant screening. The only issue with using DSF is that there tends to be a lower homogeneity compared to wildtype after just lectin chrom, but the DSC after SEC is used for actual results.

FIG. 46 depicts combination mutation SEC BNG. A lower load in 302Y/520 and 302Y/519 due to using only 100 mL transfection for SEC instead of the normal 1 L resulting in less protein.

FIG. 47 shows highlighted in orange space filling are the three mutations that Applicants added together. Applicants predicted that N302Y stabilizes the V3 loop and that the 519 and 520 form a "cinch" using interchain interactions of a salt bridge and H bond.

FIG. 48 depicts that 519 and 520 exist at the same time and form a "cinch" of interactions at the base of gp41, inter-chain bonds aid to stabilize.

FIG. 49 depicts double mutants DSC. After doing the additive math, the combinations are not 100% additive to the increase in temperature.

FIG. 50 depicts that mutants have better antibody binding to broadly neutralizing antibodies and worse binding to non neutralizing antibodies.

FIG. 51 depicts a triple mutation DSC.

FIG. 52 depicts that the antibody binding profiles are nearly identical and yet the triple mutant has almost 2.6 degrees more stability.

FIG. 53 depicts an analysis that shows there is not a direct translation of additive effects as Applicants assumed but Applicants assume synergistic effects are causing the enhanced melting temps.

FIG. 54 depicts BG505 and 16055 YRR. The melting temp is still elevated beyond wild type.

Applicants conclude that 302Y 519R and 520R can all contribute together to improve the melting temperature of JRFL-NFL-TD15-CC by 6.28° C. without sacrificing homogeneity in the trimer formation product and suggest these mutations are applicable in other clades.

Example 3: High-Density Array of Well-Ordered HIV-1 Spikes on Synthetic Liposomal Nanoparticles Efficiently Activate B Cells A major step towards an HIV-1 vaccine is an immunogen capable of inducing neutralizing antibodies. Envelope glycoprotein (Env). mimetics, such as the NFL and SOSIP designs, generate native-like, well-ordered trimers and elicit tier 2 homologous neutralization (SOSIPs). Applicants reasoned that the display of well-ordered trimers by high-density, particulate array would increase B cell activation compared to soluble trimers. Here, Applicants present the design of liposomal nanoparticles displaying well-ordered Env spike trimers on their surface. Biophysical analysis, cryo- and negative-stain electron microscopy and binding analysis with a panel of broadly neutralizing antibodies confirm high-density, well-ordered trimer particulate array. The Env trimer-conjugated liposomes were superior to soluble trimers in activating B cells ex vivo and germinal center B cells in vivo. In addition, the trimer-conjugated liposomes elicited modest tier 2 homologous neutralizing antibodies. The trimer-conjugated liposomes represent a promising initial lead towards the development of more effective HIV vaccine immunogens.

A broadly effective HIV-1 vaccine will likely require the elicitation of broadly effective neutralizing antibodies. Although broadly neutralizing antibodies (bNAbs) arise sporadically following chronic HIV infection such bNAbs are exceedingly difficult to elicit by vaccination (Burton et al., 2004). One roadblock to the elicitation of neutralizing antibodies by vaccination has been the development of an immunogen that stably presents a gp120-gp41 envelope glycoprotein (Env) trimer in its native state, as it is presented on the virus surface. With the recent developments of SOSIP and NFL trimeric Env platforms, it is now possible to express and purify soluble, native-like and well-ordered Env trimers that are structurally and antigenically well characterized (Guenaga et al., 2015; Julien et al., 2013; Pancera et al., 2014; Sharma et al., 2015). To date, these trimeric mimetics of the HIV-1 native spike elicit homologous "tier 2" neutralization to a few selected strains of undetermined long-term durability (Sanders et al., 2015) and most potently in small animals. Although this is a promising first step, the next step is to quantitatively or qualitatively increase B cell activation elicited by the well-ordered trimers, toward the longer-term goals of increased somatic hypermutation and more durable antibody responses leading to trimer-dependent elicitation of broader neutralizing activity.

An impediment to elicit neutralizing antibodies by HIV itself or HIV-based virus-like particles (VLP) may be the low levels of natural Env incorporation, resulting in sparse numbers of spikes per VLP (Deml et al., 1997). Here, Applicants generated Ni+2-bearing, fully synthetic single bilayer liposomes arrayed with the newly developed, well-ordered HIV-1 soluble trimer mimetics possessing three C-terminal His-tags per trimer. This design allows the variable incorporation of Ni+2-lipids to generate a series of JRFL trimer-conjugated liposomes displaying different levels of either SOSIP or NFL well-ordered (Kovacs et al., 2014; Sanders et al., 2013; Sharma et al., 2015) trimers arrayed on the liposomal surface. This means of high-density particulate display as well blocks access to the non-neutralizing, non-glycosylated underside of the trimers. This solvent accessible surface, usually occluded by the viral lipid bilayer, was recently shown to be highly immunogenic using soluble BG505 SOSIP trimers (Hu et al., 2015) in mice, however no "tier 2" autologous neutralizing antibodies were detected as they are in rabbits (Sanders et al., 2015). HIV gp140 trimers conjugated to interbilayer-cross-linked multilamellar vesicles (ICMVs) generate high titer binding responses in mice (Pejawar-Gaddy et al., 2014) and biotin-labeled gp120 onto avidin-containing liposomes stimulate anti-gp120 B cells in vitro(Ota et al., 2013), however well-ordered Env trimers arrayed at high-density particulate array have not been assessed in an animal model capable of generating tier 2 autologous neutralization.

In the current study, Applicants showed by biochemical and biophysical analysis, cryo-electron microscopy (EM) and negative staining-EM that the predominantly single bilayer liposomes, when optimized, present the well-ordered trimers with high-density, multi-valent array. On the liposome surface, these well-ordered trimers retained qualities of a closed native trimer and were stable for several months at 4° C. Applicants demonstrated that this high-density array better activated B cells ex vivo compared to strain-matched soluble trimers and that the liposome-conjugated trimers more efficiently generated germinal center B cells compared to soluble trimers in a statistically significant manner. Compared to the soluble trimers, there was a trend for the liposome-conjugated trimers to more efficiently elicit binding antibodies to native-like trimers and modest tier 2 (JRFL) homologous neutralizing titers. The clinical efficacy of human papillomavirus (HPV) L1 virus-like particles (VLPs) to provide long-lasting protection against a virus that enters by mucosal routes, while, in contrast, the HPV L1 monomer is not protective suggests that particulate display of ordered HIV trimers might hasten development toward a more effective HIV-1 vaccine (Caldeira Jdo et al., 2010; Safaeian et al., 2013), (Schiller and Chackerian, 2014; Schiller and Lowy, 2015). Combining the well-ordered trimers with particulate high-density display presents a scalable platform to enhance B cell responses to HIV-1 Env and potentially to envelope glycoproteins from other viruses that are relevant vaccine targets.

Well-Ordered His-Tagged Trimers for Liposomal Array.

Figure 55A:
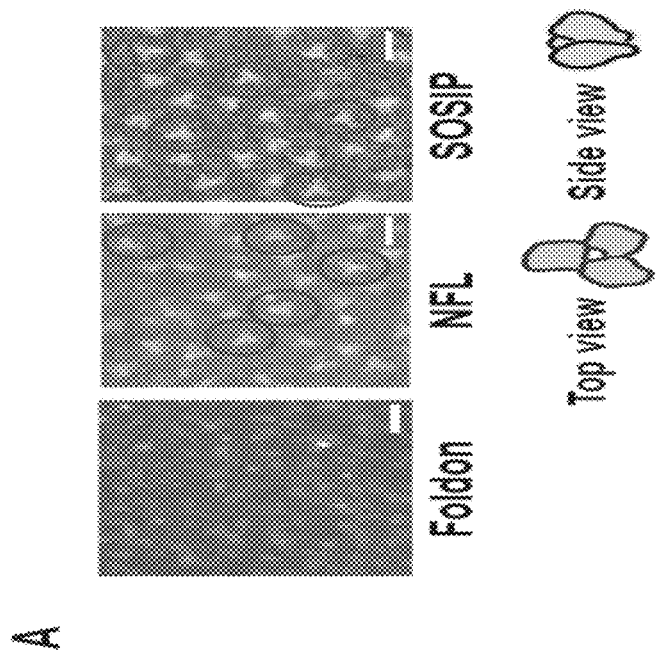
FIGS. 55A-B depict HIV trimers and their particulate display. (A) Negative stain EM micrographs of JRFL gp140-foldon oligomers, JRFL NFL2P, and JRFL SOSIP trimers. Scale bars=20 nm. (B) Schematic representation of liposomes displaying HIV-1 trimers. Zoomed field depicts binding of the 6-histidine repeats (His6 tag (SEQ ID NO: 3)) present as a fusion on the C-terminus of each protomer of each trimer to the Ni+2 chelated at the hydrophilic head group of the DGS-NTA(Ni) polar lipid.
Figure 55B:
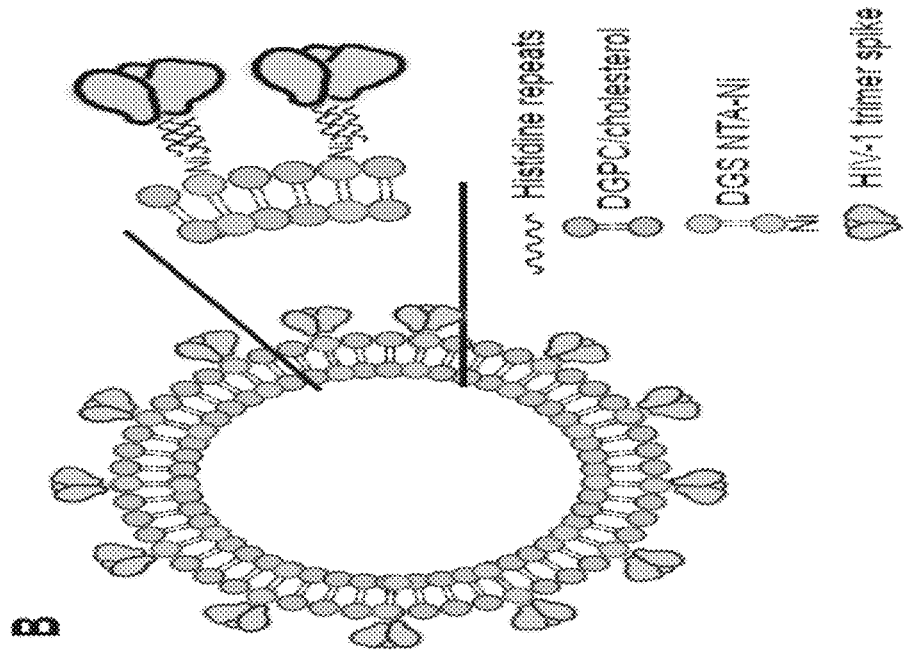

The development of well-ordered trimers by two independent platforms, SOSIP and NFL, present the opportunity to assess the multivalent array of such trimers on the surface of liposomal nanoparticles to study their impact on antigenicity and immunogenicity. These well-ordered trimers are well characterized by negative stain followed by EM at both the level of 2D classifications and 3D reconstructions, including the JRFL strain-derived trimer prototypes used here (Guenaga et al., 2015; Sharma et al., 2015). To contrast the ordered appearance of the JRFL SOSIP and NFL trimers with the previously described disordered foldon trimers (Ringe et al., 2015; Tran et al., 2014) Applicants performed negative staining followed by EM at the level of resolution amenable for analysis of liposomes. As shown in FIG. 55A (left panel), the previously described JRFL-based gp140-foldons displayed an amorphous mixture of oligomeric states. In contrast, the more faithful mimetics of the HIV-1 Env spike, JRFL SOSIP and NFL trimers, presented a relatively well-ordered appearance. Depending upon the random orientation of the trimers on the carbon-coated grid, the soluble spikes displayed 3-fold symmetry typified by a "propeller-like" appearance by negative staining-EM, at the level of resolution analyzed here (FIG. 55A, center and right panels). With the well-ordered trimers in hand, each containing C-terminal His6-tags (SEQ ID NO: 3) on each protomeric subunit, Applicants sought to array these spike mimetics on a repetitive, nanoparticle platform to assess potential improvements in B cell activation and immunogenicity. Applicants generated liposomes by standard procedures comprised of a mixture of 60% 1,2-distearoyl-sn-glycero-3-phosphocholine (DGPC) and 40% cholesterol (Avanti Polar Lipids). Applicants used a relatively high concentration of cholesterol to increase liposomal membrane stability and integrity in vivo (Arsov and Quaroni, 2007). In brief, polar lipids in chloroform were dried onto glass, re-suspended in aqueous buffer, sonicated in the buffer and extruded through filters to generate approximately 100 nm diameter nanoparticles. To produce His-binding liposomes, Applicants incorporated 1,2-dioleoyl-sn-glycero-3-((N-(5-amino-1-carboxypentyl)iminodiacetic acid)succinyl) (nickel salt) (DGS-NTA-Ni) into the lipid mixture at levels of 1 to 4%, substituting for the cholesterol lipid component. Applicants reasoned that the NTA-Ni would randomly disperse in the lipid bilayer, and that approximately 50% of the time, the polar head groups would align on the outside of the lipid bilayer to be available for conjugation with the His-tags present on the C-terminus of the ordered HIV-1 trimers (see schematic, FIG. 55B). Applicants could also incorporate TLR ligands into the liposomes by including them in the chloroform mixture prior to drying the lipids on to the glass surface.

Analysis of Well-Ordered Trimers Coupled to Liposomes by SDS-PAGE and EM.

Following incubation of the well-ordered NFL and SOSIP His-tagged trimers with the Ni-bearing liposomes, containing 1, 2 and 4% DGS-NTA(-Ni) lipids, respectively, Applicants performed size exclusion chromatography (SEC) to separate free trimers from liposomes. Next, Applicants analyzed the liposomes by SDS-PAGE and detected increasing trimer bands with increasing levels of Ni+2 incorporated into the liposomes following staining of the gel by Commassie blue solution (FIG. 56). Applicants subjected the 4% DGS-NTA (Ni) liposomes to dynamic light scattering (DLS) to assess liposomal diameter and uniformity before and after conjugation with the well-ordered NFL or SOSIP trimers. As shown in FIG. 56B, the non-conjugated liposomes displayed an average diameter of 152 nm while the average diameter of trimer-conjugated liposome was 172 nm. To further assess liposome uniformity, diameters and to visually determine state of trimers arrayed on the surface of the liposomes, Applicants performed cryo-EM of both the JRFL SOSIP- and JRFL NFL-conjugated 4% DGS-NTA(Ni) liposomes (FIG. 56 and FIG. 62A). Using the cryo-EM images, Applicants measured the liposome diameters to be from 75 nm to 250 nm (see FIG. 62B), consistent with the DLS data. Using the measuring tools, Applicants determined the lipid bilayer to be ~5 nm in width with individual trimers spaced at ~12-14 nm apart on the liposomes. As detected by the cryo-EM analysis, the majority of liposomes possessed a single lipid bilayer and virtually all nanoparticles displayed a high-density array of the SOSIP or NFL trimers, respectively. An apparent double lipid bilayer was visible on a small percentage of liposomes and, for even fewer, multiple layered lipid bilayers were observed (FIG. 62A), all possessing trimers on their outermost surface. The liposome interior appeared to contain only buffer as no other density was observed in the enclosed volumes. In addition, no other materials were observed in the sample, indicating that the sample was free of any adventitious agents.

To increase contrast and resolution of the trimers arrayed on the liposomal surface, Applicants performed negative staining followed by EM at selected magnifications of the trimer-conjugated liposomes. As seen in FIG. 57, with 1% Ni-lipid formulation, the conjugated well-ordered trimers were detected as a "ring" visible around the circumference of the liposomes, observable by EM in what appeared to be two dimensions. In the case of the 2% Ni-containing liposomes, beside trimers ringing the circumference of individual nanoparticles, trimers could be detected on the surface of the liposomes encircled by the lipid bilayer. For the 4% Ni-containing liposomes, Applicants observed densely packed and evenly spaced trimers arrayed on the surface of the liposomes by the negative staining-EM. The patterns of trimer array were very similar for both the JRFL SOSIP- and JRFL NFL Env-containing liposomes. Because the trimers were relatively well resolved, Applicants next quantitated the approximate number of trimers per liposomal field by constructing a grid to aid manual counting (see FIG. 57B). The total number of trimers per visible field was in the range of 300 spikes per liposome, likely an underestimate since not all surfaces of the liposome are observable in these EM images. Using iTEM (EMSIS, GMbH) measuring tools, Applicants determined the relatively uniformly arrayed trimers to be spaced approximately 14-15 nm apart, center-to-center, on the surface of the nanoparticles (see FIG. 57C and FIG. 57D). In addition, Applicants constructed a square area of approximately 12 nm per side that would encompass each trimer, and adjacent unoccupied surface area, to circumscribe an area of ~144 nm2. Applicants calculated the surface area of a spherical liposome with a radius of ~75 nm to be 70,865 nm2 and by simple division would yield ~492 trimers per liposome, bracketing an estimated range between 300 and 500 trimers per particle.

To confirm that trimer conjugation to the liposomes was Ni-dependent, DGPC liposomes without any Ni-lipid were generated and the JRFL SOSIP trimers were added to assess interaction. Most trimeric glycoprotein remained dissociated from the liposomal fraction by SEC and EM further confirmed that no trimers were associated with the Ni-lacking liposomes (FIG. 63A).

Binding Analysis of the Liposome Bound Trimers by Biolayer Light Interferometry (BLI) and EM.

Applicants next assessed if the well-ordered trimers maintained quaternary packing on the surface of the liposomes by probing the trimers with selected bNAbs and mAbs using BLI. Accordingly, Applicants captured the trimer-conjugated liposomes on the Octet sensor surface by wheat germ agglutinin (WGA), which recognizes and binds to carbohydrates that are abundant as N-glycans located on the trimeric spike surface. In this format, due to the dense array of the trimers on the liposomal surface, there will be avidity effects in regards to the bivalent IgGs as analytes, therefore Applicants used the BLI binding analysis not to derive actual affinities, but to qualitatively assess relative avidities to confirm that once the trimers were conjugated to the liposomes, they displayed the same binding pattern as assessed previously by more quantitative binding kinetics (Guenaga et al., 2015; Sharma et al., 2015). Using the WGA capture of the trimer-conjugated lipoosomes, Applicants did attempt binding by selected Fabs to obtain affinities, but due to the smaller mass of the Fab relative to the liposomes, Applicants could not detect reliable signals by this approach, so Applicants proceeded with the qualitative binding assessments using bivalent IgG.

To begin the avidity analysis, Applicants assessed recognition by the CD4 binding site-directed bNAb, VRC01(Wu et al., 2011) and the glycan-dependent 2G12, to determine overall levels of liposome-conjugated trimers, since these mAbs can recognize trimeric or monomeric forms of HIV Env (FIG. 58A). The VRC01 and 2G12 bNAbs efficiently recognized the trimers conjugated to the liposomes, consistent with previous binding studies, and the EM analysis presented here,as did the other CD4bs-directed bNAbs PGV04 (Falkowska et al., 2014), CH103 (Liao et al., 2013) and b12 (Burton et al., 1994). Applicants then utilized the trimer-specific, V2-directed bNAb, PGT145 (McLellan et al., 2011), to confirm that, following conjugation, the quaternary variable region cap of the trimers remained intact. As expected, the trimer-specific PGT145 bNAb efficiently recognized the trimers arrayed on the liposomal surface as did other trimer-preferring bNAbs such as VRC03 (Li et al., 2012; Tran et al., 2012), VRC06 (Li et al., 2012), PGDM1400 (Sok et al., 2014) and PG16 (Pejchal et al., 2010) (FIG. 58A). In contrast, the V3 loop specific mAb, 447-52D (Stanfield et al., 2004), did not bind to the JRFL NFL or JRFL SOSIP trimers on the liposomes, indicating that the V3 region of these trimers is not accessible when arrayed on the liposomal surface. These results contrast with the BLI binding data shown here (FIG. 64A), and previously published data (Sharma et al., 2015) that were generated with the JRFL ordered trimers in solution and 447-52D on the sensor surface. In this configuration, the well-ordered JRFL trimers were well recognized by the V3-directed mAb. To confirm this result in the same binding format used for the liposomes, Applicants assessed 447-52D recognition of the JRFL SOSIP and JRFL NFL trimers when they were captured on the WGA sensors. In this context, 447-52D recognized the trimers, indicating occlusion of the V3 region occurs only when the trimers are arrayed on the liposomal surface. The non-neutralizing mAb, F105 (Posner et al., 1993), does not efficiently recognize the soluble JRFL NFL or SOSIP trimers (Guenaga et al., 2015; Sharma et al., 2015) (FIG. 58A and FIG. 64B), but does efficiently recognize disordered trimers, such as foldon (Guenaga et al., 2015; Sharma et al., 2015). Here, F105 did not recognize the liposome-conjugated trimers as assessed by BLI, indicating the maintenance of a well-ordered trimeric state following liposomal conjugation (FIG. 58A and FIG. 64C). Since the previous affinities using selected bNAbs were not determined by WGA capture but by His-tag capture of the JRFL trimers (Guenaga et al., 2015; Sharma et al., 2015), Applicants performed a comparative binding analysis with most of the antibodies used to probe the trimer-conjugated liposomes to confirm the relative rank order of the antibody avidities to the trimers and the apparent occlusion of V3 on the trimer-conjugated liposomes (FIG. 58A).

Applicants then probed both JRFL SOSIP and NFL trimers arrayed on the 2% DGS-NTA(Ni)-lipid-containing liposomes with a subset of Env-directed antibodies, but now qualitatively analyzed by negative stain EM, to determine relative accessibility of the neutralizing and non-neutralizing epitopes once the trimers are coupled to the solid phase. Consistent with the binding analysis, when the Env trimer-conjugated liposomes were incubated with non-neutralizing F105 mAb, in excess, there was no detectable binding to the ordered trimers compared to the uniganded control trimer-conjugated liposomes (FIG. 58B and FIG. 64D). In stark contrast, when the glycan-directed bNAb, 2G12 (Trkola et al., 1996) was incubated with the trimer-conjugated liposomes, the propeller-like pattern of the well-ordered trimers was noticeably perturbed by this full IgG. Similarly, but with less disruption of trimer symmetry, PGV04 and PGT145 binding to the trimers could be observed following incubation and negative stain EM (FIG. 58B and FIG. 64D).

Stability of Trimer-Conjugated Liposomes at Selected Temperatures by EM.

Applicants next sought to determine the stability of the trimer-conjugated liposomes in aqueous buffer at both 4° C. and 37° C. Accordingly, Applicants stored the liposomes at 4° C. for an extended period of time and assessed overall conformation by negative stain EM. Both the liposomes and the trimers arrayed on the surface of these nanoparticles were very stable for up to 4 months at 4° C. (FIG. 63B). Applicants performed the same analysis of trimer-bound liposomes stored at 37° C. and detected more of an impact on both the liposomes and trimers on the surface of the liposomes. In brief, approximately 50% of trimers were lost from the liposomal surface over a period of 7 days when stored at 37° C. (FIG. 63C).

Trimer-Conjugated Liposomes are More Efficient at Activating B Cells than Soluble Trimers.

Figure 59A:
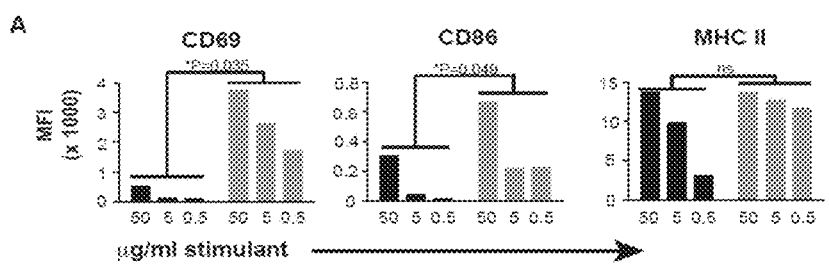
Figure 59B:
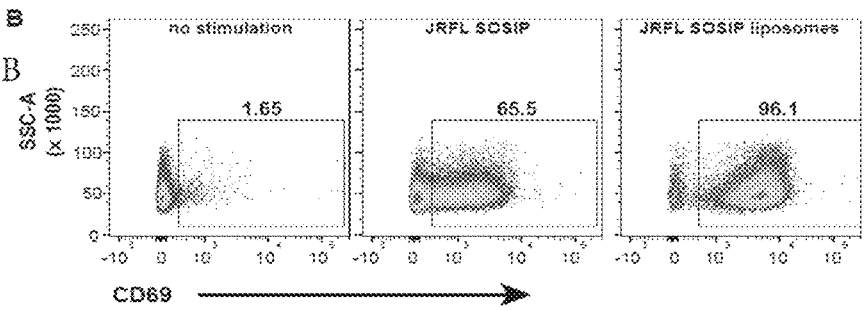
Figure 59C:
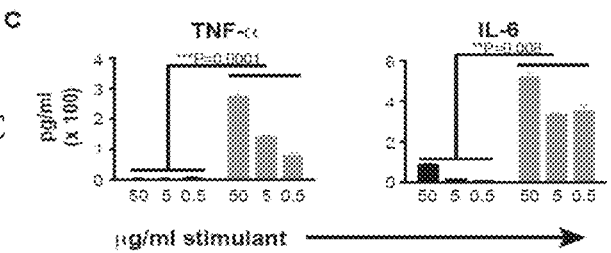
Figure 59D:
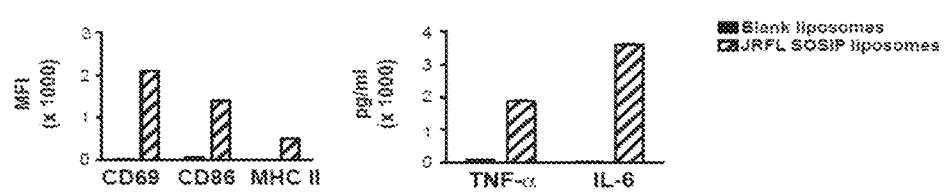
Figure 65A:
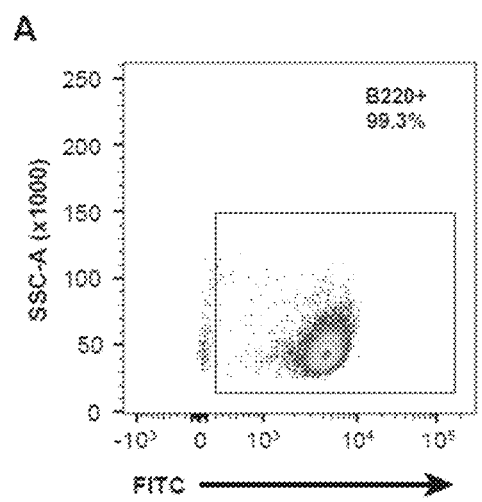
FIGS. 65A-B depict purity of isolated B cells. Splenocytes from b12 knock-in mice were negatively selected for B cells and stained for cell surface markers (A) B220 and (B) CD19.
Figure 65B:
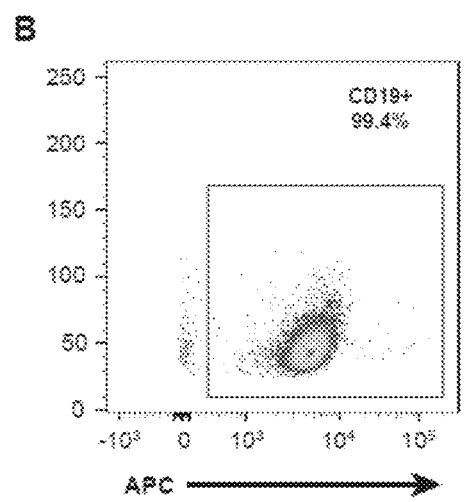

Next, Applicants determined if the well-ordered trimers on the liposomes were able to activate B cells following BCR engagement. For this purpose, Applicants used B cells isolated by negative selection from the previously described mature b12-expressing knock-in mice (Ota et al., 2013). The B cells were over 99% pure as characterized by flow cytometry using the B cell markers CD19 and B220 (FIG. 65). The B cells expressing matched b12 H and L chains, possessing either IgM or IgD transmembrane regions, were activated for 18-20 hours with JRFL SOSIP as soluble protein or liposomal preparation and stained with fluorescent antibodies specific for the B cell activation markers CD69, CD86 and MHC class II. The B cell activation markers CD86, CD69, and MHC II were upregulated in a dose-dependent manner in both formulations. However, increases in the levels of CD69 and CD86 were significantly greater following incubation with the trimer-conjugated liposomes compared to the soluble trimers (FIG. 59A), indicating that the multivalent array of the HIV-1 trimers was more effective for the induction of BCR signaling and activation. As shown in FIG. 59B, in addition to the increased MFI values associated with liposomal activation, a clear shift in CD69 levels present on the cell-surface was observed in a greater percentage of B cells incubated with the trimer-conjugated liposomes compared to those incubated with soluble trimers. Next, Applicants assessed the expression of proinflammatory cytokines following overnight incubation of the B cells with the two trimer-types. Applicants assessed proinflammatory cytokines since they are often produced at higher quantities benefitting ease of detection and WEHI B cells were shown previously to express TNF-$\alpha$ (Canfield et al., 2005). By ELISA, the levels of TNF-$\alpha$ and IL-6 levels were significantly increased in the culture medium of the B cells incubated with the trimer-conjugated liposomes compared to the soluble trimers (*P=0.0001 and P=0.008 respectively). These data are consistent with the benefit of multivalent trimer particulate array to enhance B cell activation. Applicants performed additional experiments using blank liposomes (4% DGS-NTA(Ni) liposomes lacking trimers) as negative controls compared to the JRFL SOSIP-conjugated liposomes. The induction of cell-surface activation markers and the levels of cytokines induced by the blank liposomes was negligible compared to the trimer-conjugated liposomes, confirming that that the B cells were specifically activated by the trimers arrayed on the surface of the liposomes (FIG. 59D). Since the liposomes used for these experiments were generated without MPLA and R848, Applicants confirmed that their integrity was similar to liposomes formulated with these TLR agonists by negative stain EM (FIG. 63E).

Germinal Center (GC) B Cells are More Efficiently Activated by the Trimer-Conjugated Liposomes Compared to Soluble Trimers.

Figure 60A:
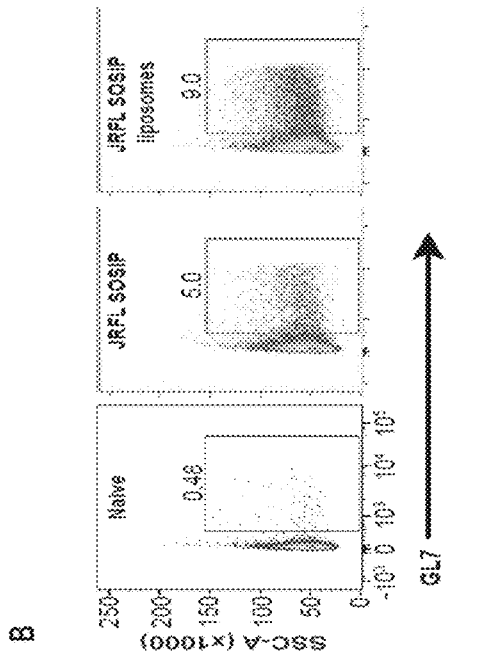
Figure 60B:
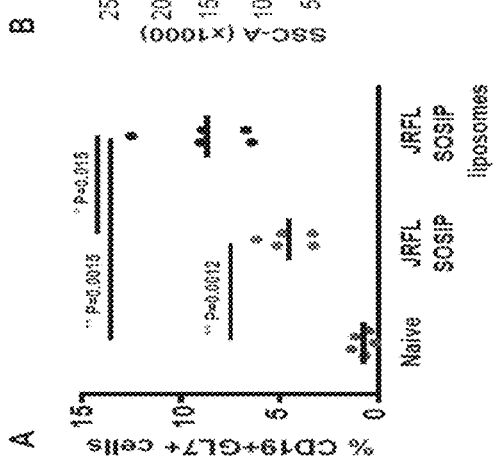
Figure 60C:
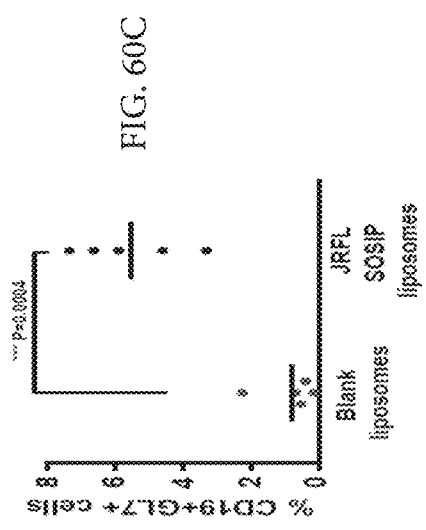

GCs are formed in secondary lymphoid organs such as lymph nodes (LNs) and spleen, where activated B cells proliferate and undergo immunoglobulin isotype class switching and somatic hypermutation (Victora and Nussenzweig, 2012). To assess the capacity of the multivalent trimer liposomal array in formation of GCs relative to the soluble trimers, Applicants separated C57BL/6 mice into 3 groups (5 mice per group) and inoculated with PBS (naïve), soluble JRFL SOSIP trimers in ISCOMATRIX™ adjuvant (CSL, Australia), and JRFL SOSIP trimer-containing liposomes in ISCOMATRIX™ adjuvant. Applicants confirmed that the ISCOMATRIX™ adjuvant did not affect the trimers by EM (FIG. 63D). Fourteen days following inoculation, Applicants observed that the draining LNs were larger in the protein/adjuvant-inoculated mice as compared to the naïve mice. Applicants isolated single cells from the LNs of the 5 mice in each of the three groups and performed flow cytometry analysis of CD19+ B cells positive for the GC marker, GL7. The flow cytometry analysis indicated a higher percentage of B cells positive for GL7 in mice inoculated with the JRFL SOSIP-conjugated liposomes compared to mice inoculated with the soluble JRFL SOSIP trimers. Specifically, Applicants observed that the soluble trimers displayed a significantly increased percentage of GL19+ GL7+ B cells compared to naïve mice analyzed similarly (P=0.0012) as did the trimer-conjugated liposome mice (P=0.0015). More importantly, the Env trimers arrayed on the surface of the liposomes elicited a statistically significant increase in the percentage of CD19+GL7+ B cells compared to the levels elicited by the soluble trimers (*P=0.0152, FIG. 60A and FIG. 60B), indicating more efficient GC formation was induced by particulate, multivalent trimer array. To ensure that the increase in GL7+ B cells was elicited by the trimers conjugated to liposomal surface and was not due to non-specific activation from the liposomes themselves or inadvertent acquisition of a contaminant during processing (ie, endotoxin), Applicants performed additional control experiments with blank liposomes (4% DGS-NTA(Ni) liposomes lacking trimers) or JRFL SOSIP-conjugated liposomes. Fourteen days post inoculation, the percentage of CD19+GL7+ cells present in LNs derived from individual mice were analyzed. Mice immunized with the JRFL SOSIP-conjugated liposomes possessed significantly higher GL7+ B cells compared to mice immunized with the blank liposomes (***P=0.0004; FIG. 60C).

Binding and Neutralizing Antibodies Elicited by Trimer Liposomal Array Compared to Soluble Trimers.

Given the promising antigenic profile of the well-ordered trimers and the ability of the liposome array of the spike mimetics to activate B cells more efficiently both ex vivo and in vivo compared to the soluble spikes, Applicants next tested the trimer-conjugated liposomes formulated in adjuvant for immunogenicity in a pilot rabbit study. Applicants also sought to determine if inclusion of innate-response-activating TLR agonists into the liposomes would augment antibody responses. Three groups of four rabbits each were immunized with 25 μg of protein either as soluble protein trimer in adjuvant or arrayed on the surface of 4% DGS-NTA(Ni) liposomes containing TLR ligands either with or without adjuvant. Control animals were immunized with blank liposomes containing TLR ligands with adjuvant. Prior to inoculation, the trimer protein concentrations on the liposomes were assessed by protein dye to confirm and quantify the Env content per volume of liposome.

After 3 immunizations, IgG titers were elicited against JRFL SOSIP as measured by ELISA with JRFL SOSIP captured on the plate by the anti-His mAb (see FIG. 61B). The soluble trimers in adjuvant elicited relatively low, but detectable, binding titers to the His-captured SOSIP immunogen. The trimer-conjugated liposomes with the incorporated TLR agonists, but not formulated in the exogenous adjuvant, elicited very little IgG antibody response, indicating that the TLR ligands contributed little to activate the adaptive immune response to Env in vivo. In contrast, the trimer-conjugated liposomes (+TLR ligands) but formulated in exogenous adjuvant, elicited much higher native-trimer binding titers compared to both trimer:liposomes (+TLR ligands) lacking exogenous adjuvant and the soluble trimers formulated in exogenous adjuvant. Taken together, these comparative data sets demonstrated that the liposomal presentation of the trimers rendered them more immunogenic than soluble trimers in the presence of exogenous adjuvant. Blank liposomes in adjuvant, as expected, elicited no detectable trimer binding antibodies in the serum.

Figure 66A:
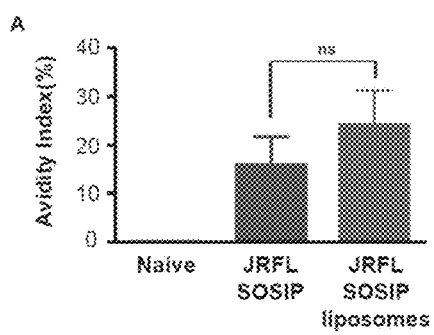
FIGS. 66A-B depict immunogenicity of JRFL SOSIP trimer-conjugated liposomes. (A) Immunizations with JRFL SOSIP:liposomes elicit antibodies with higher avidity than soluble protein. New Zealand white rabbits were immunized 4 times with 25 ug JRFL SOSIP protein as soluble or conjugated to 4% Ni DGPC liposomes. Sera after the 3rd boost was analyzed by ELISA with sodium isothiocyanate (NaSCN) treatment for avidity measurements. Percentage avidity index is defined as (ED50 value with NaSCN treatment/ED50 value without NaSCN treatment)×100. P values were calculated with two-tailed unpaired t test. (B) Midpoint IgG titers of rabbits after 4 and 8 weeks post fourth inoculation analyzed by ELISA with JRFL SOSIP trimers captured on plate via the C-terminal His6tag (SEQ ID NO: 3).
Figure 66B:
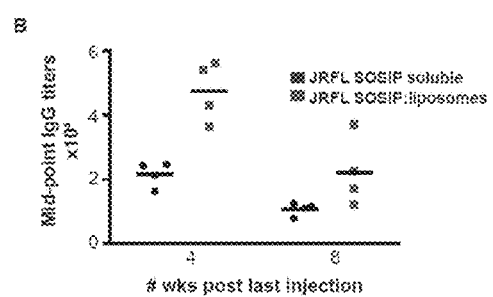

Due to the initial results indicating that the trimer-conjugated liposomes in adjuvant were more immunogenic than the soluble trimers in adjuvant, Applicants performed additional boosts at 5 week intervals and assessed binding titers in a longitudinal manner. Applicants observed that there was a trend for the liposomal trimers to elicit higher binding titers to the native spike mimetics compared to the soluble trimers over the course of immunization (FIG. 61C). Together these data indicated that the trimer-conjugated liposomes were more immunogenic, and that the trimer integrity was maintained in vivo when present on the liposome surface. To further evaluate the quality of the antibody response, Applicants assessed the avidity of the sera to JRFL SOSIP captured on plate by anti-His antibody. The animals immunized with trimer-conjugated liposomes possessed antibodies displaying higher avidity than those receiving soluble trimers, however, the increased avidity was not statistically significant (FIG. 66A).

Next, to determine the quality of the neutralizing response, Applicants performed HIV pseudo-virus neutralization assays (Li et al., 2005). Applicants used sera isolated from individual animals immunized with each trimer-type 14 days following each inoculation with either soluble or trimer-conjugated liposomes. Following both the 3rd and 4th immunization, Applicants detected modest autologous tier 2-like JRFL neutralizing titers from 3 of 4 rabbits receiving the trimer-conjugated liposomes. Only one animal immunized with the soluble trimers displayed weak neutralizing activity at these time points. Although there was a trend for increased neutralization titers elicited by the trimer-conjugated liposomes compared to the soluble trimers, and in more animals per group, as well as boosting of trimer-conjugated liposomes compared to the soluble trimers, these differences were not statistically significant in this small pilot study (FIG. 61D and FIG. 61E).

In this Example, Applicants made use of the new well-ordered Env trimers recently designed in the laboratory to create a high-density multi-variant array of these recombinant glycoprotein HIV spike mimetics on the surface of fully synthetic liposomes. Applicants generated synthetic nickel containing liposomes by incorporating lipids bearing Ni+2 at the polar head group into the lipid bilayer, to capture the C-terminally His6-tagged trimers ("His6" disclosed as SEQ ID NO: 3). Applicants demonstrated by both negative staining and cryo-EM that both the NFL and SOSIP trimers could be arrayed at high-density, were stable, and displayed a favorable antigenic profile following coupling to the surface of the fully synthetic liposomes. Applicants showed that the well-ordered, trimer-conjugated liposomes more efficiently activated B cells ex vivo compared to soluble trimers and better generated GC B cells in vivo in wild-type mice in a statistically significant manner. The trimer-conjugated liposomes displayed a trend to elicit both native binding antibodies and neutralizing antibodies against an HIV-1 tier 2 strain that is more resistant to vaccine-elicited neutralizing antibodies.

These data indicate that Applicants have developed a flexible platform, in which potentially any His-tagged Env trimer can be arrayed at high density. Applicants could array literally hundreds of trimers per particle, perhaps overcoming immune evasion mechanisms that HIV has evolved naturally to reduce activation of host B cells. The non-glycosylated bottom surface of the trimers is blocked by capture using the His tag on the C-terminus of the trimers on the liposomal surface. This non-glycosylated surface was recently shown to be highly immunogenic, potentially diverting neutralizing responses, rendering the SOSIP immunogens incapable of eliciting neutralizing titers in mice (Hu et al., 2015). The high density and uniform array indicates that all three of the His6 tags bound to nickel on the liposome, although Applicants do not have direct evidence for this possibility. Array of the trimers on the liposomes may stabilize more distal regions of Env as the V3 is partially exposed on JRFL Env (more so than most other tier 2 viruses), however, on the JRFL trimer-conjugated liposomes, Applicants could not detect any V3 binding, even with IgG avidity in play. The well-ordered trimers also exhibit enhanced stabilization on the liposomes, as at 4° C. they remain tightly trimeric and arrayed at high density over a period of multiple months.

In terms of B cell activation, the multivalent trimer array on the surface of the liposomes seems to impart advantages in terms of B cell activation both ex vivo and in vivo. Applicants used mouse B cells expressing the bNAb b12, and showed that there is enhanced activation of these B cells, presumably via avidity gained by the high-density multivalent array. Although the increased secretion of IL-6 from the purified B cells following induction by the trimer-conjugated liposomes was consistent with known cytokine profiles, that TNF alpha secretion was also increased was somewhat surprising as this cytokine is not usually secreted by naïve murine B cells, although it has been reported to be secreted by human B cells (Plzakova et al., 2014) and WEHI B cells (Canfield et al., 2005). This may indicate superantigen effects by trimer multi-valent array or most likely, an altered cytokine profile in these engineered B cells. Less likely, TNF-α secretion is indirect and occurs by dose-dependent activation of a small percentage of myeloid cells in the greater than 99% pure B cell population.

In terms of immunogenicity in vivo, in a pilot rabbit study, the trimer-conjugated liposomes displayed a trend to induce increased binding titers to the native-like trimers compared to the soluble trimers. The enhanced binding titers were detectable beyond a boost or two, an initial indication of longevity of the B cell response. This scenario is reminiscent of the arrayed L1 protein of the highly successful HPV vaccine, which imparts long-lived antibody secreting B cells in humans (Schiller and Chackerian, 2014; Schiller and Lowy, 2015). It will be very interesting to determine if the Env-conjugated liposomes can accomplish prolonged antibody secretion in non-human primates on the pre-clinical pathway toward a vaccine candidate using this type of system. Inclusion of TLR agonists into the liposomal formulation did not render the trimers very immunogenic, indicating that at least for the levels of TLR agonist incorporated here, and the subcutaneous route of administration, these ligands contributed little to the adaptive immune response to the trimers. The data shown here indicates a clear trend of benefit of multivalent array over soluble trimers in vivo in the presence of exogenous adjuvant. However, due to the small numbers of animals per group in this initial study, statistical significance was not achieved. Neutralizing capacity, although not robust in Applicants' study, again displayed a trend to be preferentially induced by the trimer-conjugated liposomes, but again did not achieve statistical significance. Why Applicants do not elicit tier 2 autologous neutralizing responses approaching the levels reported by Sanders et al (Sanders et al., 2015) is unclear, but the JRFL strain used here is generally resistant to vaccine-induced antibodies, as apparently is not the case for BG505 when SOSIPs are inoculated into rabbits. In fact, for BG505, monomeric gp120 can efficiently elicit autologous tier 2 neutralization in rabbits, whereas JRFL gp120 does not elicit autologous tier 2 neutralizing antibodies (Beddows et al., 2007). Further investigation will be needed to determine trimer-virus pairing in regards to the elicitation of autologous tier 2 neutralizing antibodies, as well as the elicitation of neutralizing antibodies in different animal models using matched well-ordered trimer immunogens.

Due to the flexibility of the liposomal system described here, expansion to incorporate well-ordered trimers from other clades onto the liposomal surface is possible either as a diverse array of trimers on independent particles or with different trimers from the same subtype or from different clades arrayed on the same liposome. Such array may have advantages to enhance responses to conserved and common B cell epitopes and neutralizing determinants. Using the approach described here, Applicants demonstrate proof-of-concept using Ni-dependent capture of well-ordered HIV trimers as immunogens. For clinical applications of this approach, Applicants may need to use other divalent cationic lipids possessing cobalt or zinc due to potential nickel inflammatory issues or it might be beneficial to use available maleimide-conjugated lipids to capture trimers possessing a free C-terminal cysteine per protomer of each trimer to reduce any concerns about release from the liposomal surface in vivo.

In summary, Applicants present here initial analysis of multivalent array of ordered HIV trimers conjugated to liposomes in vitro, improved over Applicants' previous Env:proteoliposome studies (Grundner et al., 2002), and their potential advantages as an improved immunogenic platform to more efficiently activate B cell responses ex vivo and in vivo.

Figure 67:
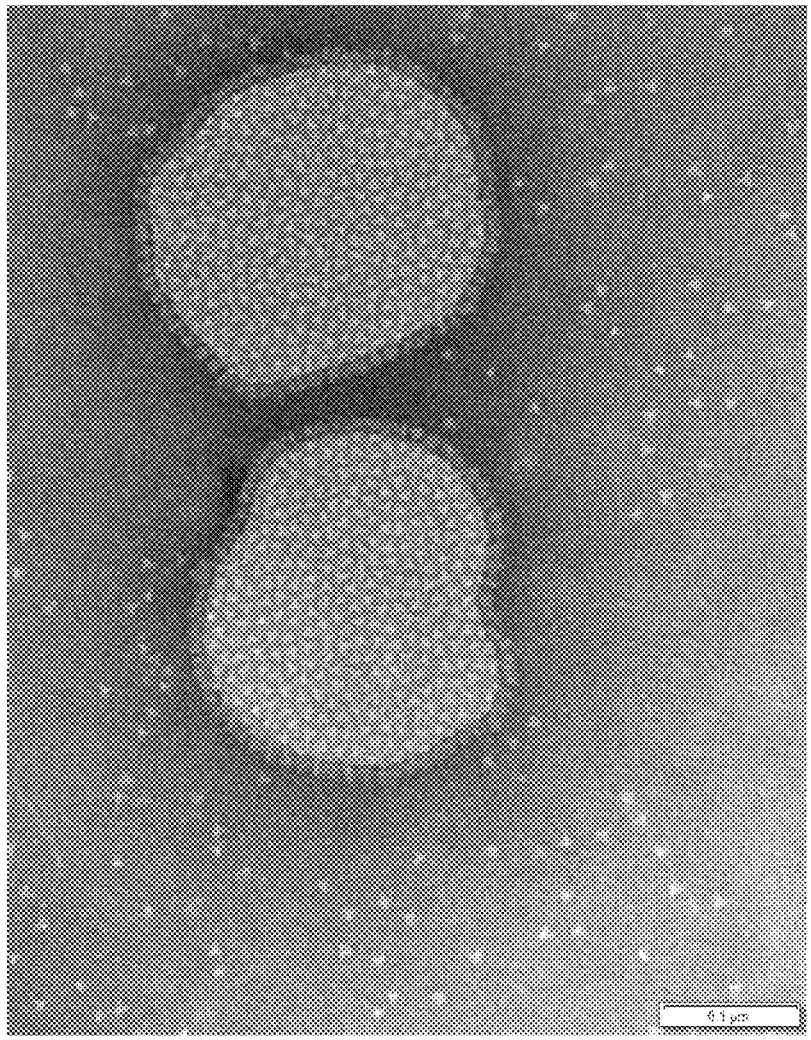
FIG. 67 depicts cobalt Liposomes coupling to BG505 NFL2.
Figure 68:
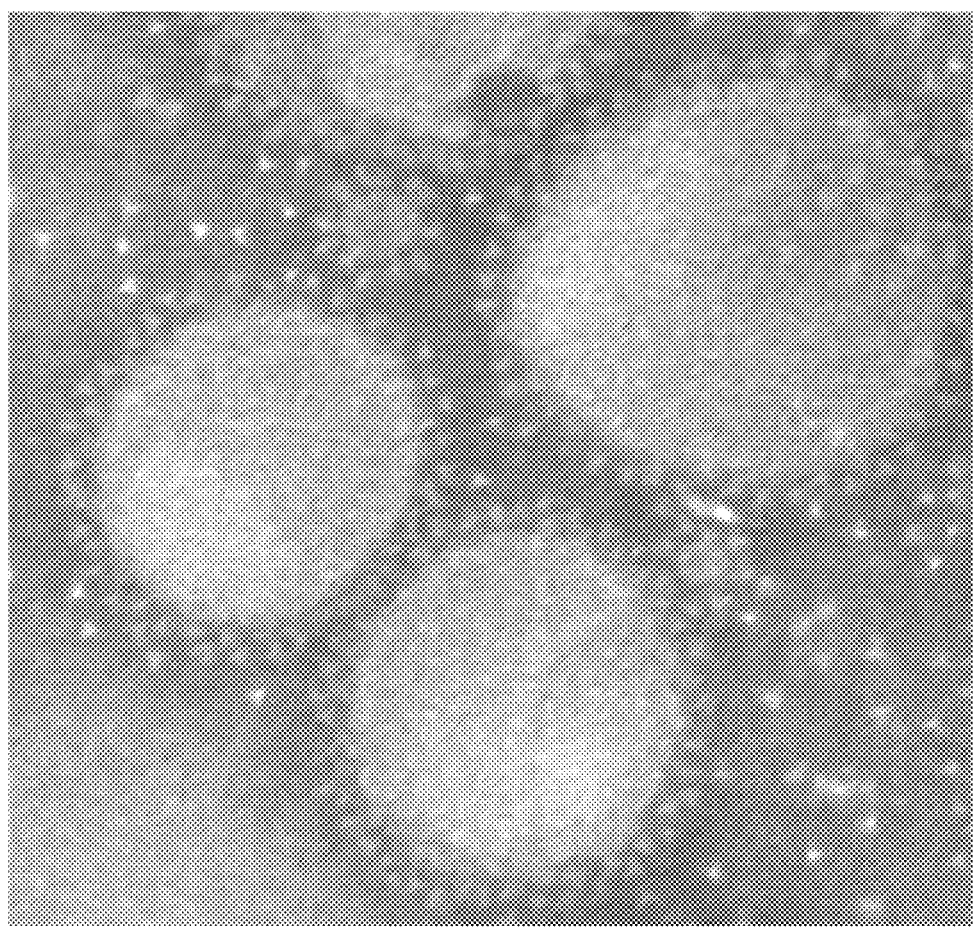
FIG. 68 depicts covalent coupling of Liposomes to free cysteine on BG505 NFL2.
Figure 69:
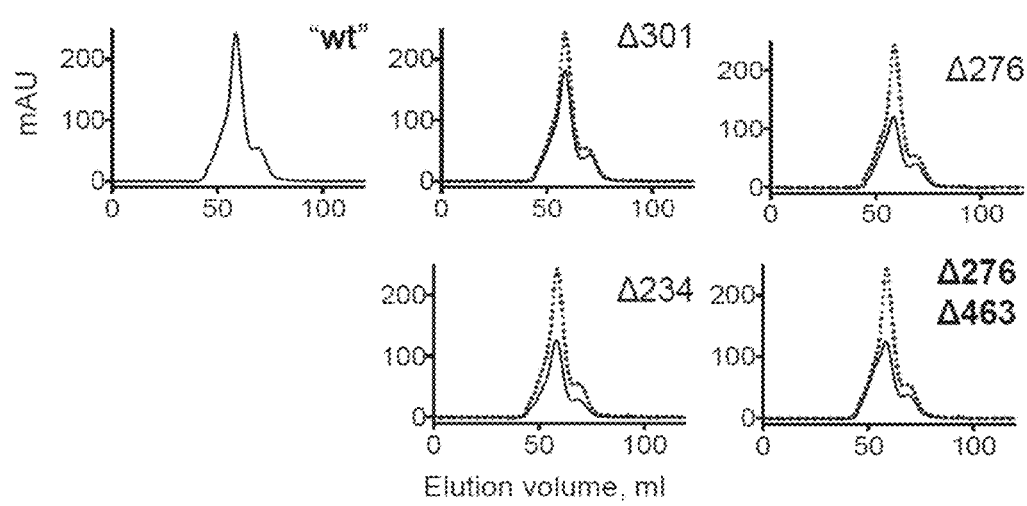
FIG. 69 depicts SEC profiles of glycan deleted 16055 NFL2 TD CC1 GL2 variants.
Figure 70:
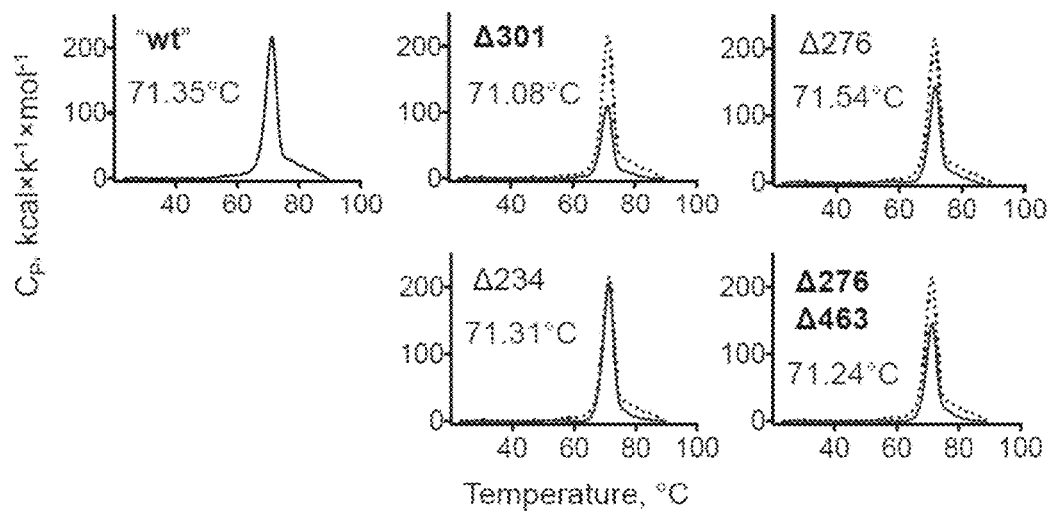
FIG. 70 depicts thermostability of the 16055 NFL2 TD CC1 GL2 trimer affected by the glycan deletions. DSC thermal transition curves and derived Tm of glycan deleted trimers (blue) compared to the backbone protein (black).
Figure 71:
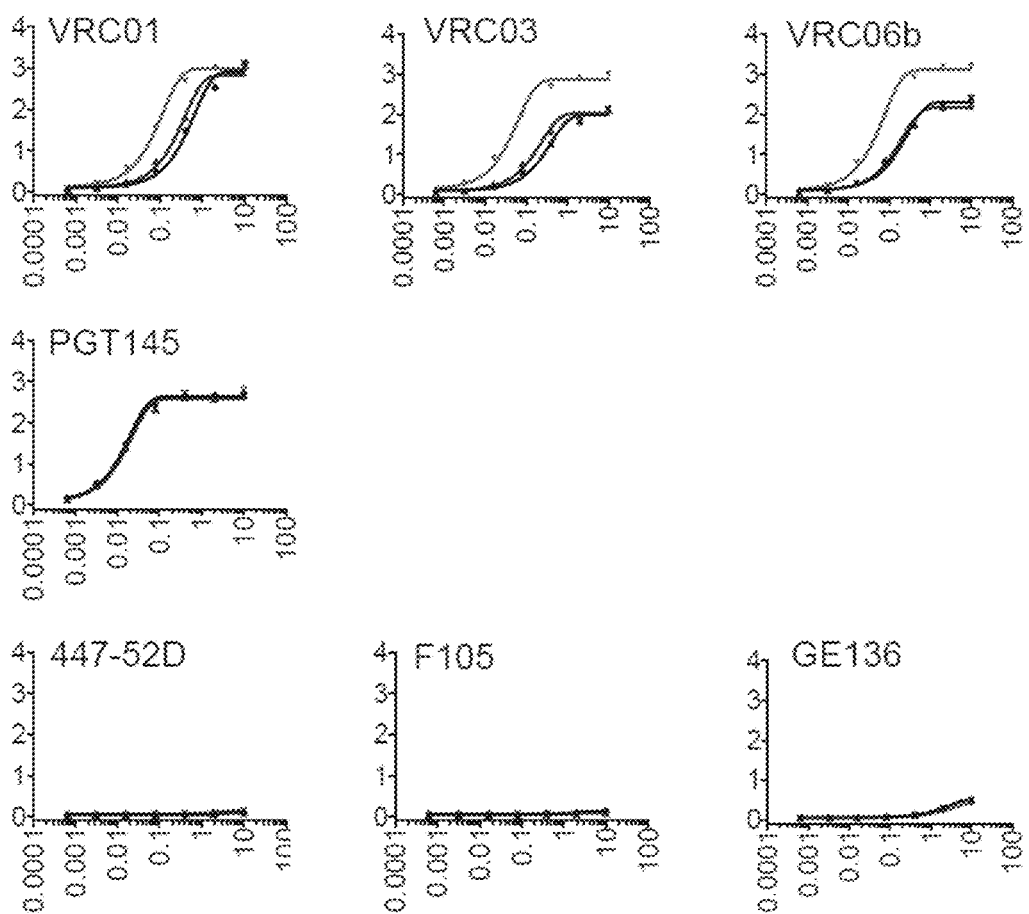
FIG. 71 depicts an antibody binding profile of Δ4276 Δ463 and Δ301 glycan deleted variants confirms better accessibility of the CDbs.
Figure 72:
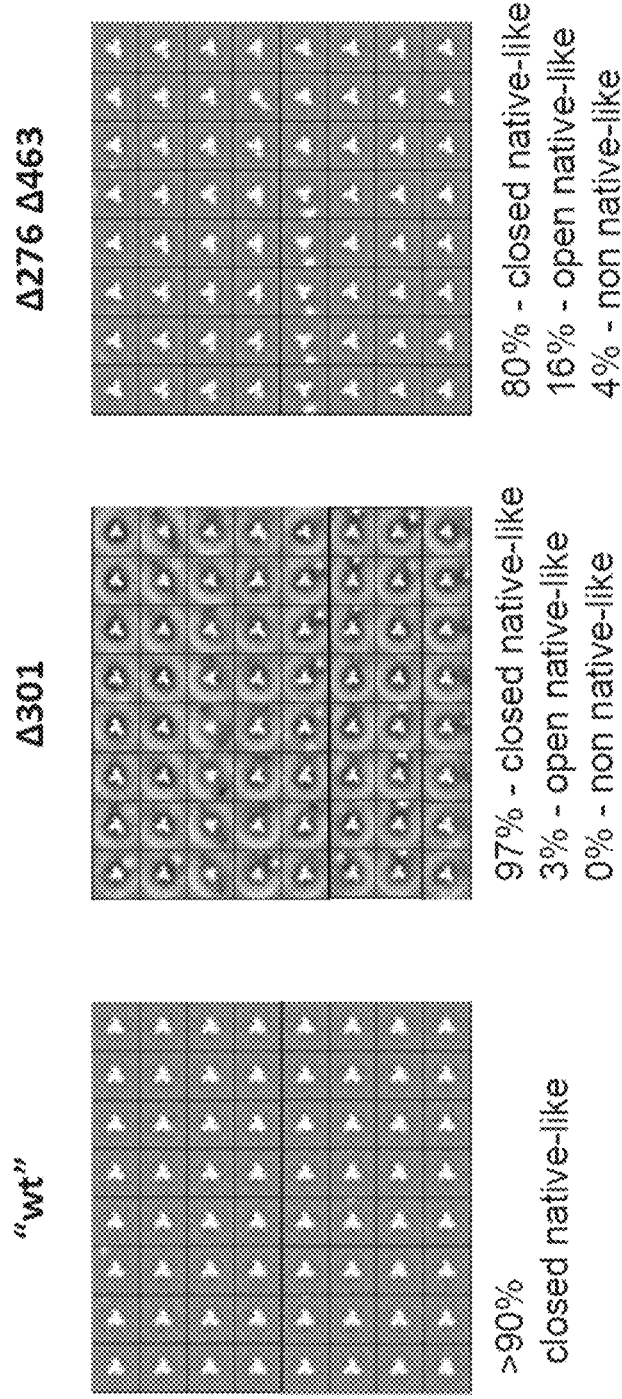
FIG. 72 depicts a computational analysis of the EM images which confirms Native-like conformation of the glycan-deleted trimers.
Figure 73:
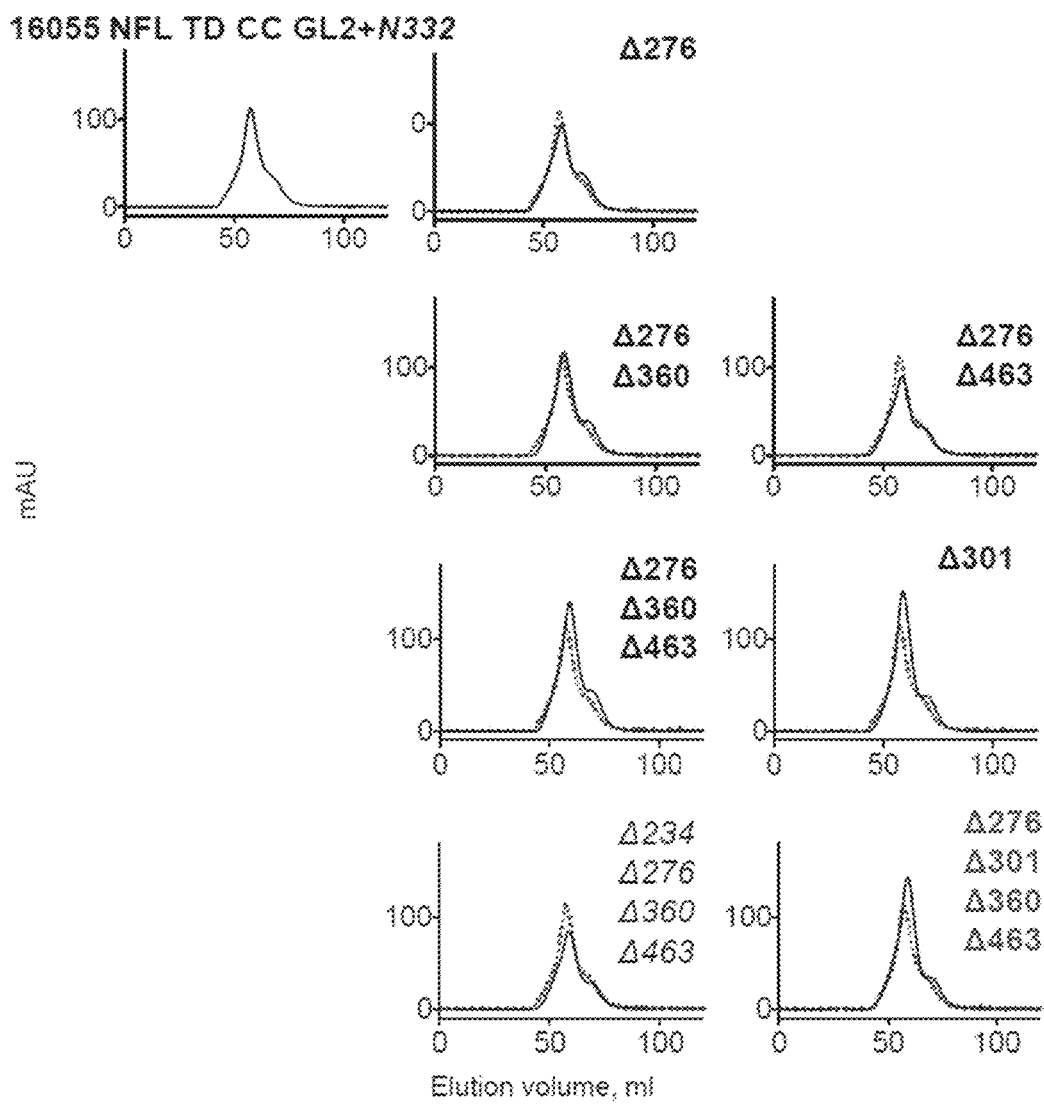
FIG. 73 depicts SEC profiles of glycan deleted 16055 NFL2 TD CC1 GL2+N332 variants.
Figure 74:
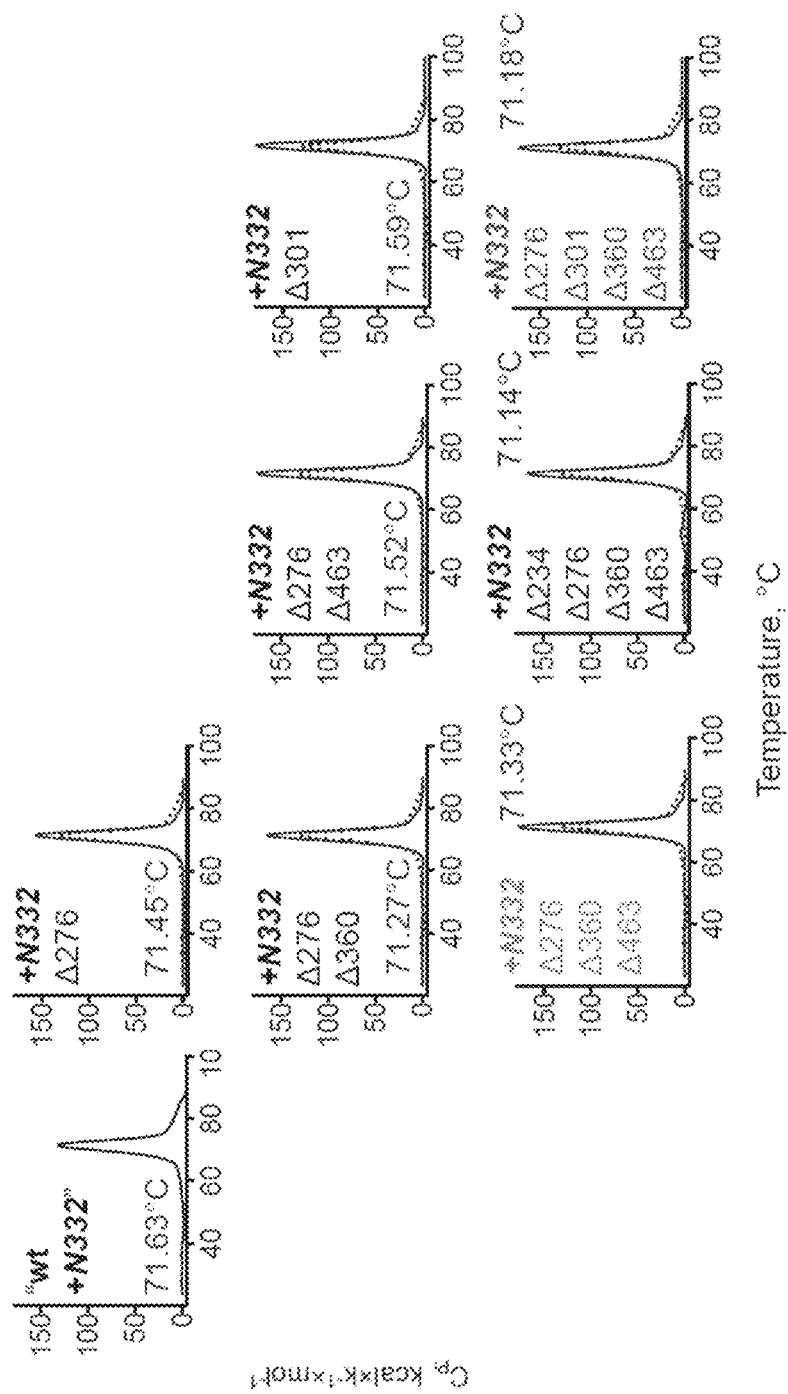
FIG. 74 depicts thermostability of the 16055 NFL2 TD CC1 GL2 N332 trimer affected by the glycan deletions. DSC thermal transition curves and derived Tm of glycan deleted trimers (blue) compared to the backbone protein (black).
Figure 75:
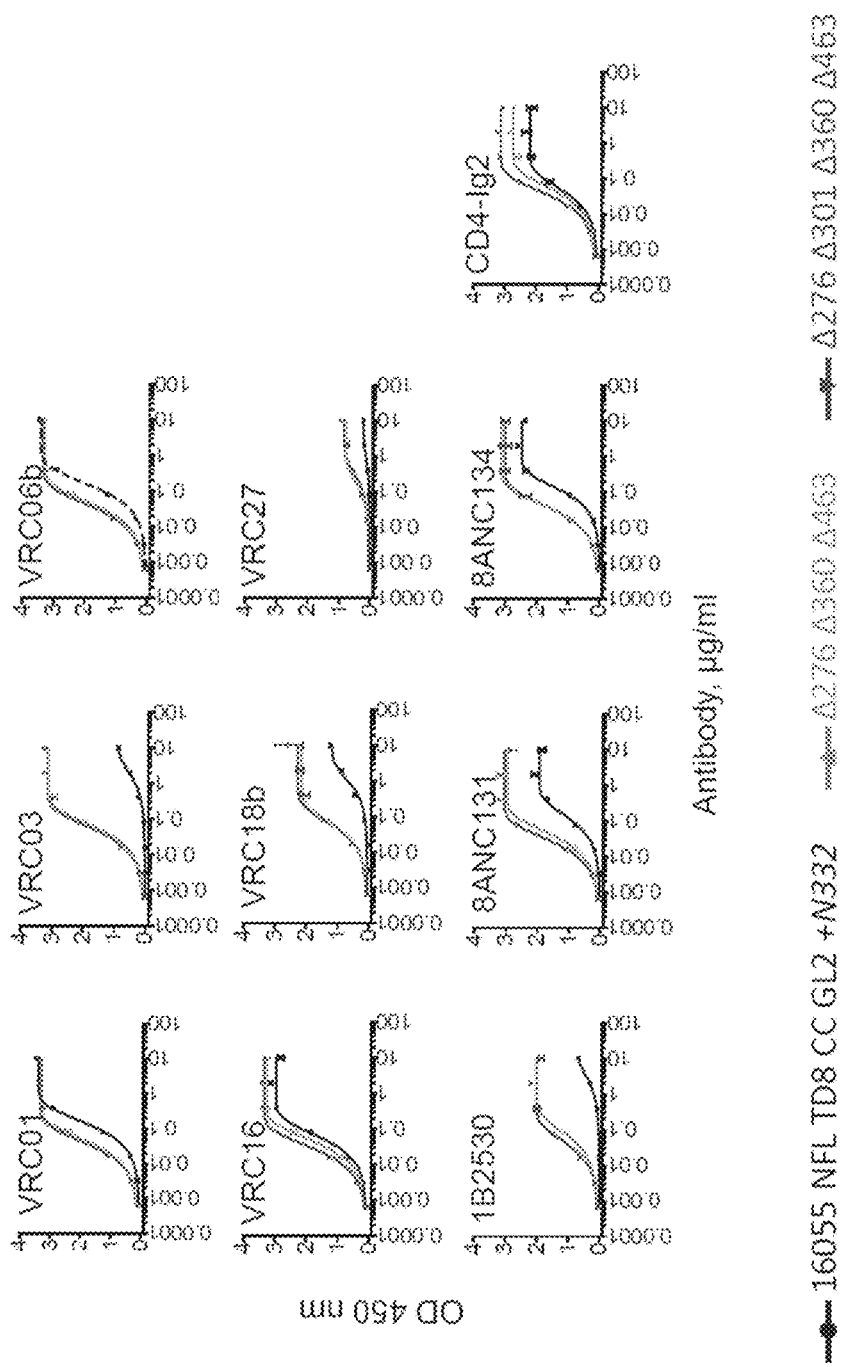
FIG. 75 depicts an antibody binding profile of Δ276 Δ360 Δ463 and Δ276 Δ301 Δ360 Δ463 glycan deleted variants confirms better accessibility of the CDbs.
Figure 76:
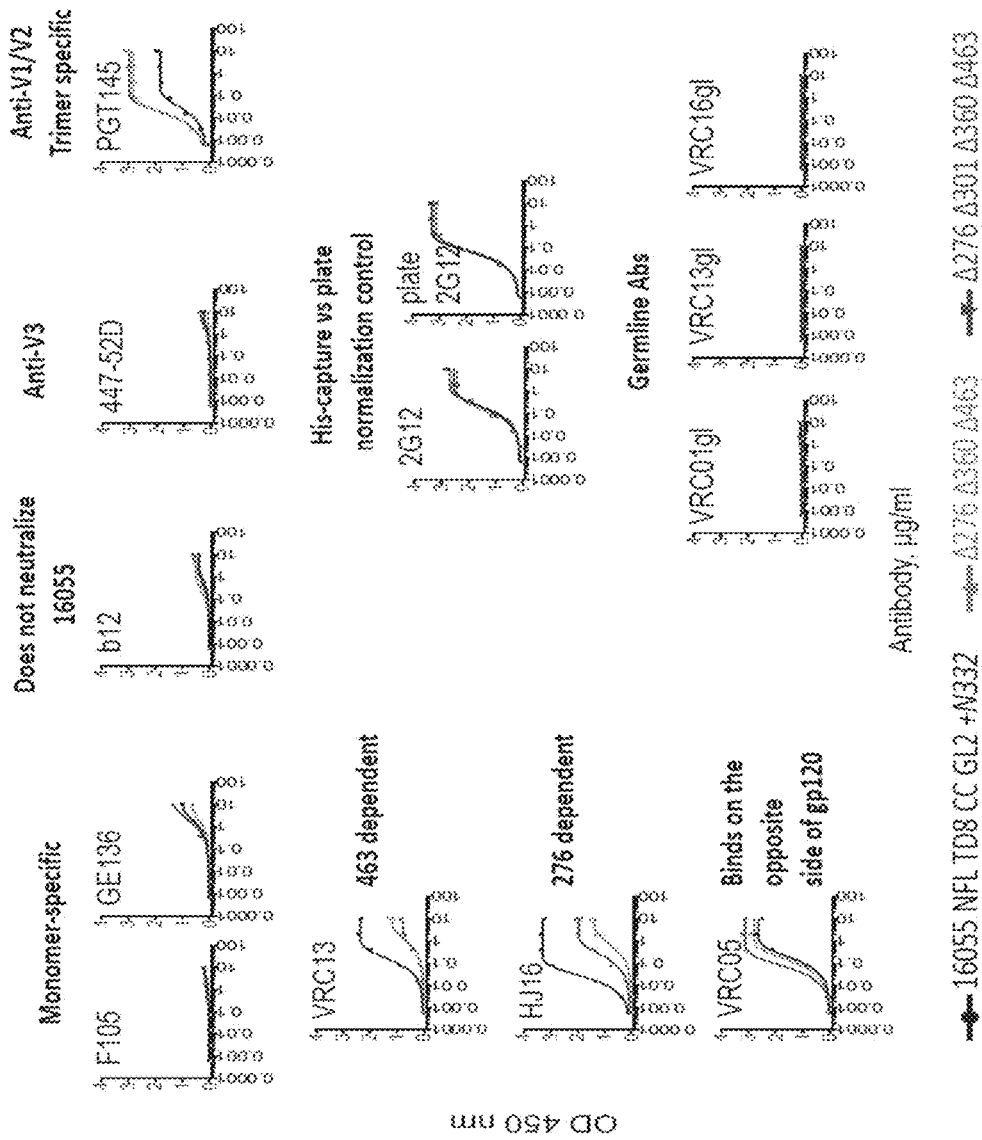
FIG. 76 depicts control antibodies binding profiles of Δ276 Δ360 Δ463 and Δ276 Δ301 Δ360 Δ463 glycan deleted variants.
Figure 77:
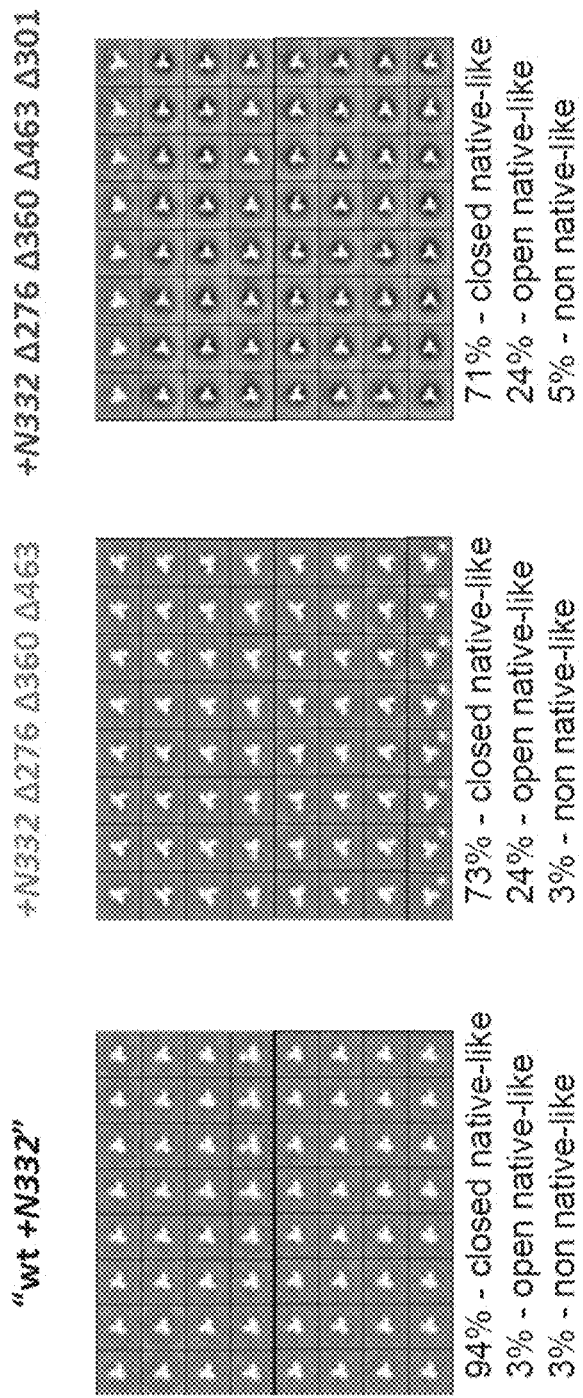
FIG. 77 depicts computational analysis of the EM images which confirms Native-like conformation of the glycan-deleted trimers.
Figure 78:
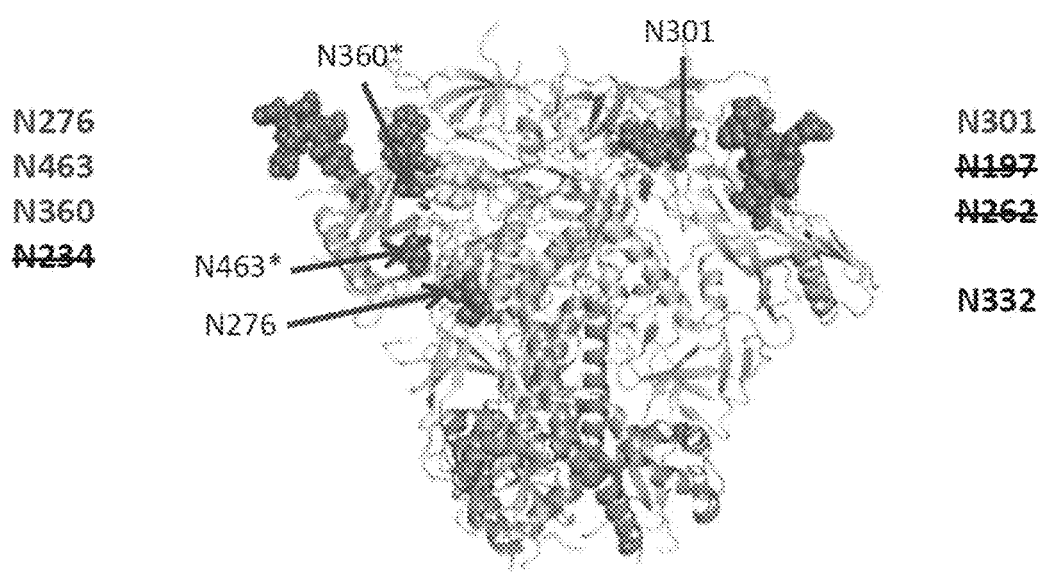
FIG. 78 depicts three variants for cell surface/pseudovirus glycan deletions: 1. Δ276, 2. Δ301 and 3. Δ276 Δ360 Δ463.
Figure 79:
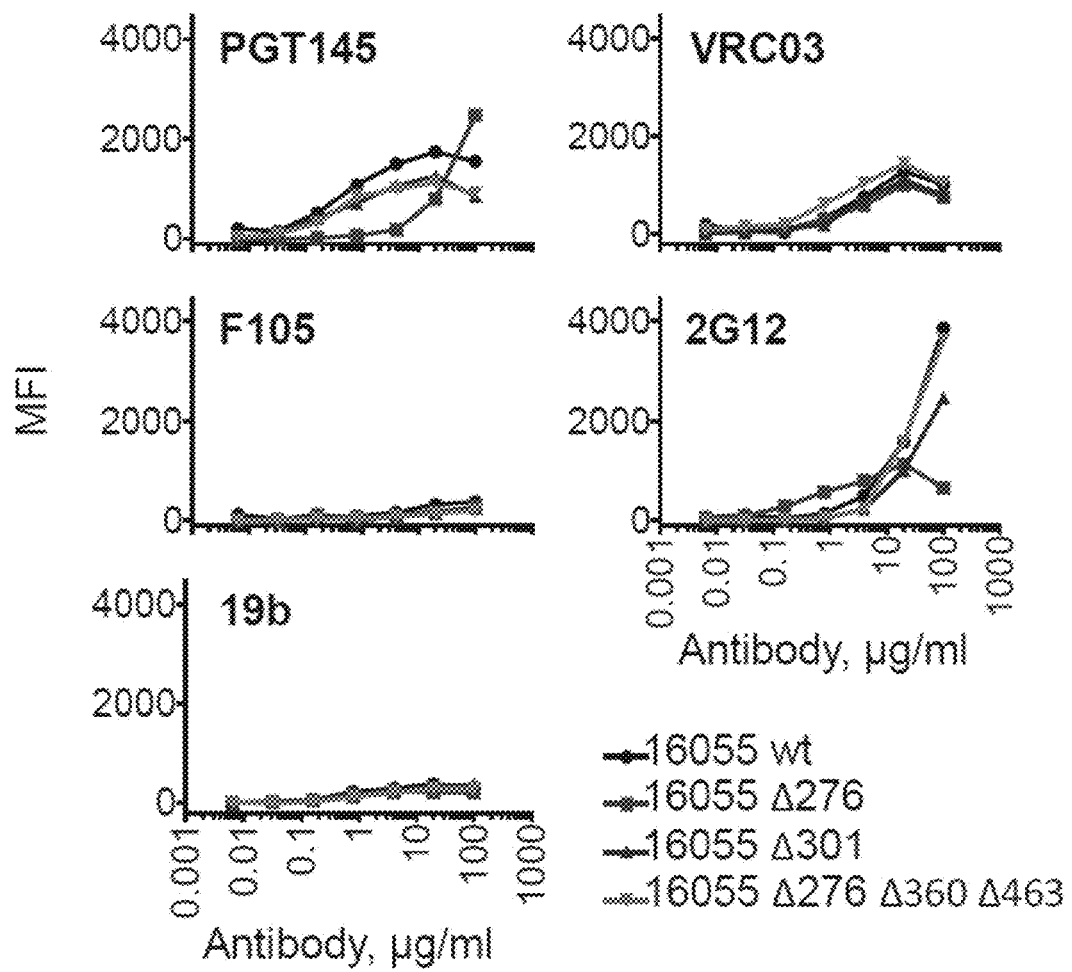
FIG. 79 depicts 293T cells surface expressed mutated 16055 envelopes maintain native-like quaternary structure and do not have V3 loop or nonbroadly neutralizing epitopes exposure.
Figure 80:
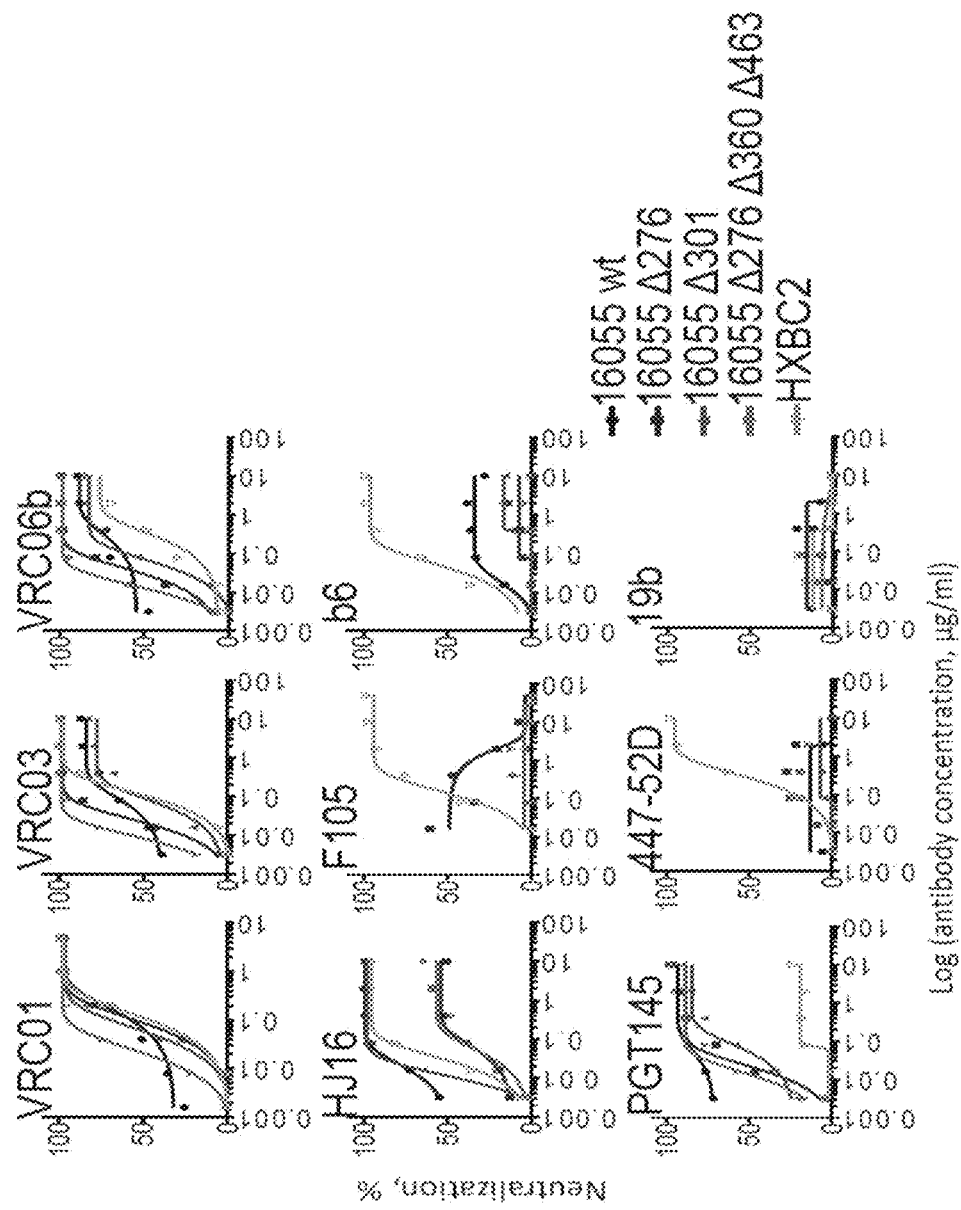
FIG. 80 depicts pseudoviruses with glycan deletions retain tier 2 phenotype.
Figure 82:
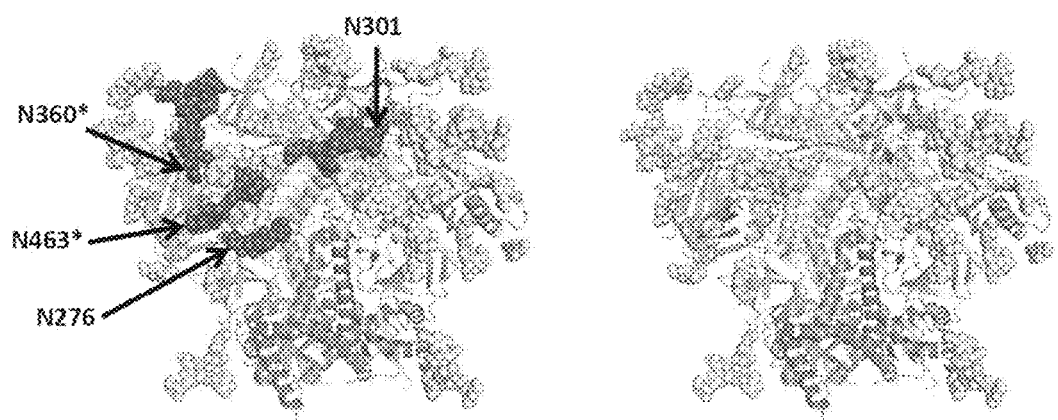
FIG. 82 depicts deleted CD4 binding site proximal N-glycans. CD4 binding loop in yellow, N-linked glycans in blue, gp120 in green and gp41 in brown.

Applicants can now couple liposomes to BG505 Env, and the more stable NFLs versions of 16055, JRFL and BG505 Env. Applicants can successfully couple Env to liposomes incorporating Cobalt as the chelating metal (rather than Nickel). Applicants can covalently couple Env to liposomes by conjugating free cysteine on Env to maleimide group on the liposomes. FIG. 67 depicts cobalt Liposomes coupling to BG505 NFL2 and FIG. 68 depicts covalent coupling of Liposomes to free cysteine on BG505 NFL2.

Expression and Purification of Recombinant HIV-1 Trimer Proteins.

JRFL SOSIP and JRFL NFL trimers were expressed in serum-free medium by transient transfection of HEK293F cells (Invitrogen) with plasmid DNA as described previously (Sharma et al., 2015). In brief, the secreted proteins were purified by *galanthus* lectin affinity chromatography followed by size exclusion chromatography (SEC). Next, the trimer peak was subjected to negative selection by the non-neutralizing monoclonal antibody, F105 to retain disordered trimers on the column. The flow through from the F105 column, containing the well-ordered trimers, was resolved by a second SEC column to isolate a homogenous fraction of well-ordered trimers.

Liposome Preparation, Protein Conjugation and Lipid and Protein Quantitation.

For DLS, Octet, EM, GC analysis, and immunization, the liposomes were composed of a molar ratio of 50:36:4:5:5 of DGPC, cholesterol, DGS-NTA(Ni), Monophosphoryl lipid A (MPLA) (synthetic) PHAD™ (Avanti Polar Lipids), and R848 (InvivoGen). For ex-vivo studies, liposomes were composed of a molar ratio of 60:36:4 of 1,2-distearoyl-sn-glycero-3-phosphocholine (DGPC) (Avanti Polar Lipids), cholesterol (Sigma Lifescience), and [(5-amino-1-carboxypentyl) imino di acetic acid) succinyl] (nickel salt) (DGS-NTA(Ni)) (Avanti Polar Lipids). To form the liposomes, the above constituents were mixed in the appropriate ratios in chloroform, incubated over glass and chloroform was evaporated in the presence of gaseous nitrogen. The resulting lipid film was dried further O/N in a desiccator. The lipids were hydrated in PBS for 2 hours at 37° C. with constant shaking followed by vigorous sonication for 30 seconds. Next, the liposomes were extruded for a minimum of 15 times through 1 µm, 0.8 µm, 0.4 µm, 0.2 µm, and 0.1 µm filters using a hand-held mini-extrusion device (Avanti Polar Lipids) at room temperature (RT). For conjugation of protein to the liposomes, 2.2 mg of trimer protein was added to 500 µl of liposomes and incubated at RT for 2 hours. The unbound protein was removed from the liposomes by passing the liposome mixture through Superdex 100 column. The liposome fractions were collected, pooled and stored at 4° C.

JRFL SOSIP and JRFL NFL trimers conjugated on the liposomes were quantitated using a standard curve generated by either soluble JRFL SOSIP or JRFL NFL trimers, respectively, using Advanced Protein Assay Reagent (Cytoskeleton) according to manufacturer's instructions. Phosphorous in liposomes was estimated by a colorimetric assay reported earlier. Briefly, phosphorous (Sigma) standard curve was generated and used to determine the amounts of phosphorous in the liposome samples. First, the organic samples were digested to inorganic phosphate by heating the samples at 215° C. for 25 min, followed by addition of hydrogen peroxide and continued heating for additional 30 min. Next, ammonium molybdate and ascorbic acid were added sequentially and again the samples were heated at 100° C. for 7 min. The absorbance at 820 nm was determined for both the standard and the experimental samples.

Electron Microscopy.

For negative stain EM, liposomes were applied for 3 minutes onto a glow discharged carbon-coated 400-Cu mesh grids (Electron Microscopy Sciences, Hatfield, Pa.). Excess sample was removed and the grids were immediately placed on a droplet of 2% phosphotungstic acid solution (pH 6.9) for 2 minutes. Excess stain was removed and the grids were allowed to dry thoroughly. Grids were examined on a Philips CM100 electron microscope (FEI, Hillsbrough Oreg.) at 80 kV, and images were acquired with a Megaview III charge-coupled device (CCD) camera (Olympus Soft Imaging Solutions Germany). For cryo EM, samples were preserved undiluted in vitrified ice supported by holey carbon films on 400-mesh copper grids. Samples were prepared by applying 3 µl drop of sample suspension to a clean grid blotting away excess with filter paper and immediately proceeded with vitrification in liquid ethane. Grids were stored under liquid nitrogen until transferred to the electron microscope for imaging. Electron microscopy was performed using an FEI Tecnai T12 electron microscope operating at 120 keV equipped with an FEI Eagle 4 k×4 k CCD camera. Vitreous ice grids were transferred into the electron microscope using a cryostage that maintains the grids at a temperature below −170° C.

Bio-Layer Light Interferometry (BLI).

Binding interactions between monoclonal antibodies (mAbs) and the trimers conjugated to the liposome surface or soluble trimers were examined by BLI using an Octet RED system (ForteBio). Biotinylated Wheat Germ Agglutinin (WGA) (Vector Laboratories) was captured on Streptavidin biosensors (ForteBio) at 50 µg/ml in PBS-B (PBS with 0.1% BSA) for 180 sec followed by wash for 180 sec in PBS-B. Next, the liposomes conjugated with trimers (10 µg/ml) were loaded onto the WGA sensors for 30 min followed by wash for 60 min. The biosensors were immersed in PBS-B aliquoted in 96 well plates to generate a baseline. Next, the biosensors were immersed in a separate 96 well plate filled with PBS-B containing the mAbs (20 µg/ml) for 5 min to allow association of the immobilized trimers with antibody. Association was followed by dissociation in PBS-B for 30 min. A constant temperature of 30° C. was maintained inside the instrument during all reactions. A reference sensor was generated during each experimental run to ensure that there was minimal level of non-specific binding of mAbs to the WGA sensors.

B-Cell Activation Assay.

B-cells from spleen and lymph nodes were purified by negative selection using MACS® separation (Miltenyi Biotec) that uses monoclonal antibodies specific for T cells and monocytes conjugated to the paramagnetic bead to retain all cells but B cells on the solid phase. Cells were plated as 1×105 cells/well in a 96 well plate and stimulated with 50 µg/ml, 5 µg/ml and 0.5 µg/ml of soluble JRFL SOSIP trimers, JRFL SOSIP trimers conjugated to the 4% DGS-NTA(Ni) liposomes or 4% DGS-NTA(Ni) liposomes for 18-20 hours. The supernatants were stored at −20° C. for TNF-α and IL-6 ELISAs. Next, the cells were stained with fluorescent antibodies specific for CD86, CD69, and MEW II prior to analysis by Flow Cytometry. The experiment was performed in two independent experiments from different mature b12 mAb transgenic mice (Ota et al., 2013).

Animal Inoculations.

New Zealand white female rabbits were inoculated subcutaneously with 25 µg of protein as either soluble or conjugated to 4% DGS-NTA(Ni) liposomes and formulated in 20% of Adjuplex™ (Advanced BioAdjuvants) in a total volume of 150 µl. For the control group, blank 4% DGS-NTA(Ni) liposomes with MPLA and R848 were formulated in 20% of Adjuplex™. The liposomes contained 30 µg MPLA and 6.5 µg R848 per each injection. Test bleeds were collected two weeks after each inoculation. To determine in vivo GC formation, 3 groups of 6 weeks old C57BL/6 mice (5 mice per group) were subcutaneously inoculated in the hind legs by hock injection (Kamala, 2007) with either PBS, 10 µg of soluble JRFL SOSIP trimeric protein formulated in 1 unit of ISCOMATRIX, 10 µg of JRFL SOSIP trimeric protein conjugated to 4% DGS-NTA(Ni) liposomes formulated in 1 unit of ISCOMATRIX, or 4% DGS-NTA(Ni) liposomes formulated in 1 unit of ISCOMATRIX in a total volume of 100 µl. Fourteen days following inoculation, the draining popliteal lymph nodes were isolated and prepared as single cell suspensions and subjected to staining with mAbs as described below.

ELISA.

ELISAs were performed in 96-well MaxiSorp plates (Nalgene Nunc International). Plates were coated for 4 hrs at RT with anti-His tag mAb (2 µg/ml; R&D Systems). After blocking the plates with non-fat milk and fetal bovine serum (FBS) for overnight at 4° C., the plates were incubated with JRFL SOSIP trimeric protein at 2 µg/ml for 2 hr at room temperature. Next, the plates were incubated with five-fold serial dilutions of the immune sera starting at 1:200, and after 1 hr were washed with buffer, followed by incubation with HRP-conjugated anti-rabbit IgG (1:5000) or HRP-conjugated anti-rabbit IgM (1:5000) for detection. The plates were developed by a chromogenic substrate for HRP, 3,3',5, 5'-tetramethylbenzidine (Life Technologies). Reactions were stopped by the addition of sulfuric acid and absorbance was measured at 450 nm. For ex-vivo studies, culture supernatants were collected and cytokine ELISAs were performed using DuoSet ELISA Development Kits (R&D Systems) according to manufacturer's instructions.

Neutralization Assay.

The pseudoviruses were prepared and neutralization assays were performed as described previously (Li et al., 2005). Briefly, rabbit sera were diluted and pre-incubated with virus (200,000 RLU) for 30 min at 37 C before adding to 10,000 TZM-bl reporter cells per well. These cells contain an integrated luciferase gene under the control of the Tat-sensitive HIV LTR. Virus was incubated for cells the cells for 48 hrs to allow infection and potential luciferase induction, after which the cells were lysed, and relative luciferase units were measured by a Victor luminometer (PerkinElmer).

Flow Cytometry of Mouse LN-Derived B Cells.

Murine lymph nodes were gently disrupted through a 70 µm cell sieve, followed by extensive washing. All cells were labeled with live/dead cell viability reagent (Invitrogen) followed by blocking with anti-mouse CD16/CD32 (BD Pharmingen). Next, the cells were incubated with APC anti-mouse CD19 and FITC anti-mouse GL7 (BioLegend) and post-fixed with paraformaldehyde before acquiring cells on an LSRII (Becton Dickinson) to determine fluorescent mAb binding. Data were analysed with FlowJo software (TreeStar).

Binding Analysis of Selected mAbs to JRFL SOSIP.

Binding interactions between selected trimer-preferring and CDbs-directed antibodies to JRFL SOSIP trimers were examined by biolayer light interferometry (BLI) using Octet Red system (ForteBio). The mAbs were captured on the surface of the anti-human Fc sensors from a solution of 5 µg/ml in PBS for 60 s at 1,000 rpm. Bio-sensors were then immersed in a solution of the JRFL SOSIP trimers (diluted to 200 nM) for 600 s at 1,000 rpm to allow association of the immobilized antibodies with the analyte. Association was followed by dissociation in PBS for 600 s at 1,000 rpm.

Electron Microscopy.

JRFL SOSIP-conjugated liposomes were mixed at a 10% (v/v) with ISCOMATRIX and Adjuplex and incubated at 37° C. for 1 h. 5 µl of the mixture was stained with phosphor tungstate on carbon-coated Cu grids. The grids were examined on a Philips CM100 electron microscope. (FEI, Hillsbrough Oreg.) at 80 kV and images were acquired with a Megaview III charge-coupled device (CCD) camera.

Avidity Measurements.

For avidity measurements, the ELISAs were developed as described previously, with an additional washing step. After the incubation of the sera, the plates were washed and incubated for 15 min with 1.5M sodium isothio cynate (NaSCN) in PBS, while duplicate plates were incubated with an equal volume of PBS. The plates were then washed again to remove dissociated antibody and detection of bound antibody was performed.

REFERENCES

Arsov, Z., and Quaroni, L. (2007). Direct interaction between cholesterol and phosphatidylcholines in hydrated membranes revealed by ATR-FTIR spectroscopy. Chem Phys Lipids 150, 35-48.

Beddows, S., Franti, M., Dey, A. K., Kirschner, M., Iyer, S. P., Fisch, D. C., Ketas, T., Yuste, E., Desrosiers, R. C., Klasse, P. J., et al. (2007). A comparative immunogenicity study in rabbits of disulfide-stabilized, proteolytically cleaved, soluble trimeric human immunodeficiency virus type 1 gp140, trimeric cleavage-defective gp140 and monomeric gp120. Virology 360, 329-340.

Burton, D. R., Desrosiers, R. C., Doms, R. W., Koff, W. C., Kwong, P. D., Moore, J. P., Nabel, G. J., Sodroski, J., Wilson, I. A., and Wyatt, R. T. (2004). HIV vaccine design and the neutralizing antibody problem. Nature Immunology 5, 233-236.

Burton, D. R., Pyati, J., Koduri, R., Sharp, S. J., Thornton, G. B., Parren, P. W., Sawyer, L. S., Hendry, R. M., Dunlop, N., Nara, P. L., and et al. (1994). Efficient neutralization of primary isolates of HIV-1 by a recombinant human monoclonal antibody. Science 266, 1024-1027.

Caldeira Jdo, C., Medford, A., Kines, R. C., Lino, C. A., Schiller, J. T., Chackerian, B., and Peabody, D. S. (2010). Immunogenic display of diverse peptides, including a broadly cross-type neutralizing human papillomavirus L2 epitope, on virus-like particles of the RNA bacteriophage PP7. Vaccine 28, 4384-4393.

Canfield, S., Lee, Y., Schroder, A., and Rothman, P. (2005). Cutting edge: IL-4 induces suppressor of cytokine signaling-3 expression in B cells by a mechanism dependent on activation of p38 MAPK. J Immunol 174, 2494-2498.

Deml, L., Kratochwil, G., Osterrieder, N., Knuchel, R., Wolf, H., and Wagner, R. (1997). Increased incorporation of chimeric human immunodeficiency virus type 1 gp120 proteins into Pr55gag virus-like particles by an Epstein-Barr virus gp220/350-derived transmembrane domain. Virology 235, 10-25.

Falkowska, E., Le, K. M., Ramos, A., Doores, K. J., Lee, J. H., Blattner, C., Ramirez, A., Derking, R., van Gils, M. J., Liang, C. H., et al. (2014). Broadly neutralizing HIV antibodies define a glycan-dependent epitope on the pre-fusion conformation of gp41 on cleaved envelope trimers. Immunity 40, 657-668.

Grundner, C., Mirzabekov, T., Sodroski, J., and Wyatt, R. (2002). Solid-phase proteoliposomes containing human immunodeficiency virus envelope glycoproteins. Journal of virology 76, 3511-3521.

Guenaga, J., de Val, N., Tran, K., Feng, Y., Satchwell, K., Ward, A. B., and Wyatt, R. T. (2015). Well-ordered trimeric HIV-1 subtype B and C soluble spike mimetics generated by negative selection display native-like properties. PLoS Pathog 11, e1004570.

Hu, J. K., Crampton, J. C., Cupo, A., Ketas, T., van Gils, M. J., Sliepen, K., de Taeye, S. W., Sok, D., Ozorowski, G., Deresa, I., et al. (2015). Murine antibody responses to cleaved soluble HIV-1 envelope trimers are highly restricted in specificity. Journal of virology.

Julien, J. P., Cupo, A., Sok, D., Stanfield, R. L., Lyumkis, D., Deller, M. C., Klasse, P. J., Burton, D. R., Sanders, R. W., Moore, J. P., et al. (2013). Crystal structure of a soluble cleaved HIV-1 envelope trimer. Science 342, 1477-1483.

Kamala, T. (2007). Hock immunization: a humane alternative to mouse footpad injections. J Immunol Methods 328, 204-214.

Kovacs, J. M., Noeldeke, E., Ha, H. J., Peng, H., Rits-Volloch, S., Harrison, S. C., and Chen, B. (2014). Stable, uncleaved HIV-1 envelope glycoprotein gp140 forms a tightly folded trimer with a native-like structure. Proceedings of the National Academy of Sciences of the United States of America 111, 18542-18547.

Li, M., Gao, F., Mascola, J. R., Stamatatos, L., Polonis, V. R., Koutsoukos, M., Voss, G., Goepfert, P., Gilbert, P., Greene, K. M., et al. (2005). Human immunodeficiency virus type 1 env clones from acute and early subtype B infections for standardized assessments of vaccine-elicited neutralizing antibodies. Journal of virology 79, 10108-10125.

Li, Y., O'Dell, S., Wilson, R., Wu, X., Schmidt, S. D., Hogerkorp, C. M., Louder, M. K., Longo, N. S., Poulsen, C., Guenaga, J., et al. (2012). HIV-1 neutralizing antibodies display dual recognition of the primary and coreceptor binding sites and preferential binding to fully cleaved envelope glycoproteins. Journal of virology 86, 11231-11241.

Liao, H. X., Lynch, R., Zhou, T., Gao, F., Alam, S. M., Boyd, S. D., Fire, A. Z., Roskin, K. M., Schramm, C. A., Zhang, Z., et al. (2013). Co-evolution of a broadly neutralizing HIV-1 antibody and founder virus. Nature 496, 469-476.

McLellan, J. S., Pancera, M., Carrico, C., Gorman, J., Julien, J. P., Khayat, R., Louder, R., Pejchal, R., Sastry, M., Dai, K., et al. (2011). Structure of HIV-1 gp120 V1/V2 domain with broadly neutralizing antibody PG9. Nature 480, 336-343.

Ota, T., Doyle-Cooper, C., Cooper, A. B., Doores, K. J., Aoki-Ota, M., Le, K., Schief, W. R., Wyatt, R. T., Burton, D. R., and Nemazee, D. (2013). B cells from knock-in mice expressing broadly neutralizing HIV antibody b12 carry an innocuous B cell receptor responsive to HIV vaccine candidates. J Immunol 191, 3179-3185.

Pancera, M., Zhou, T., Druz, A., Georgiev, I. S., Soto, C., Gorman, J., Huang, J., Acharya, P., Chuang, G. Y., Ofek, G., et al. (2014). Structure and immune recognition of trimeric pre-fusion HIV-1 Env. Nature 514, 455-461.

Pejawar-Gaddy, S., Kovacs, J. M., Barouch, D. H., Chen, B., and Irvine, D. J. (2014). Design of lipid nanocapsule delivery vehicles for multivalent display of recombinant Env trimers in HIV vaccination. Bioconjug Chem 25, 1470-1478.

Pejchal, R., Walker, L. M., Stanfield, R. L., Phogat, S. K., Koff, W. C., Poignard, P., Burton, D. R., and Wilson, I. A. (2010). Structure and function of broadly reactive antibody PG16 reveal an H3 subdomain that mediates potent neutralization of HIV-1. Proceedings of the National Academy of Sciences of the United States of America 107, 11483-11488.

Plzakova, L., Kubelkova, K., Krocova, Z., Zarybnicka, L., Sinkorova, Z., and Macela, A. (2014). B cell subsets are activated and produce cytokines during early phases of Francisella tularensis LVS infection. Microb Pathog 75, 49-58.

Posner, M. R., Cavacini, L. A., Emes, C. L., Power, J., and Byrn, R. (1993). Neutralization of HIV-1 by F105, a human monoclonal antibody to the CD4 binding site of gp120. J Acquir Immune Defic Syndr 6, 7-14.

Ringe, R. P., Yasmeen, A., Ozorowski, G., Go, E. P., Pritchard, L. K., Guttman, M., Ketas, T. A., Cottrell, C. A., Wilson, I. A., Sanders, R. W., et al. (2015). Influences on the Design and Purification of Soluble, Recombinant Native-Like HIV-1 Envelope Glycoprotein Trimers. Journal of virology 89, 12189-12210.

Safaeian, M., Porras, C., Pan, Y., Kreimer, A., Schiller, J. T., Gonzalez, P., Lowy, D. R., Wacholder, S., Schiffman, M., Rodriguez, A. C., et al. (2013). Durable antibody responses following one dose of the bivalent human papillomavirus L1 virus-like particle vaccine in the Costa Rica Vaccine Trial. Cancer Prev Res (Phila) 6, 1242-1250.

Sanders, R. W., Derking, R., Cupo, A., Julien, J. P., Yasmeen, A., de Val, N., Kim, H. J., Blattner, C., de la Pena, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS Pathog 9, e1003618.

Sanders, R. W., van Gils, M. J., Derking, R., Sok, D., Ketas, T. J., Burger, J. A., Ozorowski, G., Cupo, A., Simonich, C., Goo, L., et al. (2015). HIV-1 VACCINES. HIV-1 neutralizing antibodies induced by native-like envelope trimers. Science 349, aac4223.

Schiller, J., and Chackerian, B. (2014). Why HIV virions have low numbers of envelope spikes: implications for vaccine development. PLoS Pathog 10, e1004254.

Schiller, J. T., and Lowy, D. R. (2015). Raising expectations for subunit vaccine. J Infect Dis 211, 1373-1375.

Sharma, S. K., de Val, N., Bale, S., Guenaga, J., Tran, K., Feng, Y., Dubrovskaya, V., Ward, A. B., and Wyatt, R. T. (2015). Cleavage-independent HIV-1 Env trimers engineered as soluble native spike mimetics for vaccine design. Cell Rep 11, 539-550.

Sok, D., van Gils, M. J., Pauthner, M., Julien, J. P., Saye-Francisco, K. L., Hsueh, J., Briney, B., Lee, J. H., Le, K. M., Lee, P. S., et al. (2014). Recombinant HIV envelope trimer selects for quaternary-dependent antibodies targeting the trimer apex. Proceedings of the National Academy of Sciences of the United States of America 111, 17624-17629.

Stanfield, R. L., Gorny, M. K., Williams, C., Zolla-Pazner, S., and Wilson, I. A. (2004). Structural rationale for the broad neutralization of HIV-1 by human monoclonal antibody 447-52D. Structure 12, 193-204.

Tran, E. E., Borgnia, M. J., Kuybeda, O., Schauder, D. M., Bartesaghi, A., Frank, G. A., Sapiro, G., Milne, J. L., and Subramaniam, S. (2012). Structural mechanism of trimeric HIV-1 envelope glycoprotein activation. PLoS Pathog 8, e1002797.

Tran, K., Poulsen, C., Guenaga, J., de Val, N., Wilson, R., Sundling, C., Li, Y., Stanfield, R. L., Wilson, I. A., Ward, A. B., et al. (2014). Vaccine-elicited primate antibodies use a distinct approach to the HIV-1 primary receptor binding site informing vaccine redesign. Proceedings of the National Academy of Sciences of the United States of America 111, E738-747.

Trkola, A., Purtscher, M., Muster, T., Ballaun, C., Buchacher, A., Sullivan, N., Srinivasan, K., Sodroski, J., Moore, J. P., and Katinger, H. (1996). Human monoclonal antibody 2G12 defines a distinctive neutralization epitope on the gp120 glycoprotein of human immunodeficiency virus type 1. Journal of virology 70, 1100-1108.

Victora, G. D., and Nussenzweig, M. C. (2012). Germinal centers. Annu Rev Immunol 30, 429-457.

Wu, X., Zhou, T., Zhu, J., Zhang, B., Georgiev, I., Wang, C., Chen, X., Longo, N. S., Louder, M., McKee, K., et al. (2011). Focused evolution of HIV-1 neutralizing antibodies revealed by structures and deep sequencing. Science 333, 1593-1602.

Example 4: Glycan Deletions

Applicants identified several mutations that lead to glycan deletions in the context of 16055 NFL TD CC GL2, 16055 NFL TD CC GL2 N332 restored, BG505 NFL TD CC GL2 YRR, JRFL NFL TD CC GL2 YRR soluble Env trimers context without affecting trimer quaternary native-like structure and thermostability. These mutations were shown to open up CD4bs (CD4 binding site) of the trimer making it more accessible for the broadly neutralizing CD4bs specific antibodies.

For 16055 NFL TD CC GL2:

Single mutations: N276Q, N234Q, N360Q, N463Q, N301Q

Mutation combinations: N276Q N463Q

For 16055 NFL TD CC GL2 with N332 restored:

Single mutations: N276Q, N234Q, N360Q, N463Q, N301Q

Double mutation: N276QN463Q, N276QN360Q,

Other mutation combinations: N276Q N360Q N463Q, N276Q N234Q N360Q N463Q, N276Q N360Q N463Q N301Q For BG505 NFL TD CC GL2 YRR Single mutations: N276Q, N301Q Double mutation: N276Q N462Q, N276Q N361Q, N276Q N234Q, N301Q N197Q, N301Q N295Q Other mutation combinations: N276Q N361Q N462Q N301Q For JRFL NFL TD CC GL2 YRR Single mutations: N276Q, N301Q Double mutation: N276Q N463Q, N276Q N361Q, N301Q N295Q Other mutation combinations: N276Q N361Q N463Q, N276Q N361Q N463Q N301Q Also Applicants demonstrated that 16055 pseudoviruses expressing Envs with mutations and mutation combinations N276Q, N301Q, N276Q N360Q N463Q maintain tier2 phenotype.

Soluble 16055 NFL TD CC GL2 and 16055 NFL TD CC GL2 N332 proteins with mutations combinations N276Q N463Q or N276Q N360Q N463Q elicit early potent antibody responses against authologoes virus.

FIG. 69 depicts SEC profiles of glycan deleted 16055 NFL2 TD CC1 GL2 variants.

FIG. 70 depicts thermostability of the 16055 NFL2 TD CC1 GL2 trimer affected by the glycan deletions. DSC thermal transition curves and derived Tm of glycan deleted trimers (blue) compared to the backbone protein (black).

FIG. 71 depicts an antibody binding profile of Δ276 Δ463 and Δ301 glycan deleted variants confirms better accessibility of the CDbs.

FIG. 72 depicts a computational analysis of the EM images which confirms Native-like conformation of the glycan-deleted trimers.

FIG. 73 depicts SEC profiles of glycan deleted 16055 NFL2 TD CC1 GL2+N332 variants.

FIG. 74 depicts thermostability of the 16055 NFL2 TD CC1 GL2 N332 trimer affected by the glycan deletions. DSC thermal transition curves and derived Tm of glycan deleted trimers (blue) compared to the backbone protein (black).

FIG. 75 depicts an antibody binding profile of Δ276 Δ360 Δ463 and Δ276 Δ301 Δ360 Δ463 glycan deleted variants confirms better accessibility of the CDbs.

FIG. 76 depicts control antibodes binding profiles of Δ276 Δ360 Δ463 and Δ276 Δ301 Δ360 Δ463 glycan deleted variants.

FIG. 77 depicts computational analysis of the EM images which confirms Native-like conformation of the glycan-deleted trimers.

FIG. 78 depicts three variants for cell surface/pseudovirus glycan deletions: 1. Δ276, 2. Δ301 and 3. Δ276 Δ360 Δ463.

FIG. 79 depicts 293T cells surface expressed mutated 16055 envelopes maintain native-like quaternary structure and do not have V3 loop or nonbroadly neutralizing epitopes exposure.

FIG. 80 depicts pseudoviruses with glycan deletions retain tier 2 phenotype.

FIG. 81 depicts eutralizing $ID_{50}$ titers (sera fold dilution) of serum from Group I and Group II rabbits after 1st, 3rd and 4th immunizations (0, 6, 18 weeks).

The invention is further described by the following numbered paragraphs:

1. An engineered or non-naturally occurring trimer, wherein the trimer is a disulfide stabilized SOSIP trimer and/or a flexibly linked NFL2P trimer derived from the subtype A BG505 Env.
2. The trimer of paragraph 1, wherein the trimer is a disulfide stabilized SOSIP trimer and a flexibly linked NFL2P trimer derived from the subtype A BG505 Env.
3. The trimer of paragraph 1 or 2, wherein the trimer comprises one or more BG505 or JRFL trimer-derived mutations ("TD mutations"), wherein said TD mutations comprise one or more mutations at residue 47, 49, 65, 106, 164, 165, 172, 302, 308, 429, 432, 500, 519, 520, 543, 553, 567, 588 and/or 662.
4. The trimer of paragraph 4, wherein the mutations comprise D at residue 47, E at residue 49, K at residue 65, T at residue 106, E at residue 164, L at residue 165, V at residue 172, Y at residue 302, R at residue 308, R at residue 429, Q at residue 432, R at residue 500, R at residue 519, R at residue 520, N at residue 543, S at residue 553, K at residue 567, R at residue 588 and/or A at residue 662.
5. The trimer of paragraph 3 or 4, wherein the trimers comprise additional mutations at residue 201, 433, 568 and/or 569.
6. The trimer of paragraph 5, wherein the additional mutations comprise C at residue 201 and/or 443 and/or comprise G at residue 568 and/or 569.
7. The trimer of any one of paragraphs 1 to 6, wherein the trimer further a disulfide linkage to prevent CD4-induced conformational changes to lock gp120 in the native-trimer state.
8. The trimer of paragraph 7, wherein the disulfide linkage is at residues 201 and 433 that covalently links the β-sheet 3 to β-sheet 21.
9. A method of eliciting an immune response in a mammal comprising administering an engineered or non-naturally occurring JRFL SOSIP trimer, an engineered or non-naturally occurring JRFL SOSIP trimer or an engineered or non-naturally occurring native flexible linker (NFL) gp140 trimer, wherein a linker covalently joins gp120 with gp41.
10. The method of paragraph 9, wherein the trimer is administered with an adjuvant.
11. The method of paragraph 10, wherein the adjuvant comprises a lecithin, preferably, wherein the adjuvant is a lecithin is combined with an acrylic polymer, a lecithin coated oil droplet in an oil-in-water emulsion or a lecithin and an acrylic polymer in an oil-in-water emulsion.
12. The method of paragraph 11, wherein the adjuvant is ISCOMATRIX or Adjuplex.
13. The method of paragraph 10, wherein the adjuvant comprises alum.
14. The method of paragraph 9, wherein the trimer is administered in a liposome or in a nanoparticle.
15. The method of paragraph 9, wherein the trimer is fixed.
16. The method of paragraph 15, wherein the trimer is fixed in glutaraldehyde.
17. The method of paragraph 15 or 16, wherein the trimer is quenched with glycine.
16. The method of any one of paragraphs 9 to 17, wherein the trimer is any one of the trimers of paragraphs 1 to 8.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. An engineered or non-naturally occurring HIV envelope glycoprotein trimer, wherein the trimer comprises one or more subtype A BG505 Env trimer-derived mutations ("TD mutations"), wherein said TD mutations comprise one or more mutations at residues 47, 49, 65, 106, 164, 165, 172, 302, 308, 429, 432, 500, 519, 520, 543, 553, 567, 588 and/or 662 wherein a numerical position of an amino acid residue of the glycoprotein trimer corresponds with a numerical position of an amino acid residue of JRFL upon direct alignment of the numerical positions of the amino acid residues of the glycoprotein trimer with the numerical positions of the amino acid residues of JRFL, whose sequence as defined in SEQ ID NO: 5 is based on the BG505 numbering system.

2. The trimer of claim 1, wherein the mutations comprise D at residue 47, E at residue 49, K at residue 65, T at residue 106, E at residue 164, L at residue 165, V at residue 172, Y at residue 302, R at residue 308, R at residue 429, Q at residue 432, R at residue 500, R at residue 519, R at residue 520, N at residue 543, S at residue 553, K at residue 567, R at residue 588 and/or A at residue 662.

3. The trimer of claim 1, wherein the trimers comprise additional mutations at residues 201, 433, 568 and/or 569.

4. The trimer of claim 2, wherein the additional mutations comprise C at residue 201 and/or 443 and/or comprise G at residue 568 and/or 569.

5. The trimer of claim 1, wherein the trimer further comprises a disulfide linkage to prevent CD4-induced conformational changes to lock gp120 subunit of the trimer in the native-trimer state.

6. The trimer of claim 5, wherein the disulfide linkage is at residues 201 and 433 of gp120 that covalently link the .beta.-sheet 3 to .beta.-sheet 21 of gp120.

7. A method of eliciting an immune response in a mammal comprising administering the trimer of claim 1.

8. The method of claim 7, wherein the trimer is administered with an adjuvant.

9. The method of claim 8, wherein the adjuvant comprises a lecithin.

10. The method of claim 9, wherein the lecithin is (a) combined with an acrylic polymer, (b) in a coated oil droplet in an oil-in-water emulsion or (c) in an acrylic polymer in an oil-in-water emulsion.

11. The method of claim 8, wherein the adjuvant comprises alum.

12. The method of claim 7, wherein the trimer is administered in a liposome or in a nanoparticle.

13. The method of claim 7, wherein the trimer is fixed.

14. The method of claim 13, wherein the trimer is fixed in glutaraldehyde.

15. The method of claim 7, wherein the trimer is quenched with glycine.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Glu Lys Arg
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser
1               5

<210> SEQ ID NO 3
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Gly Ser
1               5                   10

<210> SEQ ID NO 5
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Leu Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240
```

```
His Gly Ile Arg Pro Val Val Ser Thr Gln Leu Leu Asn Gly Ser
                    245                 250                 255

Leu Ala Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Phe Leu
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Asn Asn Leu Leu Arg Ala Pro Glu Ala Gln Gln Arg Met Leu Lys Leu
545                 550                 555                 560

Thr Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Glu Leu Asp
                645                 650                 655
```

Gly Gly Gly Gly Ser His His His His His His His
            660                 665

<210> SEQ ID NO 6
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Leu Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

```
His Ser Ser Gly Gly Asp Pro Glu Ile Val Met His Ser Phe Asn Cys
            355             360             365

Gly Gly Glu Phe Phe Tyr Cys Asn Ser Thr Gln Leu Phe Asn Ser Thr
    370             375             380

Trp Asn Asn Thr Glu Gly Ser Asn Asn Thr Glu Gly Asn Thr Ile
385             390             395                     400

Thr Leu Pro Cys Arg Ile Lys Gln Ile Ile Asn Met Trp Gln Arg Val
            405             410                     415

Gly Gln Ala Met Tyr Ala Pro Pro Ile Arg Gly Gln Ile Arg Cys Ser
            420             425             430

Ser Asn Ile Thr Gly Leu Leu Leu Thr Arg Asp Gly Gly Ile Asn Glu
            435             440             445

Asn Gly Thr Glu Ile Phe Arg Pro Gly Gly Gly Asp Met Arg Asp Asn
            450             455             460

Trp Arg Ser Glu Leu Tyr Lys Tyr Lys Val Val Lys Ile Glu Pro Leu
465             470             475             480

Gly Val Ala Pro Thr Arg Ala Lys Arg Arg Val Val Gln Gly Gly Gly
            485             490             495

Gly Ser Gly Gly Gly Ser Ala Val Gly Ile Gly Ala Val Phe Leu
            500             505             510

Gly Phe Leu Gly Ala Ala Gly Ser Thr Met Gly Ala Ala Ser Met Thr
            515             520             525

Leu Thr Val Gln Ala Arg Asn Leu Leu Ser Gly Ile Val Gln Gln Gln
            530             535             540

Ser Asn Leu Leu Arg Ala Pro Glu Ala Gln Gln Arg Met Leu Gln Leu
545             550             555             560

Thr Val Trp Gly Ile Lys Gln Leu Gln Ala Arg Val Leu Ala Val Glu
            565             570             575

Arg Tyr Leu Arg Asp Gln Gln Leu Leu Gly Ile Trp Gly Cys Ser Gly
            580             585             590

Lys Leu Ile Cys Thr Thr Ala Val Pro Trp Asn Ala Ser Trp Ser Asn
            595             600             605

Lys Ser Leu Asp Arg Ile Trp Asn Asn Met Thr Trp Met Glu Trp Glu
            610             615             620

Arg Glu Ile Asp Asn Tyr Thr Ser Glu Ile Tyr Thr Leu Ile Glu Glu
625             630             635             640

Ser Gln Asn Gln Gln Glu Lys Asn Glu Gln Glu Leu Leu Ala Leu Asp
            645             650             655

Gly Gly Gly Gly Ser His His His His His His
            660             665
```